US006001591A

United States Patent [19]
Mittal et al.

[11] Patent Number: 6,001,591
[45] Date of Patent: *Dec. 14, 1999

[54] RECOMBINANT BOVINE ADENOVIRUSES

[75] Inventors: Suresh K. Mittal, Saskatoon; Frank L. Graham, Hamilton; Ludvik Prevec, Burlington; Lorne A. Babiuk, Saskatoon, all of Canada

[73] Assignee: University of Saskatchewan, Saskatoon, Canada

[*] Notice: This patent is subject to a terminal disclaimer.

[21] Appl. No.: 08/845,623

[22] Filed: Apr. 25, 1997

Related U.S. Application Data

[62] Division of application No. 08/164,292, Dec. 9, 1993, Pat. No. 5,820,868.

[51] Int. Cl.$^6$ .............................. C12N 15/00; C12N 7/01; C12N 15/86
[52] U.S. Cl. .................. 435/69.1; 435/235.1; 435/320.1; 424/199.1
[58] Field of Search ................................ 424/93.2, 199.1; 514/44; 435/235.1, 320.1, 69.1

[56] References Cited

U.S. PATENT DOCUMENTS

| 3,962,424 | 6/1976 | Zygraich et al. . |
| 4,510,245 | 4/1985 | Cousens et al. . |
| 4,920,209 | 4/1990 | Davis et al. . |
| 5,024,939 | 6/1991 | Gorman . |

FOREIGN PATENT DOCUMENTS

| 2012895 | 9/1990 | Canada . |
| 185573 | 6/1986 | European Pat. Off. . |
| 389286 | 9/1990 | European Pat. Off. . |
| 2642797 | 8/1990 | France . |
| 2657880 | 8/1991 | France . |
| 86/06409 | 11/1986 | WIPO . |
| 91/11525 | 8/1991 | WIPO . |

OTHER PUBLICATIONS

Belák et al., "Subtypes of bovine adenovirus type 2 exhibit major differences in region E3" *Virology* (1986) 153:262–271.

Benkö et al., "Molecular Cloning and physical mapping of the DNA of bovine adenovirus serotype 4; study of the DNA homology among bovine, and porcine adenoviruses" *Journal of General Virology* (1990) 71:465–469.

Berkner, K.L., "Development of Adenovirus Vectors for the Expression of Heterologous Genes" *Biotechniques* (1989) 6:616–629.

Bostock, C.J., "Viruses as Vectors" *Vet. Microbiol.* (1990) 23:55–71.

Boyle et al., "Recombinant fowlpox virus vaccines for poultry" *Immunol. Cell Biol.* (1993) 71:391–397.

Boyle et al., "Vectors for Recombinant Vaccine Delivery" *Animal Parasite Control Utilizing Biotechnology*, ed. W.K. Yong CRC Press, Boca Raton (1992) pp. 25–47.

Boyle, D.B., "How do other Poxviruses fit in as Potential Vectored Vaccine Substrates for Animal Immunizations?" *Res. Virol.* (1989) 140(5):483–491.

Esposito et al., "Infectious Recombinant Vectored Virus Vaccines" *Adv. Vet. Sci. Comp. Med.* (1989) 33:195–247.

Fejér et al., "Multiple enlargements in the right inverted terminal repeat of the DNA of canine adenovirus type 2" *Acta Microbiologica Hungarica* (1992) 39:159–168.

Graham et al., "Cloning and expression of glycoprotein genes in human adenovirus vectors" *J. Cell. Biochem.* (1988) UCLA Symposium on Molecular and Cellular Biology, Suppl. 12B, Abstract F109.

Haj–Ahmad et al., "Development of a helper–independent human adenovirus vector and its use in the transfer of the herpes simplex virus thymidine kinase gene" *J. Virol.* (1986) 57:267–274.

Hu, S.L. et al., "Restriction Analysis and Homology Studies of the Bovine Adenovirus 7 Genome" *J. Virol.* (1984) 51:880–883.

Kaledin, A.S., "Cloning and Sequencing of EIA gene of bovine adenovirus 3 genome" *Sbornik Nauchnykh Trudov–Moskovskaya Veterinaria Akademiya* (1988) 159:78–82 (translation provided).

Kit, S. et al., "Modified–live infectious bovine rhinotracheitis virus vaccine expressing monomer and dimer forms of foot–and–mouth disease capsid protein epitopes on surface of hybrid virus particles" *Arch. Virol.* (1991) 120:1–17.

Kruglyak, V.A. et al., "Cloning Fragments of Virion DNA of Cattle Adenoviruses BAV 3 in pUC 19 Plasmid" *Soviet Agricultural Sciences* (1987) 11:64–67.

Mittal et al., "Sequence analysis of bovine adenovirus type 3 early region 3 and fibre protein genes" *J. Gen. Virol.* (1992) 73:3295–3300.

Moss, B., "Recombinant DNA virus vectors for vaccination" *Semin. Immunol.* (1990) 2:317–327.

Prevec et al., "Use of human adenovirus–based vectors for antigen expression in animals" *J. Gen. Virol.* (1989) 70:429–434.

Spibey, N. et al., "Identification and nucleotide sequence of the early region 1 from canine adenovirus types 1 and 2" *Virus Research* (1989) 14:241–256.

Thomsen, D.R. et al., "Pseudorabies virus as a live virus vector for expression of foreign genes" *Gene* (1987) 5:261–265.

Tikoo, S.K. et al., "Molecular Cloning, Sequencing, and Expression of Functional Bovine Herpesvirus 1 Glycoprotein gIV in Transfected Bovine Cells" *J. Virol.* (1990) 64:5132–5142.

Hu et al., "Sequence homology between bovine and human adenoviruses" *J. Virol.* (1984) 49:604–608.

Verma et al. Nature, vol. 389, pp. 239–242, Sep. 18, 1997.

Orkin et al, Report and recommendations of the panel to assess the NIH investment in research on gene therapy, Dec. 7, 1995.

*Primary Examiner*—Mary E. Mosher
*Attorney, Agent, or Firm*—Morrison & Foerster LLP

[57] ABSTRACT

The present invention provides recombinant bovine adenovirus (BAV) vectors and expression systems for introduction and expression of non-BAV sequences in mammalian cells. Methods for the preparation and use of these vectors and expression systems are also provided.

12 Claims, 51 Drawing Sheets

```
         10         20         30         40         50         60
CATCATCAAT AATCTACAGT ACACTGATGG CAGCGGTCCA ACTGCCAATC ATTTTGCCA 70         80         90        100        110        120
CGTCATTTAT GACGCAACGA CGGCGAGCGT GGCGTGCTGA CGTAACTGTG GGGCGGAGCG 130        140        150        160        170        180
CGTCGCGGAG GCGGGCGGCGC TGGGCGGGGC TGAGGGCGGC GGGGCGGGCG CGCGGGGCGG 190        200        210        220        230        240
CGCGCGGGGC GGGGCGGAGGG GCGGAGTTCC GCACCCGCTA CGTCATTTTC AGACATTTTT 250        260        270        280        290        300
TAGCAAAATT GCGCCTTTTG CAAGCATTTT TCTCACATTT CAGGTATTA GAGGGCGGAT 310        320        330        340        350        360
TTTTGGTGTT CGTACTTCCG TGTCACATAG TTCACTGTCA ATCTTCATTA CGGCTTAGAC 370        380        390        400        410        420
AAATTTTCGG CGTCTTTTCC GGGTTTATGT CCCCGGTCAC CTTTATGACT GTGTGAAACA 430        440        450        460        470        480
CACCTGCCCA TTGTTTACCC TTGGTCAGTT TTTTCGTCTC CTAGGGTGGG AACATCAAGA
```

FIG. IA

```
                    490         500         510         520         530         540
                    ACAAATTGC CGAGTAATTG TGCACCTTTT TCCGCGTTAG GACTGCGTTT CACACGTAGA 550         560         570         580         590         600
       CAGACTTTTT CTCATTTTCT CACACTCCGT CGTCCGCTTC AGAGCTCTGC GTCTTCGCTG 610         620         630         640         650
       CCACC ATG AAG TAC CTG GTC CTC GTT CTC AAC GAC GGC ATG AGT CGA ATT GAA
             Met Lys Tyr Leu Val Leu Val Leu Asn Asp Gly Met Ser Arg Ile Glu 660         670         680         690         700
AAA GCT CTC CTG TGC AGC GAT GGT GAG GTG GAT TTA GAG TGT CAT GAG GTA
Lys Ala Leu Leu Cys Ser Asp Gly Glu Val Asp Leu Glu Cys His Glu Val 710         720         730         740         750
CTT CCC CCT TCT CCC GCG CCT GTC CCC GCT TCT GTG TCA CCC GTG AGG AGT
Leu Pro Pro Ser Pro Ala Pro Val Pro Ala Ser Val Ser Pro Val Arg Ser 760         770         780         790         800
CCT CCT CCT CTG TCT CCG GTG TTT CCT CCG CCA GCC CCG CTT GTG
Pro Pro Pro Leu Ser Pro Val Phe Pro Pro Ser Pro Pro Ala Pro Leu Val 810         820         830         840         850
AAT CCA GAG GCG AGT TCG CTG CTG CAG CAG TAT CGG AGA GAG CTG TTA GAG
Asn Pro Glu Ala Ser Ser Leu Leu Gln Gln Tyr Arg Arg Glu Leu Leu Glu
```

FIG. 1B

```
860                           870                           880                           890                           900
AGG AGC CTG CTC CGA ACG GCC GAA GGT CAG CGT GCA GTG TGT CCA TGT
Arg Ser Leu Leu Arg Thr Ala Glu Gly Gln Arg Ala Val Cys Pro Cys 910                           920                           930                           940                           950
GAG CGG TTG CCC GTG GAA GAG GAT GAG TGT CTG AAT GCC GTA AAT TTG CTG
Glu Arg Leu Pro Val Glu Glu Asp Glu Cys Leu Asn Ala Val Asn Leu Leu 960                           970                           980                           990                           1000                          1010
TTT CCT GAT CCC TGG CTA AAT GCA GCT GAA AAT GGG GGT GAT ATT TTT AAG
Phe Pro Asp Pro Trp Leu Asn Ala Ala Glu Asn Gly Gly Asp Ile Phe Lys 1020                          1030                          1040                          1050                          1060
TCT CCG GCT ATG TCT CCA GAA CCG TGG ATA GAT TTG TCT AGC TAC GAT AGC
Ser Pro Ala Met Ser Pro Glu Pro Trp Ile Asp Leu Ser Ser Tyr Asp Ser 1070                          1080                          1090                          1100                          1110
GAT GTA GAA GAG GTG ACT AGT CAC TTT TTT CTG GAT TGC CCT GAA GAC CCC
Asp Val Glu Glu Val Thr Ser His Phe Phe Leu Asp Cys Pro Glu Asp Pro 1120                          1130                          1140                          1150                          1160
AGT CGG GAG TGT TCA TCT TGT GGG TTT CAT CAG GCT CAA AGC GGA ATT CCA
Ser Arg Glu Cys Ser Ser Cys Gly Phe His Gln Ala Gln Ser Gly Ile Pro
```

FIG. IC

```
                      1170                      1180                      1190                      1200                      1210
GGC ATT ATG TGC AGT TTG TGC TAC ATG CGC CAA ACC TAC CAT TGC ATC TAT
Gly Ile Met Cys Ser Leu Cys Tyr Met Arg Gln Thr Tyr His Cys Ile Tyr 1220                 1230                 1240                 1250                 1260                 1270
A[GTAAG TACATTCTGT AAAAGAACAT CTTGGTGATT TCTAGGTATT GTTTAGGGAT
S 1280                 1290                 1300                 1310                 1320                 1330
TAACTGGGTG GAGTGATCTT AATCCGGCAT AACCAAATAC ATGTTTTCAC AG]GT CCA GTT
                                                                        er Pro Val 1340                 1350                 1360           1370              1380                 1390
TCT GAA GAG GAA ATG TGAGT CATGTTGACT TTGGCGCGC A AGAGGAAATG TGAGTCATGT
Ser Glu Glu Glu Met End 1400                 1410                 1420                 1430                 1440                 1450
TGACTTTGGC GCGCCCTACG GTGACTTTAA AGCAATTTGA GGATCACTTT TTTGTTAGTC 1460                 1470                 1480                 1490                 1500
GCTATAAAGT AGTCACGGAG TCTTTC ATG GAT CAC TTA AGC GTT CTT TTG GAT TTG
                             Met Asp His Leu Ser Val Leu Leu Asp Leu 1510                 1520                 1530                 1540                 1550
AAG CTG CTT CGC TCT ATC GTA GCG GGG GCT TCA AAT CGC ACT GGA GTG TGG
Lys Leu Leu Arg Ser Ile Val Ala Gly Ala Ser Asn Arg Thr Gly Val Trp
```

FIG. 1D

```
1560                    1570            1580                            1590            1600
AAG AGG CGG CTG TGG CTG GGA CGC CTG ACT CAA CTG GTC CAT GAT ACC TGC
Lys Arg Arg Leu Trp Leu Gly Arg Leu Thr Gln Leu Val His Asp Thr Cys 1610            1620            1630                    1640            1650
GTA GAG AAC GAG AGC ATA TTT CTC AAT TCT CTG CCA GGG AAT GAA GCT TTT
Val Glu Asn Glu Ser Ile Phe Leu Asn Ser Leu Pro Gly Asn Glu Ala Phe 1660            1670            1680                    1690            1700
TTA AGG TTG CTT CGG AGC TAT TTT GAA GTG TTT GAC GTG TTT GTG GTG
Leu Arg Leu Leu Arg Ser Gly Tyr Phe Glu Val Phe Asp Val Phe Val Val 1710            1720            1730                    1740            1750            1760
CCT GAG CTG CAT CTG GAC ACT CCG GGT CGA GTG GTC GCC GCT CTT GCT CTG
Pro Glu Leu His Leu Asp Thr Pro Gly Arg Val Val Ala Ala Leu Ala Leu 1770            1780            1790                    1800            1810
CTG GTG TTC ATC CTC AAC GAT GCT AAT TCT GCT TCT TCA GGC TTT
Leu Val Phe Ile Leu Asn Asp Ala Asn Ser Ala Ser Ser Gly Phe 1820            1830            1840                    1850            1860
GAT TCA GGT TTT CTC GTG GAC CGT CTC TGC GTG CCG CTA TGG CTG AAG GCC
Asp Ser Gly Phe Leu Val Asp Arg Leu Cys Val Pro Leu Trp Leu Lys Ala

Met Ala Glu Gly
```

FIG. IE

```
          1870      1880      1890      1900      1910
AGG GCG TTC AAG ATC ACC CAG AGC TCC AGG AGC ACT TCG CAG CCT TCC TCG
Arg Ala Phe Lys Ile Thr Gln Ser Ser Arg Ser Thr Ser Gln Pro Ser Ser
Gln Gly Val Gln Asp His Pro Glu Leu Gln Glu His Phe Ala Ala Phe Leu
          1920      1930      1940      1950      1960
TCG CCC GAC AAG ACG ACC CAG ACT ACC AGC CAG TA GAC GGG GAC AGC CCA
Ser Pro Asp Lys Thr Thr Gln Thr Thr Ser Gln Thr Ser Gln End
Val Ala Arg Gln Asp Asp Pro Asp Tyr Gln Pro Val Asp Gly Asp Ser Pro
          1970      1980      1990      2000      2010
CCC CGG GCT AGC CTG GAG GAG GCT GAA CAG AGC AGC ACT CGT TTC GAG CAC
Pro Arg Ala Ser Leu Glu Glu Ala Glu Gln Ser Ser Thr Arg Phe Glu His
          2020      2030      2040      2050      2060
ATC AGT TAC CGA GAC GTG GTG GAT GAC TTC AAT AGA TGC CAT GAT GTT TTT
Ile Ser Tyr Arg Asp Val Val Asp Asp Phe Asn Arg Cys His Asp Val Phe
          2070      2080      2090      2100      2110
TAT GAG AGG TAC AGT TTT GAG GAC ATA AAG AGC TAC GAG GCT TTG CCT GAG
Tyr Glu Arg Tyr Ser Phe Glu Asp Ile Lys Ser Tyr Glu Ala Leu Pro Glu
```

FIG. IF

```
        2130                    2140                    2150                    2160
GAC AAT TTG GAG CAG CTC ATA GCT ATG CAT GCT AAA ATC AAG CTG CTG CCC
Asp Asn Leu Glu Gln Leu Ile Ala Met His Ala Lys Ile Lys Leu Leu Pro 2170                    2180                    2190                    2200                    2210
GGT CGG GAG TAT GAG TTG ACT CAA CCT TTG AAC ATA ACA TCT TGC GCC TAT
Gly Arg Glu Tyr Glu Leu Thr Gln Pro Leu Asn Ile Thr Ser Cys Ala Tyr 2220                    2230                    2240                    2250                    2260
GTG CTC GGA AAT GGG GCT ACT ATT AGG GTA ACA GGG GAA GCC TCC CCG GCT
Val Leu Gly Asn Gly Ala Thr Ile Arg Val Thr Gly Glu Ala Ser Pro Ala 2270                    2280                    2290                    2300                    2310                    2320
ATT AGA GTG GGG GCC ATG GCC GTG GGT CCG TGT GTA ACA GGA ATG ACT GGG
Ile Arg Val Gly Ala Met Ala Val Gly Pro Cys Val Thr Gly Met Thr Gly 2330                    2340                    2350                    2360                    2370
GTG ACT TTT GTG AAT TGT AGG TTT GAG AGA GAG TCA ACA ATT AGG GGG TCC
Val Thr Phe Val Asn Cys Arg Phe Glu Arg Glu Ser Thr Ile Arg Gly Ser 2380                    2390                    2400                    2410                    2420
CTG ATA CGA GCT TCA ACT CAC GTG CTG TTT CAT GGC TGT TAT TTT ATG GGA
Leu Ile Arg Ala Ser Thr His Val Leu Phe His Gly Cys Tyr Phe Met Gly
```

FIG. 1G

```
       2430                    2440                    2450                    2460                    2470
ATT ATG GGC ACT TGT ATT GAG GTG GGG GCG GGA GCT TAC ATT CGG GGT TGT
Ile Met Gly Thr Cys Ile Glu Val Gly Ala Gly Ala Tyr Ile Arg Gly Cys 2480                    2490                    2500                    2510                    2520
GAG TTT GTG GGC TGT TAC CGG GGA ATC TGT TCT ACT TCT AAC AGA GAT ATT
Glu Phe Val Gly Cys Tyr Arg Gly Ile Cys Ser Thr Ser Asn Arg Asp Ile 2530                    2540                    2550                    2560                    2570
AAG GTG AGG CAG TGC AAC TTT GAC AAA TGC TTA CTG GGT ATT ACT TGT AAG
Lys Val Arg Gln Cys Asn Phe Asp Lys Cys Leu Leu Gly Ile Thr Cys Lys 2580                    2590                    2600                    2610                    2620
GGG GAC TAT CGT CTT TCG GGA AAT GTG TGT TCT GAG ACT TTC TGC TTT GCT
Gly Asp Tyr Arg Leu Ser Gly Asn Val Cys Ser Glu Thr Phe Cys Phe Ala 2630                    2640                    2650                    2660                    2670
CAT TTA GAG GGA GAG GGT TTG GTT AAA AAC ACA GTC AAG TCC CCT AGT
His Leu Glu Gly Glu Gly Leu Val Lys Asn Asn Thr Val Lys Ser Pro Ser 2680                    2690                    2700                    2710                    2720
CGC TGG ACC AGC GAG TCT GGC TTT TCC ATG ATA ACT TGT GCA GAC GGC AGG
Arg Trp Thr Ser Glu Ser Gly Phe Ser Met Ile Thr Cys Ala Asp Gly Arg
```

FIG. 1H

```
2730            2740            2750            2760            2770
GTT ACG CCT TTG GGT TCC CTC CAC ATT GTG GGC AAC CGT TGT AGG CGT TGG
Val Thr Pro Leu Gly Ser Leu His Ile Val Gly Asn Arg Cys Arg Arg Trp 2780            2790            2800            2810            2820            2830
CCA ACC ATG CAG GGG AAT GTG TTT ATC ATG TCT AAA CTG TAT CTG GGC AAC
Pro Thr Met Gln Gly Asn Val Phe Ile Met Ser Lys Leu Tyr Leu Gly Asn 2840            2850            2860            2870            2880
AGA ATA GGG ACT GTA GCC CTG CCC CAG TGT GCT TTC TAC AAG TCC AGC ATT
Arg Ile Gly Thr Val Ala Leu Pro Gln Cys Ala Phe Tyr Lys Ser Ser Ile 2890            2900            2910            2920            2930
TGT TTG GAG GAG AGG ACA AAC AAG CTG GTC TTG GCT TGT GCT TTT GAG
Cys Leu Glu Glu Arg Thr Asn Lys Leu Val Leu Ala Cys Ala Phe Glu 2940            2950            2960            2970            2980
AAT AAT GTA CTG GTG TAC AAA GTG TAC CTG AGA CGG GAG AGT CCC TCA ACC GTG
Asn Asn Val Leu Val Tyr Lys Val Tyr Leu Arg Arg Glu Ser Pro Ser Thr Val 2990            3000            3010            3020            3030
AAA ATG TGT GTT TGT GGG ACT TCT CAT TAT GCA AAG CCT TTG ACA CTG GCA
Lys Met Cys Val Cys Gly Thr Ser His Tyr Ala Lys Pro Leu Thr Leu Ala
```

FIG. 11

```
                                    3050                    3070                    3080
        3040
ATT ATT TCT TCA GAT ATT CGG GCT AAT CGA TAC ATG TAC ACT GTG GAC TCA
Ile Ile Ser Asp Ile Arg Ala Asn Arg Tyr Met Tyr Thr Val Asp Ser 3090                    3110                    3130                    3140
                3100                    3120
ACA GAG TTC ACT TCT GAC GAG GAT T AAAAGTGGGC GGGGCCAAGA GGGGTATAAA
Thr Glu Phe Thr Ser Asp Glu Asp End 3150    3160    3170    3180    3190            3200
TAGGTGGGGA GGTTGAGGGG AGCCGTAGTT TCTGTTTTTC CCAGACTGGG GGGGACAAC ATG
                                                                  Met 3210    3220            3230    3240            3250
GCC GAG GAA GGG CGC ATT TAT GTG CCT TAT GTA ACT GCC CGC CTG CCC AAG
Ala Glu Gly Arg Ile Tyr Val Pro Tyr Val Thr Ala Arg Leu Pro Lys 3260    3270            3280    3290            3300
TGG TCG GGT TCG GTG CAG GAT AAG ACG GGC TCG AAC ATG TTG GGG GGT GTG
Trp Ser Gly Ser Val Gln Asp Lys Thr Gly Ser Asn Met Leu Gly Gly Val 3310    3320            3330    3340            3350
GTA CTC CCT CCT AAT TCA CAG GCG CAC CGG ACG GAG ACC GTG GGC ACT GAG
Val Leu Pro Pro Asn Ser Gln Ala His Arg Thr Glu Thr Val Gly Thr Glu
```

FIG. 1J

```
      3360                      3370                      3380                      3390                      3400
GCC ACC AGA GAC AAC CTG CAC GCC GAG GGA GCG CGT CGT CCT GAG GAT CAG
Ala Thr Arg Asp Asn Leu His Ala Glu Gly Ala Arg Arg Pro Glu Asp Gln 3410                      3420                      3430                      3440                      3450
ACG CCC TAC ATG ATC TTG GTG GAG GAC TCT CTG GGA GGT TTG AAG AGG CGA
Thr Pro Tyr Met Ile Leu Val Glu Asp Ser Leu Gly Gly Leu Lys Arg Arg 3460                      3470                      3480                      3490                      3500
ATG GAC TTG CTG GAA GAA TCT AAT CAG CAG CTG GCA ACT CTC AAC CGT
Met Asp Leu Leu Glu Glu Ser Asn Gln Gln Leu Leu Ala Thr Leu Asn Arg 3510                      3520                      3530                      3540                      3550
CTC CGT ACA GGA CTC GCT GCC TAT GTG CAG GCT AAC CTT GTG GGC GGC CAA
Leu Arg Thr Gly Leu Ala Ala Tyr Val Gln Ala Asn Leu Val Gly Gly Gln 3560                      3570                      3580                      3590                      3600                      3610
GTT AAC CCC TTT GTT TAAATA AAAATACACT CATACAGTT ATTATGCTGT
Val Asn Pro Phe Val End 3620         3630         3640         3650         3660         3670
CAATAAAATT CTTTATTTTT CCTGTGATAA TACCGTGTCC AGCCGTGCTCT GTCAATAAGG 3680         3690         3700         3710         3720         3730
GTCCTATGCA TCCTGAGAAG GGCCTCATAT ACCCATGGCA TGAATATTAA GATACATGGG
```

FIG. 1K

```
       3740            3750            3760            3770            3780            3790
CATAAGGCCC TCAGAAGGGT TGAGGTAGAG CCACTGCAGA CTTTCGTGGG GAGGTAAGGT 3800            3810            3820            3830            3840            3850
GTTGTAAATA ATCCAGTCAT ACTGACTGTG CTGGGCGTGG AAGGAAAAGA TGTCTTTTAG 3860            3870            3880            3890            3900            3910
AAGAAGGGTG ATTGGCAAAG GGAGGCTCTT AGTGTAGGTA TTGATAAATC TGTTCAGTTG 3920            3930            3940            3950            3960            3970
GGAGGGATGC ATTCGGGGGC TAATAAGGTG GAGTTTAGCC TGAATCTTAA GGTTGGCAAT 3980            3990            4000            4010            4020            4030
GTTGCCCCCT AGGTCTTTGC GAGGATTCAT GTTGTGCAGT ACCACAAAAA CAGAGTAGCC 4040            4050            4060
TGTGCATTTG GGGAATTTAT CATGAAGCT T
```

FIG. 1L

```
                                              Rb BINDING SEQUENCE
Ad5       120                                              132
          IleAspLeuThrCysHisGluAlaGlyPheProProSer
           :   |   |     |   |   |   |         |   |   |
              ValAspLeuGluCysHisGluVal      LeuProProSer
BAV3       26                                               37
```

FIG. 2B

```
Ad5    82                                                                    100
       LeuAspPheSerThrProGlyArgAlaAlaAlaAlaValAlaPheLeuSerPheIle
        |   |         |   |   |   |         |   |   |   |   |   |   |
       LeuAsp      ThrProGlyArgValValAlaAlaLeuAlaLeuLeuValPheIle
BAV3    83                                                                    99
```

FIG. 3A

```
Ad5    20              26
       GlnSerSerAsnSerThrSer
        |   |   |     |   |   |
       GlnSerSerArgSerThrSer
BAV3   136             142
```

FIG. 3B

```
Ad5  150  GlnLysTyrSerIleGluGlnLeuThrThrTyrTrpLeuGlnProGlyAspAspPheGlu
            :  |    |    |    :    :    |         |    |    |    |
BAV3  74  GluArgTyrSerPheGluAspIleLysSerTyrGluAlaLeuProGluAspAsnLeuGlu

170  GluAlaIleArgValTyrAlaLysValAlaLeuArgProAspCysLysTyrLysIleSer
                |    :    |    |    :    |    |         |         :    :
       94  GlnLeuIleAlaMetHisAlaLysIleLysLeuLeuProGlyArgGluTyrGluLeuThr

190  LysLeuValAsnIleArgAsnCysCysTyrIleSerGlyAsnGlyAlaGluValGluIle
                |    |         |    |    :         |    |    |    :    :
      114  GlnProLeuAsnIleThrSerCysAlaTyrValLeuGlyAsnGlyAlaThrIleArgVal

210  AspThrGluAspArgValAlaPheArgCysSerMetIleAsnMetTrpProGlyValLeu
                |              |              :    :         |    |
      134  ThrGlyGluAlaSerProAlaIleArgValGlyAlaMetAlaValGlyProCysValThr

230  GlyMetAspGlyValValIleMetAsnValArgPheThr    GlyProAsnPheSerGly
                |    |    |    |         :    |    |    |              |
      154  GlyMetThrGlyValThrPheValAsnCysArgPheGluArgGluSerThrIleArgGly

249  ThrValPheLeuAlaAsnThrAsnLeuIleLeuHisGlyValSerPheTyr    GlyPhe
                :    :              |    |    :    |    |    |    :    :
      174  SerLeuIleArgAlaSerThrHisValLeuPheHisGlyCys    TyrPheMetGlyIle

268  AsnAsnThrCysValGluAlaTrpThrAspValArgValArgGlyCysAlaPheTyrCys
                |    |    :    |
      193  MetGlyThrCysIleGluValGlyAlaGlyAlaTyrIleArgGlyCysGluPheValGly

288  CysTrpLysGlyValValCysArgProLysSerArgAla    SerIleLysLysCysLeu
                |    :    |    :         |              :    :    |
      213  CysTyrArgGlyIle    CysSerThrSerAsnArgAspIleLysValArgGlnCysAsn

307  PheGluArgCysThrLeuGlyIleLeuSerGluGlyAsnSerArgValArgHisAsnVal
                |    :    :         |    |    |         |         |    :    |    |
      232  PheAspLysCysLeuLeuGlyIleThrCysLysGlyAspTyrArgLeuSerGlyAsnVal

327  AlaSerAspCysGlyCysPheMetLeuValLysSerValAlaValIleLysHisAsnMet
                |    :         |    |         :              :    :    |    |
      252  CysSerGluThrPheCysPheAlaHisLeuGluGlyGluGlyLeuValLysAsnAsnThr
```

FIG. 4A

```
347   Val   CysGlyAsn      CysGluAspArgAlaSerGlnMetLeuThrCysSerAsp
      |            |                    :   |  :  |  |  :  |
272   ValLysSerProSerArgTrpThrSerGluSerGlyPheSerMetIleThrCysAlaAsp

364   GlyAsnCysHisLeuLeuLysThrIleHisVal   AlaSerHisSerArgLysAlaTrp
      |  |  |  |     :  :  |  :              :        |  :        |
292   GlyArgValThrProLeuGlySerLeuHisIleValGlyAsnArgCysArgArg   Trp

383   ProValPheGluHisAsnIleLeuHisArgCysSerLeuHisLeuGlyAsnArgArgGly
      |  |  |     |  :              |     |  |  |  |           |
311   ProThrMetGlnGlyAsnValPheIleMetSerLysLeuTyrLeuGlyAsnArgIleGly

403      ValPheLeuProTyrGlnCysAsnLeuSerHisThrLysIleLeuLeuGluProGlu
         |  |  |     |  |              :  :     |  |  |
331   ThrValAlaLeuPro   GlnCysAlaPheTyrLysSerSerIleCysLeuGluGluArg

422   SerMetSerLysValAsnLeuAsnGlyValPheAspMetThrMetLysIleTrpLysVal
         :     |  :     |        |  |  :           :  :  |  |
350   AlaThrAsnLysLeuValLeuAlaCysAlaPheGluAsnAsnValLeuValTyrLysVal

442   LeuArgTyrAspGluThrArgThrArgCysArgProCysGluCysGlyGlyLysHisIle
      |  |     :              |     :     |  |  |        |
370   LeuArgArgGluSerProSerThr   ValLysMetCysValCysGlyThrSerHisTyr

462   ArgAsnGlnProValMetLeuAspVal   ThrGluGluLeuArgProAspHisLeuVal
         |  :     |     :     :  :     :     :  |        :        :
389       AlaLysProLeuThrLeuAlaIleIleSerSerAspIleArgAlaAsnArgTyrMet

481   LeuAlaCysHisArgAlaGluPheGlySerSerAspGluAspThrAspEnd
         :        :  |  |     :  |  |  |  |
408   TyrThrValAspSerThrGluPhe   ThrSerAspGluAspEnd
```

FIG. 4B

```
422  SerMetSerLysValAsnLeuAsnGlyValPheAspMetThrMetLysIleTrpLysVal
     :   ::                    ::                    :   :
350  AlaThrAsnLysLeuValLeuAlaCysAlaPheGluAsnAsnValLeuValTyrLysVal

442  LeuArgTyrAspGluThrArgCysArgProCysGluCysGlyGlyLysHisIle
                 :                   ::
370  LeuArgArgGluSerProSerThr   ValLysMetCysValCysGlyThrSerHisTyr

462  ArgAsnGlnProValMetLeuAspVal   ThrGluLeuArgProAspHisLeuVal
           :                              ::
389  AlaLysProLeuThrLeuAlaIleIleSerSerAspIleArgAlaAsnArgTyrMet

481  LeuAlaCysThrArgAlaGluPheGlySerSerAspGluAspThrAspEnd
                 ::                    :
408  TyrThrValAspSerThrGluPhe   ThrSerAspGluAspEnd
```

FIG. 4C

```
Ad5    1    MetSerThrAsnSerPheAspGlySerIleValSerSerTyrLeuThrThrArgMetPro
              |  :                           |  :           |  :
BAV3   1    MetAla    Glu    GlyArgIleTyrValProTyrValThrAlaArgLeuPro

21    ProTrpAlaGlyValArgGlnAsnValMetGlySerIleAspGlyArgProValLeu
                                       |  :
      18    LysTrpSerGlySerValGlnAspLysThrGlySerAsnMetLeuGlyGlyValValLeu

41    ProAlaAsnSerThrThrThrLeuThrTyrGluThrValSerGlyThrProLeuGluThrAla
              |  :                         |
      38    ProProAsnSerGlnAlaHisArgThrGluThrVal    GlyThrGlu    AlaThr

61    AlaSerAlaAlaAlaSerAlaAlaAlaAlaThrAlaAlaArgGlyIleValThrAspPheAla
                                                           |
      55    ArgAspAsnLeuHisAlaGluGlyAlaArg    ArgProGluAspGlnThr    Pro

81    PheLeuSerProLeuAlaSerSerAlaAlaSerArgSerSerAlaAlaArgAspAspLysLeu
              |  :                         |                 |
      72    TyrMetIle    LeuValGluAspSerLeuGlyGlyLeuLysArgArgMetAspLeuLeu

101    ThrAlaLeuLeuAlaGlnLeu    AspSerLeuThrArgGluLeuAsnValValSerGln
                                                           |
      91    GluGluSerAsnGlnGlnLeuLeuLeuAlaThrLeuAsnArg    LeuArgThr    Gly

120    GlnLeuLeuAspLeuArgGlnGlnValGlnGlnValSerAlaAlaLeuLysAlaSerProProAsnAla
                                       |  :
     108    LeuAlaAlaTyr    ValGln    AlaAsnLeuValGlyGlnValGlyGlnValAsnProPhe

140    ValEnd
              |
     125    ValEnd
```

FIG. 5

```
                              10                  20                  30                  40                  50
       C CTC ATC AAA CAA CCC GTG GGC GTG ACC CAC GAA ATG CCT CGC AAC
ORF 1    Leu Ile Lys Gln Pro Val Gly Val Thr His Glu Met Pro Arg Asn 60                  70                  80                  90                  100
       GAA GTC CTA GAA CAA CAT CTG ACC TCA CAT GGC GCT CAA ATC GCG GGC GGA
       Glu Val Leu Glu Gln His Leu Thr Ser His Gly Ala Gln Ile Ala Gly Gly 110                 120                 130                 140                 150
       GGC GCT GCG GGC GAT TAC TTT AAA AGC CCC ACT TCA GCT CGA ACC CTT ATC
       Gly Ala Ala Gly Asp Tyr Phe Lys Ser Pro Thr Ser Ala Arg Thr Leu Ile 160                 170                 180                 190                 200
       CCG CTC ACC GCC TCC TGC TTA AGA CCA GAT GGA GTC TTT CAA CTA GGA GGA
       Pro Leu Thr Ala Ser Cys Leu Arg Pro Asp Gly Val Phe Gln Leu Gly Gly 210                 220                 230                 240                 250
       GGC TCG CGT TCA TCT TTC AAC CCC CTG CAA ACA GAT TTT GCC TTC CAC GCC
       Gly Ser Arg Ser Ser Phe Asn Pro Leu Gln Thr Asp Phe Ala Phe His Ala 260                 270                 280                 290                 300
       CTG CCC TCC AGA CCG CGC CAC GGG GGC ATA GGA TCC AGG CAG TTT GTA GAG
       Leu Pro Ser Arg Pro Arg His Gly Gly Ile Gly Ser Arg Gln Phe Val Glu
```

FIG. 7A

```
310                         320                         330                         340                         350
GAA TTT GTG CCC GCC GTC TAC CTC AAC CCC TAC TCG GGA CCG CCG GAC TCT
Glu Phe Val Pro Ala Val Tyr Leu Asn Pro Tyr Ser Gly Pro Pro Asp Ser 360                         370                         380                         390                         400
TAT CCG GAC CAG TTT ATA CGC CAC TAC AAC GTG TAC AGC AAC TCT GTG AGC
Tyr Pro Asp Gln Phe Ile Arg His Tyr Asn Val Tyr Ser Asn Ser Val Ser
                                                                    ORF 2   Ala
410                         420                         430                         440                         450                         460
GGT TAT AGC T GAG ATT GTA AGA CTC TCC TAT CTG TCT CTG TGC TGC TTT TCC
Gly Tyr Ser
            Val Ile Ala  Glu Ile Val Arg Leu Ser Tyr Leu Ser Leu Cys Cys Phe Ser 470                         480                         490                         500                         510
GCT TCA AGC CCC ACA AGC ATG AAG GGG TTT CTG CTC ATC TTC AGC CTG CTT
Ala Ser Ser Pro Thr Ser Met Lys Gly Phe Leu Leu Ile Phe Ser Leu Leu
            ORF 3   Phe Met Leu Gly Pro Leu Ala Ser Met Leu Gln Gly
520                         530                         540                         550                         560
GTG CAT TGT CCC CTA ATT CAT GTT GGG ACC ATT AGC TTC TAT GCT GCA AGG
Val His Cys Pro Leu Ile His Val Gly Thr Ile Ser Phe Tyr Ala Ala Arg
```

FIG. 7B

```
                            570              580              590              600              610
                    CCC GGG TCT GAG CCT AAC GCG ACT TAT GTT TGT GAC TAT GGA AGC GAG TCA
                    Pro Gly Ser Leu Thr Asn Ala Thr Leu Met Phe Val Thr Met Glu Ala Ser Gln
                                                      ___ ___
                    Pro Gly Ser Glu Pro Asn Ala Thr Tyr Val Cys Asp Tyr Gly Ser Glu Ser
                                       ___ ___ ___
                            620              630              640              650              660
                    GAT TAC AAC CCC ACC ACG GTT CTG TGG TTG GCT CGA GAG ACC GAT GGC TCC
                    Ile Thr Thr Pro Pro Arg Phe Cys Gly Trp Leu Arg Pro Met Ala Pro
                    Asp Tyr Asn Pro Thr Thr Val Leu Trp Leu Ala Arg Glu Thr Asp Gly Ser
                        ___ ___ ___
                            670              680              690              700              710
                    TGG ATC TCT GTT CTT TTC CGT CAC AAC GGC TCC TCA ACT GCA GCC CCC GGG
                    Gly Ser Leu Phe Phe Ser Val Thr Thr Ala Pro Gln Leu Gln Pro Pro Gly
                    Trp Ile Ser Val Leu Phe Arg His Asn Gly Ser Ser Thr Ala Ala Pro Gly
                                                    ___ ___ ___
                            720              730              740              750              760
                    GTC GTC GCG CAC TTT ACT GAC CAC AAC AGC AGC ATT GTG GTG TGG CCC CAG TAT
                    Ser Ser Arg Thr Leu Leu Thr Thr Thr Ala Ala Leu Trp Cys Pro Ser Ile
                    Val Val Ala His Phe Thr Asp His Asn Ser Ser Ile Val Pro Gln Tyr
                                                      ___ ___
                            770              780              790              800              810
                    TAC CTC CTC AAC AAC TCA CTC TCT AAG CTC TGC TCA TAC CGG CAC AAC
                    Thr Ser Thr Thr His Ser Thr His Ser Leu Ser Ser Ala Ala His Thr Gly Thr Thr
                    Tyr Leu Leu Asn Asn Ser Leu Ser Lys Leu Cys Cys Ser Tyr Arg His Asn
                                ___ ___
```

FIG. 7C

```
820                         830                  840                          850                          860
GAG CGT TCT CAG TTT ACC TGC AAA CAA GCT GAC GTC CCT GAC ACC TGT CAC GAG
Ser Val Leu Ser Leu Pro Ala Asn Lys Leu Thr Ser Leu Pro Val Thr Ser

Glu Arg Ser Gln Phe Thr Cys Lys Gln Ala Asp Val Pro Thr Cys His Glu 870                  880                         890                  900                         910                  920
CCC GGC AAG CCG CTC ACC CTC CGC GTC TCC CCC GCG CTG GGA ACT GCC CAC
Pro Ala Ser Arg Ser Pro Ser Ala Ser Pro Pro Arg Trp Glu Leu Pro Thr

Pro Gly Lys Pro Leu Thr Leu Arg Val Ser Pro Ala Leu Gly Thr Ala His 930                  940                         950                  960                         970
CAA GCA GTC ACT TGG TTT TTT CAA AAT GTA CCC ATA GCT ACT GTT TAC CGA
Lys Gln Ser Leu Gly Phe Phe Lys Met Tyr Pro

Gln Ala Val Thr Trp Phe Phe Gln Asn Val Pro Ile Ala Thr Val Tyr Arg 980                  990                         1000                         1010                         1020
CCT TGG GGC AAT GTA ACT TGG TTT CCT CCC TTC ATG TGT ACC TTT AAT
Pro Trp Gly Asn Val Thr Trp Phe Pro Pro Phe Met Cys Thr Phe Asn 1030                         1040                         1050                         1060                         1070
GTC AGC CTG AAC TCC CTA CTT ATT TAC ATC CTT ATT TCT GAC AAA ACC GGG GGG
Val Ser Leu Asn Ser Leu Leu Ile Tyr Asn Phe Ser Asp Lys Thr Gly Gly
```

FIG. 7D

```
         1080                1090                1100                1110                1120
CAA TAC ACA GCT CTC ATG CAC TCC GGA CCT GCT TCC CTC TTT CAG CTC TTT
Gln Tyr Thr Ala Leu Met His Ser Gly Pro Ala Ser Leu Phe Gln Leu Phe 1130                1140                1150                1160                1170
AAG CCA ACG ACT TGT GTC ACC AAG GTG GAG GAC CCG CCG TAT GCC AAC GAC
Lys Pro Thr Thr Cys Val Thr Lys Val Glu Asp Pro Pro Tyr Ala Asn Asp 1180                1190                1200                1210                1220
CCG GCC TCG CCT GTG TGG CGC GTG CCA CTG CTT TTT GCC TTC GTC CTC TGC ACC
Pro Ala Ser Pro Val Trp Arg Pro Leu Leu Phe Ala Phe Val Leu Cys Thr 1230                1240                1250                1260                1270
GGC TGC GCG GTG TTG TTA ACC GCC TTC GGT CCA TCG ATT CTA TCC GGT ACC
Gly Cys Ala Val Leu Leu Thr Ala Phe Gly Pro Ser Ile Leu Ser Gly Thr

ORF 4   Pro Pro Ser Val His Arg Phe Tyr Pro Val Pro 1280                1290                1300                1310                1320
CGA AAG CTT ATC TCA GCC CGC TTT TGG AGT CCC GAG CCC TAT ACC ACC CTC
Glu Ser Leu Ser Gln Pro Ala Phe Gly Val Pro Ser Pro Ile Pro Pro Ser
Arg Lys Leu Ile Ser Ala Arg Phe Trp Ser Pro Glu Pro Tyr Thr Thr Leu
```

FIG. 7E

```
1330                 1340                1350                 1360                1370                 1380
CAC T AAC AGT CCC CCC ATG GAG CCA GAC GGA GTT CAT GCC GAG CAG CAG TTT
Thr Asn Ser Pro Pro Met Glu Pro Asp Gly Val His Ala Glu Gln Gln Phe
His 1390                1400                 1410                1420                 1430
ATC CTC AAT CAG ATT TCC TGC GCC AAC ACT GCC CTC CAG CGT CAA AGG GAG
Ile Leu Asn Gln Ile Ser Cys Ala Asn Thr Ala Leu Gln Arg Gln Arg Glu 1440                1450                 1460                1470                 1480
GAA CTA GCT TCC CTT GTC ATG TTG CAT GCC TGT AAG CGT GGC CTC TTT TGT
Glu Leu Ala Ser Leu Val Met Leu His Ala Cys Lys Arg Gly Leu Phe Cys
ORF 5  Leu Pro Leu Ser Cys Cys Met Pro Val Ser Val Ala Ser Phe Val 1490                1500                 1510                1520                 1530
CCA GTC AAA ACT TAC AAG CTC AGC CTC AAC GCC TCG GCC AGC GAG CAC AGC
Pro Val Lys Thr Tyr Lys Leu Ser Leu Asn Ala Ser Ala Ser Glu His Ser
Gln Ser Lys Leu Thr Ser Ser Ala Ser Thr Pro Arg Pro Ala Ser Thr Ala 1540                1550                 1560                1570                 1580
CTG CAC TTT GAA AAA ACT AGT CCC TCC CGA TTC ACC CTG GTC AAC ACT CAC GCC
Leu His Phe Glu Lys Thr Ser Pro Ser Arg Phe Thr Leu Val Asn Thr His Ala
Cys Thr Leu Lys Lys Val Pro Pro Asp Ser Pro Trp Ser Thr Leu Thr Pro
```

FIG. 7F

```
                    1590            1600            1610            1620            1630
            GGA GCT TCT GTG CGA GTG GCC CTA CAC CAG GGA GCT TCC GGC AGC ATC
            Gly Ala Ser Val Arg Val Ala Leu His Gln Gly Ala Ser Gly Ser Ile
            Glu Leu Leu Cys Glu Trp Pro Tyr Thr Arg Glu Leu Pro Ala Ala Ser 1640            1650            1660            1670            1680
            CGC TGT TCC TGT TCC CAC GCC GAG TGC CTC CCC GTC CTC CTC AAG ACC CTC
            Arg Cys Ser Cys Ser His Ala Glu Cys Leu Pro Val Leu Leu Lys Thr Leu
            Ala Val Pro Val Pro Thr Pro Ser Ala Ser Pro Ser Ser Ser Arg Pro Ser 1690            1700            1710            1720    1730    1740
            TGT GCC TTT AAC TTT TTA GAT TAG CTGAAAGCAA ATATAAAATG GTGTGCTTAC
            Cys Ala Phe Asn Phe Leu Asp
            Val Pro Leu Thr Phe 1750    1760            1770            1780            1790
            CGTAATTCTG TTTTGACTTG TGTGCTTGA TTT CTC CCC CTG CGC CGT AAT CCA GTG 1800            1810            1820            1830            1840
            CCC CTC TTC AAA ACT CTC GTA CCC TAT GCG ATT CGC ATA GGC ATA TTT TCT 1850            1860            1870            1880            1890
            AAA AGC TCT GAA GTC AAC ATC ACT CTC AAA CAC TTC TCC GTT GTA GGT TAC
```

FIG. 7G

```
1900         1910         1920         1930         1940         1950
TTT CAT CTA CAG ATA AAG TCA TCC ACC GGT T AAC ATC ATG AAG AGA AGT GTG
              ORF 6        Ser His Pro Pro Val  Asn Ile Met Lys Arg Ser Val 1960         1970         1980         1990         2000
CCC CAG GAC TTT AAT CTT GTG TAT CCG TAC AAG GCT AAG AGG CCC AAC ATC
Pro Gln Asp Phe Asn Leu Val Tyr Pro Tyr Lys Ala Lys Arg Pro Asn Ile 2010         2020         2030         2040         2050
ATG CCG CCC TTT TTT GAC CGC AAT GGC TTT GTT GAA AAC CAA GAA GCC ACG
Met Pro Pro Phe Phe Asp Arg Asn Gly Phe Val Glu Asn Gln Glu Ala Thr 2060         2070         2080         2090         2100
CTA GCC ATG CTT GTG GAA AAG CCG CTC ACG TTC GAC AAG GAA GGT GCG CTG
Leu Ala Met Leu Val Glu Lys Pro Leu Thr Phe Asp Lys Glu Gly Ala Leu 2110         2120         2130         2140         2150
ACC CTG GGC GTC GGA CGC GGC ATC CGC ATT AAC CCC GCG GGG CTT CTG GAG
Thr Leu Gly Val Gly Arg Gly Ile Arg Ile Asn Pro Ala Gly Leu Leu Glu 2160         2170         2180         2190         2200
ACA AAC GAC CTC GCG TCC GCT GTC TTC CCA CCG CTG GCC TCC GAT GAG GCC
Thr Asn Asp Leu Ala Ser Ala Val Phe Pro Pro Leu Ala Ser Asp Glu Ala
```

FIG. 7H

```
      2210                2220                2230                2240                2250
GGC AAC GTC ACG CTC AAC ATG TCT GAC GGG CTA TAT ACT AAG GAC AAC AAG
Gly Asn Val Thr Leu Asn Met Ser Asp Gly Leu Tyr Thr Lys Asp Asn Lys 2260                2270                2280                2290                2300
CTA GCT GTC AAA GTA GGT CCC GGG CTG TCC CTC GAC TCC AAT AAT GCT CTC
Leu Ala Val Lys Val Gly Pro Gly Leu Ser Leu Asp Ser Asn Asn Ala Leu 2310                2320                2330                2340                2350
CAG GTC CAC ACA GGC GAC GGG CTC ACG GTA ACC GAT GAC AAG GTG TCT CTA
Gln Val His Thr Gly Asp Gly Leu Thr Val Thr Asp Asp Lys Val Ser Leu 2360                2370                2380                2390                2400
AAT ACC CAA GCT CCC CTC TCG ACC ACC AGC GCG GGC CTC TCC CTA CTT CTG
Asn Thr Gln Ala Pro Leu Ser Thr Thr Ser Ala Gly Leu Ser Leu Leu Leu 2410                2420                2430                2440                2450                2460
GGT CCC AGC CTC CAC TTA GGT GAG GAG CTA CGA CTA ACA GTA AAC ACC GGA
Gly Pro Ser Leu His Leu Gly Glu Glu Leu Arg Leu Thr Val Asn Thr Gly 2470                2480                2490                2500                2510
GCG GGC CTC CAA ATT AGC AAT AAC GCT CTG GCC GTA AAA GGT TCA GGT
Ala Gly Leu Gln Ile Ser Asn Asn Ala Leu Ala Val Lys Val Gly Ser Gly
```

FIG. 7I

```
              2520            2530             2540            2550           2560
ATC ACC GTA GAT GCT CAA AAC CAG CTC GCT GCA TCC CTG GGG GAC GGT CTA
Ile Thr Val Asp Ala Gln Asn Gln Leu Ala Ala Ser Leu Gly Asp Gly Leu 2570            2580            2590            2600           2610
GAA AGC AGA GAT AAT AAA ACT GTC GTT AAG GCT GGG CCC GGA CTT ACA ATA
Glu Ser Arg Asp Asn Lys Thr Val Val Lys Ala Gly Pro Gly Leu Thr Ile 2620            2630             2640            2650           2660
ACT AAT CAA GCT CTT ACT GTT GCT ACC GGG AAC GGC CTT CAG GTC AAC CCG
Thr Asn Gln Ala Leu Thr Val Ala Thr Gly Asn Gly Leu Gln Val Asn Pro 2670            2680             2690            2700           2710
GAA GGG CAA CTG CAG CTA AAC ATT ACT GCC GGT CAG GGC CTC AAC TTT GCA
Glu Gly Gln Leu Gln Leu Asn Ile Thr Ala Gly Gln Gly Leu Asn Phe Ala 2720            2730             2740            2750           2760
AAC AAC AGC CTC GCC GTG GAG CTG GGC TCG GGC CTG CAT TTT CCC CCT GGC
Asn Asn Ser Leu Ala Val Glu Leu Gly Ser Gly Leu His Phe Pro Pro Gly 2770            2780             2790            2800           2810
CAA AAC CAA GTA AGC CTT TAT CCC GGA GAT GGA ATA GAC ATC CGA GAT AAT
Gln Asn Gln Val Ser Leu Tyr Pro Gly Asp Gly Ile Asp Ile Arg Asp Asn
```

FIG. 7J

```
2820              2830              2840              2850                    2860
AGG GTG ACT GTG CCC GCT GGG CCA GGC CTG AGA ATG CTC AAC CAC CAA CTT
Arg Val Thr Val Pro Ala Gly Pro Gly Leu Arg Met Leu Asn His Gln Leu 2870              2880              2890              2900              2910
GCC GTA GCT TCC GGA GAC GGT TTA GAA GTC CAC AGC GAC ACC CTC CGG TTA
Ala Val Ala Ser Gly Asp Gly Leu Glu Val His Ser Asp Thr Leu Arg Leu 2920              2930              2940              2950              2960         2970
AAG CTC TCC CAC GGC CTG ACA TTT GAA AAT GGC GCC GTA CGA GCA AAA CTA
Lys Leu Ser His Gly Leu Thr Phe Glu Asn Gly Ala Val Arg Ala Lys Leu 2980              2990              3000              3010                    3020
GGA CCA GGA CTT GGC ACA GAC GAC TCT GGT CGG TCC GTG GTT CGC ACA GGT
Gly Pro Gly Leu Gly Thr Asp Asp Ser Gly Arg Ser Val Val Arg Thr Gly 3030              3040              3050              3060              3070
CGA GGA CTT AGA GTT GCA AAC GGC CAA GTC CAG ATC TTC AGC GGA AGA GGC
Arg Gly Leu Arg Val Ala Asn Gly Gln Val Gln Ile Phe Ser Gly Arg Gly 3080              3090              3100              3110              3120
ACC GCC ATC GGC ACT GAT AGC AGC CTC ACT CTC AAC ATC CGG GCG CCC CTA
Thr Ala Ile Gly Thr Asp Ser Ser Leu Thr Leu Asn Ile Arg Ala Pro Leu
```

FIG. 7K

```
      3130            3140            3150            3160            3170
CAA TTT TCT GGA CCC GCC TTG ACT GCT AGT TTG CAA GGC AGT GGT CCG ATT
Gln Phe Ser Gly Pro Ala Leu Thr Ala Ser Leu Gln Gly Ser Gly Pro Ile 3180            3190            3200            3210            3220
ACT TAC AAC AGC AAC AAT GGC ACT TTC GGT CTC TCT ATA GGC CCC GGA ATG
Thr Tyr Asn Ser Asn Gly Thr Phe Gly Leu Ser Ile Gly Pro Gly Met 3230            3240            3250            3260            3270
TGG GTA GAC CAA CTT GTC CAG GTA AAC CCA GGC GCT GGT TTA GTC TTC
Trp Val Asp Gln Leu Val Gln Val Asn Pro Gly Ala Gly Leu Val Phe 3280            3290            3300            3310            3320
CAA GGA AAC AAC CTT GTC CCA AAC CTT GCG GAT CCG CTG GCT ATT TCC GAC
Gln Gly Asn Asn Leu Val Pro Asn Leu Ala Asp Pro Leu Ala Ile Ser Asp 3330            3340            3350            3360            3370
AGC AAA ATT AGT CTC AGT CTC GGT CCC GGC CTG ACC CAA GCT TCC AAC GCC
Ser Lys Ile Ser Leu Ser Leu Gly Pro Gly Leu Thr Gln Ala Ser Asn Ala 3380            3390            3400            3410            3420
CTG ACT TTA AGT TTA GGA AAC GGG CTT GAA TTC TCC AAT CAA GCC GTT GCT
Leu Thr Leu Ser Leu Gly Asn Gly Leu Glu Phe Ser Asn Gln Ala Val Ala
```

FIG. 7L

```
3430        3440         3450         3460        3470        3480
ATA AAA GCG GGC CGG GGC TTA CGC TTT GAG TCT TCC TCA CAA GCT TTA GAG
Ile Lys Ala Gly Arg Gly Leu Arg Phe Glu Ser Ser Ser Gln Ala Leu Glu 3490         3500         3510        3520        3530
AGC AGC CTC ACA GTC GGA AAT GGC TTA ACG CTT ACC GAT ACT GTG ATC CGC
Ser Ser Leu Thr Val Gly Asn Gly Leu Thr Leu Thr Asp Thr Val Ile Arg 3540         3550         3560        3570        3580
CCC AAC CTA GGG GAC GGC CTA GAG GTC AGA GAC AAT AAA ATC ATT GTT AAG
Pro Asn Leu Gly Asp Gly Leu Glu Val Arg Asp Asn Lys Ile Ile Val Lys 3590         3600         3610        3620        3630
CTG GGC GCG AAT CTT CGT TTT GAA AAC GGA GCC GTA ACC GCC GGC ACC GTT
Leu Gly Ala Asn Leu Arg Phe Glu Asn Gly Ala Val Thr Ala Gly Thr Val 3640         3650         3660        3670        3680
AAC CCT TCT GCG CCC GAG GCA CCA ACT CTC ACT GCA GAA CCA CCC CTC
Asn Pro Ser Ala Pro Glu Ala Pro Thr Leu Thr Ala Glu Pro Pro Leu 3690         3700         3710        3720        3730
CGA GCC TCC AAC TCC CAT CTT CAA CTG TCC CTA TCG GAG GGC TTG GTT GTG
Arg Ala Ser Asn Ser His Leu Gln Leu Ser Leu Ser Glu Gly Leu Val Val
```

FIG. 7M

```
      3740                    3750                    3760                    3770                    3780
CAT AAC AAC GCC CTT GCT CTC CAA CTG GGA GAC CTG ATG GAA GTA AAT CAG
His Asn Asn Ala Leu Ala Leu Gln Leu Gly Asp Leu Met Glu Val Asn Gln 3790                    3800                    3810                    3820                    3830
CAC GGA CTT ACT TTA AGA GTA GGC TCG GGT TTG CAA ATG CGT GAC GGC ATT
His Gly Leu Thr Leu Arg Val Gly Ser Gly Leu Gln Met Arg Asp Gly Ile 3840                    3850                    3860                    3870                    3880
TTA ACA GTT ACA CCC AGC GGC ACT CCT ATT GAG CCC AGA CTG ACT GCC CCA
Leu Thr Val Thr Pro Ser Gly Thr Pro Ile Glu Pro Arg Leu Thr Ala Pro 3890                    3900                    3910                    3920                    3930
CTG ACT CAG ACA GAG AAT GGA ATC GGG CTC GCT CTC GGC GCC GGC TTG GAA
Leu Thr Gln Thr Glu Asn Gly Ile Gly Leu Ala Leu Gly Ala Gly Leu Glu 3940                    3950                    3960                    3970                    3980                    3990
TTA GAC GAG AGC GCG CTC CAA GTA CAA GTT GGG CCC GGC ATG CGC CTG AAC
Leu Asp Glu Ser Ala Leu Gln Val Gln Val Gly Pro Gly Met Arg Leu Asn 4000                    4010                    4020                    4030                    4040
CCT GTA GAA AAG TAT GTA ACC CTG CTC CTG GGT CCT GGC CTT AGT TTT GGG
Pro Val Glu Lys Tyr Val Thr Leu Leu Leu Gly Pro Gly Leu Ser Phe Gly
```

FIG. 7N

```
                              4080                          4090
        4050         4060
CAG CCG GCC AAC AGG ACA AAT TAT GAT GTG CGC GTT TCT GTG GAG CCC CCC
Gln Pro Ala Asn Arg Thr Asn Tyr Asp Val Arg Val Ser Val Glu Pro Pro 4120                          4130
        4100         4110
ATG GTT TTC GGA CAG CGT GGT CAG CTC ACA TTT TTA GTG GGT CAC GGA CTA
Met Val Phe Gly Gln Arg Gly Gln Leu Thr Phe Leu Val Gly His Gly Leu 4170                          4180                          4190
        4150         4160
CAC ATT CAA AAT TCC AAA CTT CAG CTC AAT TTG GGA CAA GGC CTC AGA ACT
His Ile Gln Asn Ser Lys Leu Gln Leu Asn Leu Gly Gln Gly Leu Arg Thr 4220                          4230                          4240
        4200         4210
GAC CCC GTC ACC AAC CAG CTG GAA GTG CCC CTC GGT CAA GGT TTG GAA ATT
Asp Pro Val Thr Asn Gln Leu Glu Val Pro Leu Gly Gln Gly Leu Glu Ile 4270                          4280                          4290
        4250         4260
GCA GAC GAA TCC CAG GTT AGG GTT AAA TTG GGC GAT GGC CTG CAG TTT GAT
Ala Asp Glu Ser Gln Val Arg Val Lys Leu Gly Asp Gly Leu Gln Phe Asp 4320                          4330                          4340
        4300         4310
TCA CAA GCT CGC ATC ACT ACC ACT GCT CCT AAC ATG GTC ACT GAA ACT CTG TGG
Ser Gln Ala Arg Ile Thr Thr Thr Ala Pro Asn Met Val Thr Glu Thr Leu Trp
```

FIG. 70

```
4350                    4360                    4370                    4380                    4390
ACC GGA ACA GGC AGT AAT GCT AAT GTT ACA TGG CGG GGC TAC ACT GCC CCC
Thr Gly Thr Gly Ser Asn Ala Asn Val Thr Trp Arg Gly Tyr Thr Ala Pro 4400                    4410                    4420                    4430                    4440
GGC AGC AAA CTC TTT TTG AGT CTC ACT CGG TTC AGC ACT GGT CTA GTT TTA
Gly Ser Lys Leu Phe Leu Ser Leu Thr Arg Phe Ser Thr Gly Leu Val Leu 4450                    4460                    4470                    4480                    4490                    4500
GGA AAC ATG ACT ATT GAC AGC AAT GCA TCC TTT GGG CAA TAC ATT AAC GCG
Gly Asn Met Thr Ile Asp Ser Asn Ala Ser Phe Gly Gln Tyr Ile Asn Ala 4510                    4520                    4530                    4540                    4550
GGA CAC GAA CAG ATC GAA TGC TTT ATA TTG TTG GAC AAT CAG GGT AAC CTA
Gly His Glu Gln Ile Glu Cys Phe Ile Leu Leu Asp Asn Gln Gly Asn Leu 4560                    4570                    4580                    4590                    4600
AAA GAA GGA TCT AAC TTG CAA GGC ACT TGG GAA GTG AAG AAC AAC CCC TCT
Lys Glu Gly Ser Asn Leu Gln Gly Thr Trp Glu Val Lys Asn Asn Pro Ser 4610                    4620                    4630                    4640                    4650
GCT TCC AAA GCT GCT TTT TTG CCT TCC ACC GCC CTA TAC CCC ATC CTC AAC
Ala Ser Lys Ala Ala Phe Leu Pro Ser Thr Ala Leu Tyr Pro Ile Leu Asn
```

FIG. 7P

```
                    4660                    4670                    4680                    4690                    4700
               GAA AGC CGA GGG AGT CTT CCT GGA AAA AAT CTT GTG GGC ATG CAA GCC ATA
               Glu Ser Arg Gly Ser Leu Pro Gly Lys Asn Leu Val Gly Met Gln Ala Ile 4710                    4720                    4730                    4740                    4750
               CTG GGA GGC GGG GGC ACT TGC ACT GTG ATA GCC ACC CTC AAT GGC AGA CGC
               Leu Gly Gly Gly Gly Thr Cys Thr Val Ile Ala Thr Leu Asn Gly Arg Arg 4760                    4770                    4780                    4790                    4800
               AGC AAC AAC TAT CCC GCG GGC CAG TCC ATA ATT TTC GTG TGG CAA GAA TTC
               Ser Asn Asn Tyr Pro Ala Gly Gln Ser Ile Ile Phe Val Trp Gln Glu Phe 4810                    4820                    4830                    4840                    4850
               AAC ACC ATA GCC CGC CAA CCT CTG AAC CAC TCT ACA CTT ACT TTT TCT TAC
               Asn Thr Ile Ala Arg Gln Pro Leu Asn His Ser Thr Leu Thr Phe Ser Tyr 4860                    4870                    4880                    4890                    4900
               TGG ACT TA AAT AAG TTG GAA ATA AAG AGT TAA ACT GAA TGT TTA AGT GCA
               Trp Thr 4910                    4920                    4930                    4940                    4950
               ACA GAC TTT TAT TGG TTT TGG CTC ACA ACA AAT TAC AAC AGC ATA GAC AAG 4960                    4970                    4980                    4990                    5000
               TCA TAC CGG TCA AAC AAC ACA GGC TCT CGA AAA CGG GCT AAC CGC TCC AAG
```

FIG. 7Q

```
5010          5020          5030          5040          5050          5060
AAT CTG TCA CGC AGA CGA GCA AGT CCT AAA TGT TTT TTC ACT CTC TTC GGG
          5070          5080          5090          5100
GCC AAG TTC AGC ATG TAT CGG ATT TTC TGC TTA CAC CTT T
```

FIG. 7R

```
Ad2    MSKEIPTPYMWSYQPQMGLAAGAAQDYSTRINYMSAGPHMISRVNGIRAH    50
BAV3         LIKQPVVGTTHV---------------------EMPRNEVLEQH    23
       .: :      ::                               .::    :
Ad2    RNRILLEQAAITTTPRNNLNPRSWPAALVYQESPAPTTVVLPRDAQAEVQ    100
BAV3   LTSHGAQIAGGG-----AAGDYFKSPTSARTLIPLTASCL------RPDG   62
       .:  :::.:::     .  :       :  :     .     ::::
Ad2    MTNSGAQLAGGFRHRVRSPGQGITHLKIRGRGIQLNDESVSSSLGLRPDG   150
BAV3   VFQLGGGSRSSFNPLQTDFAFHALPSRPRHGGIGSRQFVEEFVPAVYLNP   112
       ::.:: ::::  : .,      :  :: ::::.  ::.::::::.:  ::
Ad2    TFQIGGAGRSSFTPRQAILTLQTSSSEPRSGGIGTLQFIEEFVPSVYFNP   200
BAV3   YSGPPDSYPDQFIRHYNVYSNSVSGYS    139
       .::::  ::::::  .     :    ::
Ad2    FSGPPGHYPDQFIPNFDAVKDSADGYD    227
```

FIG. 8A

```
BAV3   M------EPDGVHAEQQFILNQISCANTALQRQREELASLVMLHACKRGL   77
       :      :  :::   ..::     :     :  ::    ::  :: ::::.
Ad5    MTDTLDLEMDGIITEQRLL--ERRRAAAEQQRMNQELQDMVNLHQCKRGI   48
BAV3   FCPVKTYKLSLNASASEHSLHFEKSPSRFTLVNTHAGASVRVALHHQGAS   127
       :: ::  :..    .. ::  :      :  ::    :    .  .  .
Ad5    FCLVKQAKVTYDSNTTGHRLSYKLPTKRQKLVVMVGEKPITITQHSVETE   98
BAV3   GSIRCSCSHAECLPVLLKTLCAFNFLD    154
       : :      :   : :  :.:::: :
Ad5    GCIHSPCQGPEDLCTLIKTLCGLKDLIPFN    128
```

FIG. 8B

```
BAV3  - MKRSVPQD--FNLVYPYKAKR-----PNIMPPFFDRNGFVENQEATLAML  -43
        :::. :   :: ::::  .        :  .:::   :::  :        ...
Ad2   - MKRARPSEDTFNPVYPYDTETGPPTVPFLTPPFVSPNGFQESPPGVLSLR  -50

BAV3  - VEKPLTFDKE-GALTLGVGRGIRINPAGLLETNDLASAVFPPLASDEAGN  -92
         :  ::  :     : :.: .: :.. .  :: :   ..  ...
Ad2   - VSEPL--DTSHGMLALKMGSGLTLDKAGNLTSQNVTTV------------  -86

BAV3  - VTLNMSDGLYTKDNKLAVKVGPGLSLDSNNALQVHTGDGLTVTDDKVSLN  -142
             . :    ...    :... . :: :    : ::   .:..
Ad2   - -----TQPLKKTKSNISLDTSAPLTI-TSGALTVATTAPLIVTSGALSVQ  -130

BAV3  - TQAPLSTTSAGLSLLLGPSLHLGEEERLTVNTGAGLQISNNALAVKVGSG  -192
         .::::.         .:... :    . .:   :::.     .
Ad2   - SQAPLT---------------VQDSKLSIATKGPITVSDGKLALQTSAP  -164

BAV3  - ITVDAQNQLAASLGDGLESRDNKTVVKAGPGLTITNQALTVATGNGLQVN  -242
         ..     :.. .                     .  :: :::  :  .:
Ad2   - LSGSDSDTLTVT----------------------ASPPLTTATGS-LGIN  -191

BAV3  - PEGQLQLNITAGQGLNFANNSLAVELGSGLHFPPGQNQVSLYPGDGIDIR  -292
         : .  ..:          :  . .                :
Ad2   - MEDPIYVN----------NGKIGIKISGPLQVAQ---------------  -215

BAV3  - DNRVTVPAGPGLRMLNHQLAVASGDGLEVHSDTLRLKLSHGLTFENGAVR  -342
                                     ::::: .   :..:  :.  ...
Ad2   - -------------------------------NSDTLTVVTGPGVTVEQNSLR  -236
```

FIG. 8C-1

```
BAV3  - AKLGPGLGTDDSGRSVVRTGRGLRVANGQVQIFSGRGTAIGTDSSLTLNI  -392
        .:.       .: :      ..:: :..:. :     .             . . . :.
Ad2   - TKVAGAIGYDSSNNMEIKTGGMRINNNL--LILDVDYPFDAQTKLRLKL  -284

BAV3  - RAPLQFSGPALTASLQGSGPITYNSNNGTFGLSIGPGMWVDQNRLQVNPG  -442
                          : ::. :.                        : ..:
Ad2   - ---------------GQGPLYINASHN---------------LDINYN  -302

BAV3  - AGLVFQGNNLVPNLADPLAISDSKISLSLGPGLTQASNALTLSLGNGLEF  -492
        ::                  :      . .:           :: :
Ad2   - RGLYL------------FNASNNTKKLEVSIKKSS---------GLNF  -329

BAV3  - SNQAVAIKAGRGLRFESSSQALESSLTVGNGLTLTDTVIRPNLGDGLEVR  -542
        : :.::  ::.::  :... .
Ad2   - DNTAIAINAGKGLEFDTNT------------------------------  -348

BAV3  - DNKIIVKLGANLRFENGAVTAGTVNPSAPEAPPTLTAEPPLRASNSHLQL  -592

Ad2   - -------------------------------------------------  -348

BAV3  - SLSEGLVVHNNALALQLGDGMEVQHGLTLRVGSGLQMRDGILTVTPSGT   -642
                       .   ..:        ..:::.             ..
Ad2   - ---------------SESPDIN--PIKTKIGSGID-------YNENGA   -372

BAV3  - PIEPRLTAPLTQTENGIGLALGAGLELDESALQVKVGPGMRLNPVEKYVT  -692
             :                      :::::  : :
Ad2   - MIT---------------KLGAGLSFDNSG------------------  -387
```

FIG. 8C-2

```
BAV3  - LLLGPGLSFGQPANRTNYDVRVSVEPPMVFGQRGQLTFLVGHGLHIQNSK  -742
           .. :            : ....                       : .
Ad2   - -----AITIG-----NKNDDKLTLWTTPDPSP---------------NCR -412

BAV3  - LQLNLGQGLRTDPVTNQLEVPLGQGLEIADESQVRVKLGDGLQFDSQARI  -792
           .                            .      .:       ::
Ad2   - IHSD---------------------NDCKFTLVLT---KCGSQVLA    -434

BAV3  - TTAPNMVTETLWTGTGSNANVTWRGYTAPGSKLFLSLTRFSTGLVLGNMT  -842
        ::    :.   ::  : :.                  .::       :...:  .
Ad2   - TVAALAVSGDLSSMTGTVASVS---------IFLRFDQ--NGVLMENSS  -472

BAV3  - IDSNASFGQYINAGHEQIECFILLDNQGNLKEGSNLQGTWEVKNNPSASK  -892
        .                        : ..         :: .
Ad2   - LKKHY--------------------WNFRNGNS------TNANPYTNA  -494

BAV3  - AAFLPSTALYPILNESRGSLPGKNLVGMQAILGGGGTCTVIA-TLNGRRS  -941
        :.:     ::     .             :.:.         ... ::::
Ad2   - VGFMPNLLAYP---KTQSQTAKNNIVSQVYLHGDKTKPMILTITLNGTSE  -541

BAV3  - NNYPAGQSII---FVWQ-EFNTIARQPLNHSTLTFSYWT  -976
        ..          : :   :    : :::.  .
Ad2   - STETSEVSTYSMSFTWSWESGKYTTETFATNSYTFSYIAQE  -582
```

FIG. 8C-3

SEQUENCE LISTING

```
<160> NUMBER OF SEQ ID NOS: 34

<210> SEQ ID NO 1
<211> LENGTH: 4060
<212> TYPE: DNA
<213> ORGANISM: Bovine adenovirus type 3
<220> FEATURE:
<221> NAME/KEY: CDS
<222> LOCATION: join (606..1215, 1323..1345)

<400> SEQUENCE: 1
catcatcaat aatctacagt acactgatgg cagcggtcca actgccaatc atttttgcca      60
cgtcatttat gacgcaacga cggcgagcgt ggcgtgctga cgtaactgtg gggcggagcg     120
cgtcgcggag gcggcggcgc tgggcggggc tgagggcggc gggggcggcg cgcggggcgg     180
cgcgcggggc ggggcgaggg gcggagttcc gcacccgcta cgtcattttc agacatttt     240 tagcaaattt gcgccttttg caagcatttt tctcacattt caggtattta gagggcggat     300
ttttggtgtt cgtacttccg tgtcacatag ttcactgtca atcttcatta cggcttagac     360
aaattttcgg cgtcttttcc gggtttatgt ccccggtcac ctttatgact gtgtgaaaca     420
cacctgccca ttgtttaccc ttggtcagtt ttttcgtctc ctagggtggg aacatcaaga     480
acaaatttgc cgagtaattg tgcaccttt tccgcgttag gactgcgttt cacacgtaga     540 cagactttt ctcattttct cacactccgt cgtccgcttc agagctctgc gtcttcgctg     600
```

| | |
|---|---|
| ccacc atg aag tac ctg gtc ctc gtt ctc aac gac ggc atg agt cga att<br>      Met Lys Tyr Leu Val Leu Val Leu Asn Asp Gly Met Ser Arg Ile<br>       1              5               10              15 | 650 |
| gaa aaa gct ctc ctg tgc agc gat ggt gag gtg gat tta gag tgt cat<br>Glu Lys Ala Leu Leu Cys Ser Asp Gly Glu Val Asp Leu Glu Cys His<br>                20                 25                 30 | 698 |
| gag gta ctt ccc cct tct ccc gcg cct gtc ccc gct tct gtg tca ccc<br>Glu Val Leu Pro Pro Ser Pro Ala Pro Val Pro Ala Ser Val Ser Pro<br>           35                 40                 45 | 746 |
| gtg agg agt cct cct cct ctg tct ccg gtg ttt cct ccg tct ccg cca<br>Val Arg Ser Pro Pro Pro Leu Ser Pro Val Phe Pro Pro Ser Pro Pro<br>      50                 55                 60 | 794 |
| gcc ccg ctt gtg aat cca gag gcg agt tcg ctg ctg cag cag tat cgg<br>Ala Pro Leu Val Asn Pro Glu Ala Ser Ser Leu Leu Gln Gln Tyr Arg<br>     65                 70                 75 | 842 |
| aga gag ctg tta gag agg agc ctg ctc cga acg gcc gaa ggt cag cag<br>Arg Glu Leu Leu Glu Arg Ser Leu Leu Arg Thr Ala Glu Gly Gln Gln<br>80                 85                 90                 95 | 890 |
| cgt gca gtg tgt cca tgt gag cgg ttg ccc gtg gaa gag gat gag tgt<br>Arg Ala Val Cys Pro Cys Glu Arg Leu Pro Val Glu Glu Asp Glu Cys<br>               100               105               110 | 938 |
| ctg aat gcc gta aat ttg ctg ttt cct gat ccc tgg cta aat gca gct<br>Leu Asn Ala Val Asn Leu Leu Phe Pro Asp Pro Trp Leu Asn Ala Ala<br>           115                 120                 125 | 986 |
| gaa aat ggg ggt gat att ttt aag tct ccg gct atg tct cca gaa ccg<br>Glu Asn Gly Gly Asp Ile Phe Lys Ser Pro Ala Met Ser Pro Glu Pro<br>      130                 135                 140 | 1034 |
| tgg ata gat ttg tct agc tac gat agc gat gta gaa gag gtg act agt<br>Trp Ile Asp Leu Ser Ser Tyr Asp Ser Asp Val Glu Glu Val Thr Ser<br>    145                 150                 155 | 1082 |
| cac ttt ttt ctg gat tgc cct gaa gac ccc agt cgg gag tgt tca tct<br>His Phe Phe Leu Asp Cys Pro Glu Asp Pro Ser Arg Glu Cys Ser Ser<br>160               165                 170                 175 | 1130 |
| tgt ggg ttt cat cag gct caa agc gga att cca ggc att atg tgc agt<br>Cys Gly Phe His Gln Ala Gln Ser Gly Ile Pro Gly Ile Met Cys Ser<br>               180               185               190 | 1178 |
| ttg tgc tac atg cgc caa acc tac cat tgc atc tat agtaagtaca<br>Leu Cys Tyr Met Arg Gln Thr Tyr His Cys Ile Tyr<br>         195                 200 | 1224 |
| ttctgtaaaa gaacatcttg gtgatttcta ggtattgttt agggattaac tgggtggagt | 1284 |
| gatcttaatc cggcataacc aaatacatgt tttcacag gt cca gtt tct gaa gag<br>                                                    Ser Pro Val Ser Glu Glu<br>                                                             205 | 1339 |
| gaa atg tgagtcatgt tgactttggc gcgcaagagg aaatgtgagt catgttgact<br>Glu Met<br>210 | 1395 |
| ttggcgcgcc ctacggtgac tttaaagcaa tttgaggatc actttttttgt tagtcgctat | 1455 |
| aaagtagtca cggagtcttc atggatcact taagcgttct tttggatttg aagctgcttc | 1515 |
| gctctatcgt agcgggggct tcaaatcgca ctggagtgtg aagaggcgg ctgtggctgg | 1575 |
| gacgcctgac tcaactggtc catgatacct gcgtagagaa cgagagcata tttctcaatt | 1635 |
| ctctgccagg gaatgaagct tttttaaggt tgcttcggag cggctatttt gaagtgtttg | 1695 |
| acgtgtttgt ggtgcctgag ctgcatctgg acactccggg tcgagtggtc gccgctcttg | 1755 |
| ctctgctggt gttcatcctc aacgatttag acgctaattc tgcttcttca ggctttgatt | 1815 |
| caggttttct cgtggaccgt tctgcgtgc cgctatggct gaaggccagg gcgttcaaga | 1875 |
| tcacccagag ctccaggagc acttcgcagc cttcctcgtc gcccgacaag acgacccaga | 1935 |

-continued

```
ctaccagcca gtagacgggg acagcccacc ccgggctagc ctggaggagg ctgaacagag    1995
cagcactcgt ttcgagcaca tcagttaccg agacgtggtg gatgacttca atagatgcca    2055
tgatgttttt tatgagaggt acagttttga ggacataaag agctacgagg ctttgcctga    2115
ggacaatttg gagcagctca tagctatgca tgctaaaatc aagctgctgc ccggtcggga    2175
gtatgagttg actcaacctt tgaacataac atcttgcgcc tatgtgctcg gaaatggggc    2235
tactattagg gtaacagggg aagcctcccc ggctattaga gtgggggcca tggccgtggg    2295
tccgtgtgta acaggaatga ctgggggtgac ttttgtgaat tgtaggtttg agagagagtc   2355
aacaattagg gggtccctga tacgagcttc aactcacgtg ctgtttcatg gctgttattt    2415
tatgggaatt atgggcactt gtattgaggt ggggcggga gcttacattc ggggttgtga     2475
gtttgtgggc tgttaccggg gaatctgttc tacttctaac agagatatta aggtgaggca    2535
gtgcaacttt gacaaatgct tactgggtat tacttgtaag ggggactatc gtctttcggg    2595
aaatgtgtgt tctgagactt tctgcttttgc tcatttagag ggagagggtt tggttaaaaa   2655
caacacagtc aagtcccta gtcgctggac cagcgagtct ggcttttcca tgataacttg     2715
tgcagacgga agggttacgc ctttgggttc cctccacatt gtgggcaacc gttgtaggcg    2775
ttggccaacc atgcagggga atgtgtttat catgtctaaa ctgtatctgg caacagaat     2835 agggactgta gccctgcccc agtgtgcttt ctacaagtcc agcatttgtt tggaggagag    2895
ggcgacaaac aagctggtct tggcttgtgc ttttgagaat aatgtactgg tgtacaaagt    2955
gctgagacgg gagagtccct caaccgtgaa aatgtgtgtt tgtgggactt ctcattatgc    3015
aaagcctttg acactggcaa ttatttcttc agatattcgg gctaatcgat acatgtacac    3075
tgtggactca acagagttca cttctgacga ggattaaaag tgggcggggc caagaggggt    3135
ataaataggt ggggaggttg aggggagccg tagtttctgt ttttcccaga ctggggggga   3195
caacatggcc gaggaagggc gcatttatgt gccttatgta actgcccgcc tgcccaagtg    3255
gtcgggttcg gtgcaggata agacgggctc gaacatgttg gggggtgtgg tactccctcc    3315
taattcacag gcgcaccgga cggagaccgt gggcactgag gccaccagag acaacctgca    3375
cgccgaggga gcgcgtcgtc ctgaggatca gacgccctac atgatcttgg tggaggactc    3435
tctgggaggt ttgaagaggc gaatggactt gctggaagaa tctaatcagc agctgctggc    3495
aactctcaac cgtctccgta caggactcgc tgcctatgtg caggctaacc ttgtgggcgg    3555
ccaagttaac ccctttgttt aaataaaaat acactcatac agtttattat gctgtcaata    3615
aaattcttta ttttcctgt gataataccg tgtccagcgt gctctgtcaa taagggtcct     3675
atgcatcctg agaagggcct catatacccca tggcatgaat attaagatac atgggcataa   3735
ggccctcaga agggttgagg tagagccact gcagactttc gtggggaggt aaggtgttgt    3795
aaataatcca gtcatactga ctgtgctggg cgtggaagga aaagatgtct tttagaagaa    3855
gggtgattgg caaagggagg ctcttagtgt aggtattgat aaatctgttc agttgggagg    3915
gatgcattcg ggggctaata aggtggagtt tagcctgaat cttaaggttg caatgttgc     3975 ccctaggtc tttgcgagga ttcatgttgt gcagtaccac aaaaacagag tagcctgtgc     4035
atttggggaa tttatcatga agctt                                          4060
```

<210> SEQ ID NO 2
<211> LENGTH: 211
<212> TYPE: PRT
<213> ORGANISM: Bovine adenovirus type 3

<400> SEQUENCE: 2

-continued

```
Met Lys Tyr Leu Val Leu Val Leu Asn Asp Gly Met Ser Arg Ile Glu
 1               5                  10                  15

Lys Ala Leu Leu Cys Ser Asp Gly Glu Val Asp Leu Glu Cys His Glu
            20                  25                  30

Val Leu Pro Ser Pro Ala Pro Val Pro Ala Ser Val Ser Pro Val
        35                  40                  45

Arg Ser Pro Pro Pro Leu Ser Pro Val Phe Pro Ser Pro Pro Ala
    50                  55                  60

Pro Leu Val Asn Pro Glu Ala Ser Ser Leu Leu Gln Gln Tyr Arg Arg
 65                  70                  75                  80

Glu Leu Leu Glu Arg Ser Leu Leu Arg Thr Ala Glu Gly Gln Gln Arg
                85                  90                  95

Ala Val Cys Pro Cys Glu Arg Leu Pro Val Glu Glu Asp Glu Cys Leu
            100                 105                 110

Asn Ala Val Asn Leu Leu Phe Pro Asp Pro Trp Leu Asn Ala Ala Glu
            115                 120                 125

Asn Gly Gly Asp Ile Phe Lys Ser Pro Ala Met Ser Pro Glu Pro Trp
130                 135                 140

Ile Asp Leu Ser Ser Tyr Asp Ser Asp Val Glu Val Thr Ser His
145                 150                 155                 160

Phe Phe Leu Asp Cys Pro Glu Asp Pro Ser Arg Glu Cys Ser Ser Cys
                165                 170                 175

Gly Phe His Gln Ala Gln Ser Gly Ile Pro Gly Ile Met Cys Ser Leu
            180                 185                 190

Cys Tyr Met Arg Gln Thr Tyr His Cys Ile Tyr Ser Pro Val Ser Glu
            195                 200                 205

Glu Glu Met
210

<210> SEQ ID NO 3
<211> LENGTH: 4060
<212> TYPE: DNA
<213> ORGANISM: Bovine adenovirus type 3
<220> FEATURE:
<221> NAME/KEY: CDS
<222> LOCATION: (1476)..(1946)

<400> SEQUENCE: 3
catcatcaat aatctacagt acactgatgg cagcggtcca actgccaatc attttttgcca    60
cgtcatttat gacgcaacga cggcgagcgt ggcgtgctga cgtaactgtg gggcggagcg   120
cgtcgcggag gcggcggcgc tgggcggggc tgagggcggc ggggcggcg cgcggggcgg   180
cgcgcggggc gggcgagggg gcggagttcc gcacccgcta cgtcattttc agacatttttt   240
tagcaaattt gcgccttttg caagcatttt tctcacattt caggtattta gagggcggat   300
ttttggtgtt cgtacttccg tgtcacatag ttcactgtca atcttcatta cggcttagac   360
aaattttcgg cgtcttttcc gggtttatgt ccccggtcac ctttatgact gtgtgaaaca   420
cacctgccca ttgtttaccc ttggtcagtt ttttcgtctc ctagggtggg aacatcaaga   480
acaaatttgc cgagtaattg tgcacctttt tccgcgttag gactgcgttt cacacgtaga   540
cagacttttt ctcatttttct cactccgt cgtccgcttc agagctctgc gtcttcgctg   600
ccaccatgaa gtacctggtc ctcgttctca acgacggcat gagtcgaatt gaaaaagctc   660
tcctgtgcag cgatggtgag gtggatttag agtgtcatga ggtacttccc ccttctcccg   720
cgcctgtccc cgcttctgtg tcacccgtga ggagtcctcc tcctctgtct ccggtgtttc   780
ctccgtctcc gccagccccg cttgtgaatc cagaggcgag ttcgctgctg cagcagtatc   840
```

```
ggagagagct gttagagagg agcctgctcc gaacggccga aggtcagcag cgtgcagtgt    900
gtccatgtga gcggttgccc gtggaagagg atgagtgtct gaatgccgta aatttgctgt    960
ttcctgatcc ctggctaaat gcagctgaaa atggggtga tattttaag tctccggcta    1020 tgtctccaga accgtggata gatttgtcta gctacgatag cgatgtagaa gaggtgacta   1080 gtcactttt tctggattgc cctgaagacc ccagtcggga gtgttcatct tgtgggtttc    1140
atcaggctca aagcggaatt ccaggcatta tgtgcagttt tgctacatg cgccaaacct    1200 accattgcat ctatagtaag tacattctgt aaaagaacat cttggtgatt tctaggtatt    1260
gtttagggat taactgggtg gagtgatctt aatccggcat aaccaaatac atgttttcac    1320
aggtccagtt tctgaagagg aaatgtgagt catgttgact ttggcgcgca agaggaaatg    1380
tgagtcatgt tgactttggc gcgcctacg gtgactttaa agcaatttga ggatcacttt    1440
tttgttagtc gctataaagt agtcacggag tcttc atg gat cac tta agc gtt      1493
                                      Met Asp His Leu Ser Val
                                       1               5 ctt ttg gat ttg aag ctg ctt cgc tct atc gta gcg ggg gct tca aat    1541
Leu Leu Asp Leu Lys Leu Leu Arg Ser Ile Val Ala Gly Ala Ser Asn
         10                  15                  20 cgc act gga gtg tgg aag agg cgg ctg tgg ctg gga cgc ctg act caa    1589
Arg Thr Gly Val Trp Lys Arg Arg Leu Trp Leu Gly Arg Leu Thr Gln
     25                  30                  35 ctg gtc cat gat acc tgc gta gag aac gag agc ata ttt ctc aat tct    1637
Leu Val His Asp Thr Cys Val Glu Asn Glu Ser Ile Phe Leu Asn Ser
 40                  45                  50 ctg cca ggg aat gaa gct ttt tta agg ttg ctt cgg agc ggc tat ttt    1685
Leu Pro Gly Asn Glu Ala Phe Leu Arg Leu Leu Arg Ser Gly Tyr Phe
 55                  60                  65                  70 gaa gtg ttt gac gtg ttt gtg gtg cct gag ctg cat ctg gac act ccg    1733
Glu Val Phe Asp Val Phe Val Val Pro Glu Leu His Leu Asp Thr Pro
                 75                  80                  85 ggt cga gtg gtc gcc gct ctt gct ctg ctg gtg ttc atc ctc aac gat    1781
Gly Arg Val Val Ala Ala Leu Ala Leu Leu Val Phe Ile Leu Asn Asp
         90                  95                 100 tta gac gct aat tct gct tct tca ggc ttt gat tca ggt ttt ctc gtg    1829
Leu Asp Ala Asn Ser Ala Ser Ser Gly Phe Asp Ser Gly Phe Leu Val
        105                 110                 115 gac cgt ctc tgc gtg ccg cta tgg ctg aag gcc agg gcg ttc aag atc    1877
Asp Arg Leu Cys Val Pro Leu Trp Leu Lys Ala Arg Ala Phe Lys Ile
120                 125                 130 acc cag agc tcc agg agc act tcg cag cct tcc tcg tcg ccc gac aag    1925
Thr Gln Ser Ser Arg Ser Thr Ser Gln Pro Ser Ser Ser Pro Asp Lys
135                 140                 145                 150 acg acc cag act acc agc cag tagacgggga cagcccaccc cgggctagcc         1976
Thr Thr Gln Thr Thr Ser Gln
                155 tggaggaggc tgaacagagc agcactcgtt tcgagcacat cagttaccga gacgtggtgg    2036 atgacttcaa tagatgccat gatgttttt atgagaggta cagttttgag gacataaaga    2096 gctacgaggc tttgcctgag acaatttgg agcagctcat agctatgcat gctaaaatca    2156 agctgctgcc cggtcgggag tatgagttga ctcaaccttt gaacataaca tcttgcgcct    2216 atgtgctcgg aaatggggct actattaggg taacagggga agcctccccg gctattagag    2276 tgggggccat ggccgtgggt ccgtgtgtaa caggaatgac tgggtgact tttgtgaatt    2336 gtaggtttga gagagagtca acaattaggg ggtccctgat acgagcttca actcacgtgc    2396 tgtttcatgg ctgttatttt atgggaatta tgggcacttg tattgaggtg ggggcgggag    2456
```

-continued

```
cttacattcg gggttgtgag tttgtgggct gttaccgggg aatctgttct acttctaaca    2516
gagatattaa ggtgaggcag tgcaactttg acaaatgctt actgggtatt acttgtaagg    2576
gggactatcg tctttcggga aatgtgtgtt ctgagacttt ctgctttgct catttagagg    2636
gagagggttt ggttaaaaac aacacagtca agtccectag tcgctggacc agcgagtctg    2696
gcttttccat gataacttgt gcagacggca gggttacgcc tttgggttcc ctccacattg    2756
tgggcaaccg ttgtaggcgt tggccaacca tgcagggaa tgtgtttatc atgtctaaac     2816
tgtatctggg caacagaata gggactgtag ccctgcccca gtgtgctttc tacaagtcca    2876
gcatttgttt ggaggagagg gcgacaaaca agctggtctt ggcttgtgct tttgagaata    2936
atgtactggt gtacaaagtg ctgagacggg agagtccctc aaccgtgaaa atgtgtgttt    2996
gtgggacttc tcattatgca aagcctttga cactggcaat tatttcttca gatattcggg    3056
ctaatcgata catgtacact gtggactcaa cagattcac ttctgacgag gattaaaagt     3116
gggcggggcc aagaggggta taaataggtg gggaggttga ggggagccgt agtttctgtt    3176
tttcccagac tggggggac aacatggccg aggaagggcg catttatgtg ccttatgtaa     3236
ctgcccgcct gcccaagtgg tcgggttcgg tgcaggataa cacgggctcg aacatgttgg    3296
ggggtgtggt actccctcct aattcacagg cgcaccggac ggagaccgtg ggcactgagg    3356
ccaccagaga caacctgcac gccgagggag cgcgtcgtcc tgaggatcag acgccctaca    3416
tgatcttggt ggaggactct ctgggaggtt tgaagaggcg aatggacttg ctggaagaat    3476
ctaatcagca gctgctggca actctcaacc gtctccgtac aggactcgct gcctatgtgc    3536
aggctaacct tgtgggcggc caagttaacc cctttgttta ataaaaata cactcataca     3596 gtttattatg ctgtcaataa aattctttat ttttcctgtg ataataccgt gtccagcgtg    3656
ctctgtcaat aagggtccta tgcatcctga gaagggcctc atatacccat ggcatgaata    3716
ttaagataca tgggcataag gccctcagaa gggttgaggt agagccactg cagactttcg    3776
tggggaggta agtgttgta aataatccag tcatactgac tgtgctgggc gtggaaggaa     3836
aagatgtctt ttagaagaag ggtgattggc aaagggaggc tcttagtgta ggtattgata    3896
aatctgttca gttgggaggg atgcattcgg gggctaataa ggtggagttt agcctgaatc    3956
ttaaggttgg caatgttgcc ccctaggtct ttgcgaggat tcatgttgtg cagtaccaca    4016
aaaacagagt agcctgtgca tttgggggaat ttatcatgaa gctt                    4060
```

<210> SEQ ID NO 4
<211> LENGTH: 157
<212> TYPE: PRT
<213> ORGANISM: Bovine adenovirus type 3

<400> SEQUENCE: 4

Met Asp His Leu Ser Val Leu Leu Asp Leu Lys Leu Leu Arg Ser Ile
1               5                   10                  15

Val Ala Gly Ala Ser Asn Arg Thr Gly Val Trp Lys Arg Arg Leu Trp
                20                  25                  30

Leu Gly Arg Leu Thr Gln Leu Val His Asp Thr Cys Val Glu Asn Glu
            35                  40                  45

Ser Ile Phe Leu Asn Ser Leu Pro Gly Asn Glu Ala Phe Leu Arg Leu
        50                  55                  60

Leu Arg Ser Gly Tyr Phe Glu Val Phe Asp Val Phe Val Val Pro Glu
65                  70                  75                  80

Leu His Leu Asp Thr Pro Gly Arg Val Val Ala Ala Leu Ala Leu Leu
                85                  90                  95

-continued

```
Val Phe Ile Leu Asn Asp Leu Asp Ala Asn Ser Ala Ser Ser Gly Phe
                100                 105                 110

Asp Ser Gly Phe Leu Val Asp Arg Leu Cys Val Pro Leu Trp Leu Lys
            115                 120                 125

Ala Arg Ala Phe Lys Ile Thr Gln Ser Ser Arg Ser Thr Ser Gln Pro
        130                 135                 140

Ser Ser Ser Pro Asp Lys Thr Thr Gln Thr Thr Ser Gln
145                 150                 155

<210> SEQ ID NO 5
<211> LENGTH: 4060
<212> TYPE: DNA
<213> ORGANISM: Bovine adenovirus type 3
<220> FEATURE:
<221> NAME/KEY: CDS
<222> LOCATION: (1850)..(3109)

<400> SEQUENCE: 5
```

| | | | | | |
|---|---|---|---|---|---|
| catcatcaat | aatctacagt | acactgatgg | cagcggtcca | actgccaatc | attttttgcca | 60 |
| cgtcatttat | gacgcaacga | cggcgagcgt | ggcgtgctga | cgtaactgtg | gggcggagcg | 120 |
| cgtcgcggag | gcggcggcgc | tgggcggggc | tgagggcggc | gggggcggcg | cgcggggcgg | 180 |
| cgcgcgggc | gggcgaggg | gcggagttcc | gcacccgcta | cgtcattttc | agacattttt | 240 |
| tagcaaattt | gcgccttttg | caagcatttt | tctcacattt | caggtattta | gagggcggat | 300 |
| ttttggtgtt | cgtacttccg | tgtcacatag | ttcactgtca | atcttcatta | cggcttagac | 360 |
| aaattttcgg | cgtctttttcc | gggtttatgt | ccccggtcac | ctttatgact | gtgtgaaaca | 420 |
| cacctgccca | ttgtttaccc | ttggtcagtt | ttttcgtctc | ctagggtggg | aacatcaaga | 480 |
| acaaatttgc | cgagtaattg | tgcaccttt | tccgcgttag | gactgcgttt | cacacgtaga | 540 |
| cagactttt | ctcattttct | cacactccgt | cgtccgcttc | agagctctgc | gtcttcgctg | 600 |
| ccaccatgaa | gtacctggtc | ctcgttctca | acgacggcat | gagtcgaatt | gaaaaagctc | 660 |
| tcctgtgcag | cgatggtgag | gtggatttag | agtgtcatga | ggtacttccc | ccttctcccg | 720 |
| cgcctgtccc | cgcttctgtg | tcacccgtga | ggagtcctcc | tcctctgtct | ccggtgtttc | 780 |
| ctccgtctcc | gccagccccg | cttgtgaatc | cagaggcgag | ttcgctgctg | cagcagtatc | 840 |
| ggagagagct | gttagagagg | agcctgctcc | gaacggccga | aggtcagcag | cgtgcagtgt | 900 |
| gtccatgtga | gcggttgccc | gtggaagagg | atgagtgtct | gaatgccgta | aatttgctgt | 960 |
| ttcctgatcc | ctggctaaat | gcagctgaaa | atgggggtga | tattttttaag | tctccggcta | 1020 |
| tgtctccaga | accgtggata | gatttgtcta | gctacgatag | cgatgtagaa | gaggtgacta | 1080 |
| gtcacttttt | tctggattgc | cctgaagacc | ccagtcggga | gtgttcatct | tgtgggtttc | 1140 |
| atcaggctca | aagcggaatt | ccaggcatta | tgtgcagttt | gtgctacatg | cgccaaacct | 1200 |
| accattgcat | ctatagtaag | tacattctgt | aaaagaacat | cttggtgatt | tctaggtatt | 1260 |
| gtttagggat | taactgggtg | gagtgatctt | aatccggcat | aaccaaatac | atgttttcac | 1320 |
| aggtccagtt | tctgaagagg | aaatgtgagt | catgttgact | ttggcgcgca | agaggaaatg | 1380 |
| tgagtcatgt | tgactttggc | gcgccctacg | gtgactttaa | agcaatttga | ggatcacttt | 1440 |
| tttgttagtc | gctataaagt | agtcacggag | tcttcatgga | tcacttaagc | gttcttttgg | 1500 |
| atttgaagct | gcttcgctct | atcgtagcgg | gggcttcaaa | tcgcactgga | gtgtggaaga | 1560 |
| ggcggctgtg | gctgggacgc | ctgactcaac | tggtccatga | tacctgcgta | gagaacgaga | 1620 |
| gcatatttct | caattctctg | ccagggaatg | aagctttttt | aaggttgctt | cggagcggct | 1680 |

-continued

```
attttgaagt gtttgacgtg tttgtggtgc ctgagctgca tctggacact ccgggtcgag   1740
tggtcgccgc tcttgctctg ctggtgttca tcctcaacga tttagacgct aattctgctt   1800
cttcaggctt tgattcaggt tttctcgtgg accgtctctg cgtgccgct atg gct gaa   1858
                                                     Met Ala Glu
                                                       1 ggc cag ggc gtt caa gat cac cca gag ctc cag gag cac ttc gca gcc   1906
Gly Gln Gly Val Gln Asp His Pro Glu Leu Gln Glu His Phe Ala Ala
     5                  10                  15 ttc ctc gtc gcc cga caa gac gac cca gac tac cag cca gta gac ggg   1954
Phe Leu Val Ala Arg Gln Asp Asp Pro Asp Tyr Gln Pro Val Asp Gly
 20                  25                  30                  35 gac agc cca ccc cgg gct agc ctg gag gag gct gaa cag agc agc act   2002
Asp Ser Pro Pro Arg Ala Ser Leu Glu Glu Ala Glu Gln Ser Ser Thr
                 40                  45                  50 cgt ttc gag cac atc agt tac cga gac gtg gtg gat gac ttc aat aga   2050
Arg Phe Glu His Ile Ser Tyr Arg Asp Val Val Asp Asp Phe Asn Arg
             55                  60                  65 tgc cat gat gtt ttt tat gag agg tac agt ttt gag gac ata aag agc   2098
Cys His Asp Val Phe Tyr Glu Arg Tyr Ser Phe Glu Asp Ile Lys Ser
         70                  75                  80 tac gag gct ttg cct gag gac aat ttg gag cag ctc ata gct atg cat   2146
Tyr Glu Ala Leu Pro Glu Asp Asn Leu Glu Gln Leu Ile Ala Met His
     85                  90                  95 gct aaa atc aag ctg ctg ccc ggt cgg gag tat gag ttg act caa cct   2194
Ala Lys Ile Lys Leu Leu Pro Gly Arg Glu Tyr Glu Leu Thr Gln Pro
100                 105                 110                 115 ttg aac ata aca tct tgc gcc tat gtg ctc gga aat ggg gct act att   2242
Leu Asn Ile Thr Ser Cys Ala Tyr Val Leu Gly Asn Gly Ala Thr Ile
                120                 125                 130 agg gta aca ggg gaa gcc tcc ccg gct att aga gtg ggg gcc atg gcc   2290
Arg Val Thr Gly Glu Ala Ser Pro Ala Ile Arg Val Gly Ala Met Ala
            135                 140                 145 gtg ggt ccg tgt gta aca gga atg act ggg gtg act ttt gtg aat tgt   2338
Val Gly Pro Cys Val Thr Gly Met Thr Gly Val Thr Phe Val Asn Cys
        150                 155                 160 agg ttt gag aga gag tca aca att agg ggg tcc ctg ata cga gct tca   2386
Arg Phe Glu Arg Glu Ser Thr Ile Arg Gly Ser Leu Ile Arg Ala Ser
    165                 170                 175 act cac gtg ctg ttt cat ggc tgt tat ttt atg gga att atg ggc act   2434
Thr His Val Leu Phe His Gly Cys Tyr Phe Met Gly Ile Met Gly Thr
180                 185                 190                 195 tgt att gag gtg ggg gcg gga gct tac att cgg ggt tgt gag ttt gtg   2482
Cys Ile Glu Val Gly Ala Gly Ala Tyr Ile Arg Gly Cys Glu Phe Val
                200                 205                 210 ggc tgt tac cgg gga atc tgt tct act tct aac aga gat att aag gtg   2530
Gly Cys Tyr Arg Gly Ile Cys Ser Thr Ser Asn Arg Asp Ile Lys Val
            215                 220                 225 agg cag tgc aac ttt gac aaa tgc tta ctg ggt att act tgt aag ggg   2578
Arg Gln Cys Asn Phe Asp Lys Cys Leu Leu Gly Ile Thr Cys Lys Gly
        230                 235                 240 gac tat cgt ctt tcg gga aat gtg tgt tct gag act ttc tgc ttt gct   2626
Asp Tyr Arg Leu Ser Gly Asn Val Cys Ser Glu Thr Phe Cys Phe Ala
    245                 250                 255 cat tta gag gga gag ggt ttg gtt aaa aac aac aca gtc aag tcc cct   2674
His Leu Glu Gly Glu Gly Leu Val Lys Asn Asn Thr Val Lys Ser Pro
260                 265                 270                 275 agt cgc tgg acc agc gag tct ggc ttt tcc atg ata act tgt gca gac   2722
Ser Arg Trp Thr Ser Glu Ser Gly Phe Ser Met Ile Thr Cys Ala Asp
                280                 285                 290
```

```
ggc agg gtt acg cct ttg ggt tcc ctc cac att gtg ggc aac cgt tgt    2770
Gly Arg Val Thr Pro Leu Gly Ser Leu His Ile Val Gly Asn Arg Cys
            295                 300                 305 agg cgt tgg cca acc atg cag ggg aat gtg ttt atc atg tct aaa ctg    2818
Arg Arg Trp Pro Thr Met Gln Gly Asn Val Phe Ile Met Ser Lys Leu
310                 315                 320 tat ctg ggc aac aga ata ggg act gta gcc ctg ccc cag tgt gct ttc    2866
Tyr Leu Gly Asn Arg Ile Gly Thr Val Ala Leu Pro Gln Cys Ala Phe
            325                 330                 335 tac aag tcc agc att tgt ttg gag gag agg gcg aca aac aag ctg gtc    2914
Tyr Lys Ser Ser Ile Cys Leu Glu Glu Arg Ala Thr Asn Lys Leu Val
340                 345                 350                 355 ttg gct tgt gct ttt gag aat aat gta ctg gtg tac aaa gtg ctg aga    2962
Leu Ala Cys Ala Phe Glu Asn Asn Val Leu Val Tyr Lys Val Leu Arg
            360                 365                 370 cgg gag agt ccc tca acc gtg aaa atg tgt gtt tgt ggg act tct cat    3010
Arg Glu Ser Pro Ser Thr Val Lys Met Cys Val Cys Gly Thr Ser His
            375                 380                 385 tat gca aag cct ttg aca ctg gca att att tct tca gat att cgg gct    3058
Tyr Ala Lys Pro Leu Thr Leu Ala Ile Ile Ser Ser Asp Ile Arg Ala
            390                 395                 400 aat cga tac atg tac act gtg gac tca aca gag ttc act tct gac gag    3106
Asn Arg Tyr Met Tyr Thr Val Asp Ser Thr Glu Phe Thr Ser Asp Glu
405                 410                 415 gat taaaagtggg cggggccaag aggggtataa ataggtgggg aggttgaggg          3159
Asp
420 gagccgtagt ttctgttttt cccagactgg ggggacaaac atggccgagg aagggcgcat   3219 ttatgtgcct tatgtaactg cccgcctgcc caagtggtcg ggttcggtgc aggataagac   3279 gggctcgaac atgttggggg gtgtggtact ccctcctaat tcacaggcgc accggacgga   3339 gaccgtgggc actgaggcca ccagagacaa cctgcacgcc gagggagcgc gtcgtcctga   3399 ggatcagacg ccctacatga tcttggtgga ggactctctg ggaggtttga agaggcgaat   3459 ggacttgctg gaagaatcta atcagcagct gctggcaact ctcaaccgtc ccgtacagg    3519 actcgctgcc tatgtgcagg ctaaccttgt gggcggccaa gttaacccct tgtttaaat    3579 aaaaatacac tcatacagtt tattatgctg tcaataaaat tctttatttt tcctgtgata   3639 ataccgtgtc cagcgtgctc tgtcaataag ggtcctatgc atcctgagaa gggcctcata   3699 tacccatggc atgaatatta agatacatgg gcataaggcc ctcagaaggg ttgaggtaga   3759 gccactgcag actttcgtgg ggaggtaagg tgttgtaaat aatccagtca tactgactgt   3819 gctgggcgtg gaaggaaaag atgtcttta gaagaagggt gattggcaaa gggaggctct   3879 tagtgtaggt attgataaat ctgttcagtt gggagggatg cattcggggg ctaataaggt   3939 ggagtttagc ctgaatctta aggttggcaa tgttgccccc taggtctttg cgaggattca   3999 tgttgtgcag taccacaaaa acagagtagc ctgtgcattt ggggaattta tcatgaagct   4059 t                                                                  4060

<210> SEQ ID NO 6
<211> LENGTH: 420
<212> TYPE: PRT
<213> ORGANISM: Bovine adenovirus type 3

<400> SEQUENCE: 6

Met Ala Glu Gly Gln Gly Val Gln Asp His Pro Glu Leu Gln Glu His
 1               5                  10                  15

Phe Ala Ala Phe Leu Val Ala Arg Gln Asp Asp Pro Asp Tyr Gln Pro
```

-continued

```
                 20                  25                  30
Val Asp Gly Asp Ser Pro Pro Arg Ala Ser Leu Glu Ala Glu Gln
             35                  40                  45
Ser Ser Thr Arg Phe Glu His Ile Ser Tyr Arg Asp Val Val Asp
 50                  55                  60
Phe Asn Arg Cys His Asp Val Phe Tyr Glu Arg Tyr Ser Phe Glu Asp
 65                  70                  75                  80
Ile Lys Ser Tyr Glu Ala Leu Pro Glu Asp Asn Leu Glu Gln Leu Ile
                 85                  90                  95
Ala Met His Ala Lys Ile Lys Leu Leu Pro Gly Arg Glu Tyr Glu Leu
            100                 105                 110
Thr Gln Pro Leu Asn Ile Thr Ser Cys Ala Tyr Val Leu Gly Asn Gly
            115                 120                 125
Ala Thr Ile Arg Val Thr Gly Glu Ala Ser Pro Ala Ile Arg Val Gly
        130                 135                 140
Ala Met Ala Val Gly Pro Cys Val Thr Gly Met Thr Gly Val Thr Phe
145                 150                 155                 160
Val Asn Cys Arg Phe Glu Arg Glu Ser Thr Ile Arg Gly Ser Leu Ile
                165                 170                 175
Arg Ala Ser Thr His Val Leu Phe His Gly Cys Tyr Phe Met Gly Ile
            180                 185                 190
Met Gly Thr Cys Ile Glu Val Gly Ala Gly Ala Tyr Ile Arg Gly Cys
        195                 200                 205
Glu Phe Val Gly Cys Tyr Arg Gly Ile Cys Ser Thr Ser Asn Arg Asp
        210                 215                 220
Ile Lys Val Arg Gln Cys Asn Phe Asp Lys Cys Leu Leu Gly Ile Thr
225                 230                 235                 240
Cys Lys Gly Asp Tyr Arg Leu Ser Gly Asn Val Cys Ser Glu Thr Phe
                245                 250                 255
Cys Phe Ala His Leu Glu Gly Glu Gly Leu Val Lys Asn Asn Thr Val
            260                 265                 270
Lys Ser Pro Ser Arg Trp Thr Ser Glu Ser Gly Phe Ser Met Ile Thr
        275                 280                 285
Cys Ala Asp Gly Arg Val Thr Pro Leu Gly Ser Leu His Ile Val Gly
        290                 295                 300
Asn Arg Cys Arg Arg Trp Pro Thr Met Gln Gly Asn Val Phe Ile Met
305                 310                 315                 320
Ser Lys Leu Tyr Leu Gly Asn Arg Ile Gly Thr Val Ala Leu Pro Gln
                325                 330                 335
Cys Ala Phe Tyr Lys Ser Ser Ile Cys Leu Glu Glu Arg Ala Thr Asn
            340                 345                 350
Lys Leu Val Leu Ala Cys Ala Phe Glu Asn Asn Val Leu Val Tyr Lys
        355                 360                 365
Val Leu Arg Arg Glu Ser Pro Ser Thr Val Lys Met Cys Val Cys Gly
        370                 375                 380
Thr Ser His Tyr Ala Lys Pro Leu Thr Leu Ala Ile Ile Ser Ser Asp
385                 390                 395                 400
Ile Arg Ala Asn Arg Tyr Met Tyr Thr Val Asp Ser Thr Glu Phe Thr
                405                 410                 415
Ser Asp Glu Asp
            420

<210> SEQ ID NO 7
<211> LENGTH: 4060
```

```
<212> TYPE: DNA
<213> ORGANISM: Bovine adenovirus type 3
<220> FEATURE:
<221> NAME/KEY: CDS
<222> LOCATION: (3200)..(3574)

<400> SEQUENCE: 7
catcatcaat aatctacagt acactgatgg cagcggtcca actgccaatc attttttgcca      60
cgtcatttat gacgcaacga cggcgagcgt ggcgtgctga cgtaactgtg gggcggagcg     120
cgtcgcggag gcggcggcgc tgggcgggc tgagggcggc ggggcggcg cgcggggcgg      180
cgcgcgggc ggggcgaggg gcggagttcc gcacccgcta cgtcattttc agacattttt     240
tagcaaattt gcgccttttg caagcatttt tctcacattt caggtattta gagggcggat     300
ttttggtgtt cgtacttccg tgtcacatag ttcactgtca atcttcatta cggcttagac     360
aaattttcgg cgtctttttcc gggtttatgt cccgggtcac ctttatgact gtgtgaaaca     420
cacctgccca ttgtttaccc ttggtcagtt ttttcgtctc ctagggtggg aacatcaaga     480
acaaatttgc cgagtaattg tgcaccttt tccgcgttag gactgcgttt cacacgtaga     540
cagactttt ctcattttct cacactccgt cgtccgcttc agagctctgc gtcttcgctg     600
ccaccatgaa gtacctggtc ctcgttctca cgacggcat gagtcgaatt gaaaaagctc     660
tcctgtgcag cgatggtgag gtggatttag agtgtcatga ggtacttccc ccttctcccg     720
cgcctgtccc cgcttctgtg tcacccgtga ggagtcctcc tcctctgtct ccggtgtttc     780
ctccgtctcc gccagcccg cttgtgaatc cagaggcgag ttcgctgctg cagcagtatc     840
ggagagagct gttagagagg agcctgctcc gaacggccga aggtcagcag cgtgcagtgt     900
gtccatgtga gcggttgccc gtggaagagg atgagtgtct gaatgccgta aatttgctgt     960
ttcctgatcc ctggctaaat gcagctgaaa atgggggtga tatttttaag tctccggcta    1020
tgtctccaga accgtggata gatttgtcta gctacgatag cgatgtagaa gaggtgacta    1080
gtcactttt tctggattgc cctgaagacc ccagtcggga gtgttcatct tgtgggtttc    1140
atcaggctca aagcggaatt ccaggcatta tgtgcagttt tgtgctacatg cgccaaacct    1200
accattgcat ctatagtaag tacattctgt aaaagaacat cttggtgatt tctaggtatt    1260
gtttagggat taactgggtg gagtgatctt aatccggcat aaccaaatac atgttttcac    1320
aggtccagtt tctgaagagg aaatgtgagt catgttgact ttggcgcgca agaggaaatg    1380
tgagtcatgt tgactttggc gcgcctacg gtgactttaa agcaatttga ggatcacttt    1440
tttgttagtc gctataaagt agtcacggag tcttcatgga tcacttaagc gttctttttgg    1500
atttgaagct gcttcgctct atcgtagcgg gggcttcaaa tcgcactgga gtgtggaaga    1560
ggcggctgtg gctgggacgc ctgactcaac tggtccatga tacctgcgta gagaacgaga    1620
gcatatttct caattctctg ccagggaatg aagctttttt aaggttgctt cggagcggct    1680
attttgaagt gtttgacgtg tttgtggtgc ctgagctgca tctggacact ccgggtcgag    1740
tggtcgccgc tcttgctctg ctggtgttca tcctcaacga tttagacgct aattctgctt    1800
cttcaggctt tgattcaggt tttctcgtgg accgtctctg cgtgccgcta tggctgaagg    1860
ccagggcgtt caagatcacc cagagctcca ggagcacttc gcagccttcc tcgtcgcccg    1920
acaagacgac ccagactacc agccagtaga cggggacagc ccaccccggg ctagcctgga    1980
ggaggctgaa cagagcagca ctcgtttcga gcacatcagt taccgagacg tggtggatga    2040
cttcaataga tgccatgatg ttttttatga gaggtacagt tttgaggaca taagagcta    2100
cgaggctttg cctgaggaca atttggagca gctcatagct atgcatgcta aaatcaagct    2160
```

-continued

```
gctgcccggt cgggagtatg agttgactca acctttgaac ataacatctt gcgcctatgt    2220
gctcggaaat ggggctacta ttagggtaac aggggaagcc tccccggcta ttagagtggg    2280
ggccatggcc gtgggtccgt gtgtaacagg aatgactggg gtgacttttg tgaattgtag    2340
gtttgagaga gagtcaacaa ttaggggtc cctgatacga gcttcaactc acgtgctgtt     2400
tcatggctgt tattttatgg gaattatggg cacttgtatt gaggtggggg cgggagctta   2460
cattcggggt tgtgagtttg tgggctgtta ccggggaatc tgttctactt ctaacagaga    2520
tattaaggtg aggcagtgca actttgacaa atgcttactg ggtattactt gtaagggga    2580 ctatcgtctt tcgggaaatg tgtgttctga gactttctgc tttgctcatt tagagggaga   2640
gggtttggtt aaaaacaaca cagtcaagtc ccctagtcgc tggaccagcg agtctggctt    2700
ttccatgata acttgtgcag acgcagggt tacgccttg ggttccctcc acattgtggg      2760
caaccgttgt aggcgttggc caaccatgca ggggaatgtg tttatcatgt ctaaactgta    2820
tctgggcaac agaataggga ctgtagcccct gccccagtgt gctttctaca agtccagcat   2880
ttgtttggag gagagggcga caaacaagct ggtcttggct tgtgcttttg agaataatgt    2940
actggtgtac aaagtgctga gacgggagag tccctcaacc gtgaaaatgt gtgtttgtgg   3000
gacttctcat tatgcaaagc ctttgacact ggcaattatt tcttcagata ttcgggctaa    3060
tcgatacatg tacactgtgg actcaacaga gttcacttct gacgaggatt aaaagtgggc    3120
ggggccaaga gggtataaa taggtgggga ggttgagggg agccgtagtt tctgttttc     3180 ccagactggg ggggacaac atg gcc gag gaa ggg cgc att tat gtg cct tat    3232
                      Met Ala Glu Glu Gly Arg Ile Tyr Val Pro Tyr
                       1               5                  10 gta act gcc cgc ctg ccc aag tgg tcg ggt tcg gtg cag gat aag acg      3280
Val Thr Ala Arg Leu Pro Lys Trp Ser Gly Ser Val Gln Asp Lys Thr
         15                  20                  25 ggc tcg aac atg ttg ggg ggt gtg gta ctc cct cct aat tca cag gcg      3328
Gly Ser Asn Met Leu Gly Gly Val Val Leu Pro Pro Asn Ser Gln Ala
     30                  35                  40 cac cgg acg gag acc gtg ggc act gag gcc acc aga gac aac ctg cac      3376
His Arg Thr Glu Thr Val Gly Thr Glu Ala Thr Arg Asp Asn Leu His
 45                  50                  55 gcc gag gga gcg cgt cgt cct gag gat cag acg ccc tac atg atc ttg      3424
Ala Glu Gly Ala Arg Arg Pro Glu Asp Gln Thr Pro Tyr Met Ile Leu
 60                  65                  70                  75 gtg gag gac tct ctg gga ggt ttg aag agg cga atg gac ttg ctg gaa      3472
Val Glu Asp Ser Leu Gly Gly Leu Lys Arg Arg Met Asp Leu Leu Glu
             80                  85                  90 gaa tct aat cag cag ctg ctg gca act ctc aac cgt ctc cgt aca gga      3520
Glu Ser Asn Gln Gln Leu Leu Ala Thr Leu Asn Arg Leu Arg Thr Gly
         95                  100                 105 ctc gct gcc tat gtg cag gct aac ctt gtg ggc ggc caa gtt aac ccc      3568
Leu Ala Ala Tyr Val Gln Ala Asn Leu Val Gly Gly Gln Val Asn Pro
     110                 115                 120 ttt gtt taaataaaaa tacactcata cagtttatta tgctgtcaat aaaattcttt       3624
Phe Val
    125 atttttcctg tgataatacc gtgtccagcg tgctctgtca ataagggtcc tatgcatcct    3684 gagaagggcc tcatataccc atggcatgaa tattaagata catgggcata aggccctcag    3744 aagggttgag gtagagccac tgcagacttt cgtgggagg taaggtgttg taaataatcc     3804 agtcatactg actgtgctgg gcgtggaagg aaaagatgtc ttttagaaga agggtgattg    3864 gcaaagggag gctcttagtg taggtattga taaatctgtt cagttgggag ggatgcattc    3924
```

-continued

```
gggggctaat aaggtggagt ttagcctgaa tcttaaggtt ggcaatgttg cccccctaggt    3984 ctttgcgagg attcatgttg tgcagtacca caaaaacaga gtagcctgtg catttgggga    4044
atttatcatg aagctt                                                    4060
```

<210> SEQ ID NO 8
<211> LENGTH: 125
<212> TYPE: PRT
<213> ORGANISM: Bovine adenovirus type 3

<400> SEQUENCE: 8

Met Ala Glu Glu Gly Arg Ile Tyr Val Pro Tyr Val Thr Ala Arg Leu
 1               5                  10                  15

Pro Lys Trp Ser Gly Ser Val Gln Asp Lys Thr Gly Ser Asn Met Leu
             20                  25                  30

Gly Gly Val Val Leu Pro Pro Asn Ser Gln Ala His Arg Thr Glu Thr
         35                  40                  45

Val Gly Thr Glu Ala Thr Arg Asp Asn Leu His Ala Glu Gly Ala Arg
     50                  55                  60

Arg Pro Glu Asp Gln Thr Pro Tyr Met Ile Leu Val Glu Asp Ser Leu
 65                  70                  75                  80

Gly Gly Leu Lys Arg Arg Met Asp Leu Leu Glu Glu Ser Asn Gln Gln
                 85                  90                  95

Leu Leu Ala Thr Leu Asn Arg Leu Arg Thr Gly Leu Ala Ala Tyr Val
            100                 105                 110

Gln Ala Asn Leu Val Gly Gly Val Asn Pro Phe Val
        115                 120                 125

<210> SEQ ID NO 9
<211> LENGTH: 54
<212> TYPE: PRT
<213> ORGANISM: Human adenovirus type 5

<400> SEQUENCE: 9

Glu Glu Phe Val Leu Asp Tyr Val Glu His Pro Gly His Gly Cys Arg
 1               5                  10                  15

Ser Cys His Tyr His Arg Arg Asn Thr Gly Asp Pro Asp Ile Met Cys
             20                  25                  30

Ser Leu Cys Tyr Met Arg Thr Cys Gly Met Phe Val Tyr Ser Pro Val
         35                  40                  45

Ser Glu Pro Glu Pro Glu
     50

<210> SEQ ID NO 10
<211> LENGTH: 13
<212> TYPE: PRT
<213> ORGANISM: Human adenovirus type 5

<400> SEQUENCE: 10

Ile Asp Leu Thr Cys His Glu Ala Gly Phe Pro Pro Ser
 1               5                  10

<210> SEQ ID NO 11
<211> LENGTH: 19
<212> TYPE: PRT
<213> ORGANISM: Human adenovirus type 5

<400> SEQUENCE: 11

Leu Asp Phe Ser Thr Pro Gly Arg Ala Ala Ala Val Ala Phe Leu
 1               5                  10                  15
Ser Phe Ile

<210> SEQ ID NO 12
<211> LENGTH: 7
<212> TYPE: PRT
<213> ORGANISM: Human adenovirus type 5

<400> SEQUENCE: 12

Gln Ser Ser Asn Ser Thr Ser
 1               5

<210> SEQ ID NO 13
<211> LENGTH: 347
<212> TYPE: PRT
<213> ORGANISM: Human adenovirus type 5

<400> SEQUENCE: 13

Gln Lys Tyr Ser Ile Glu Gln Leu Thr Thr Tyr Trp Leu Gln Pro Gly
 1               5                  10                  15

Asp Asp Phe Glu Glu Ala Ile Arg Val Tyr Ala Lys Val Ala Leu Arg
                20                  25                  30

Pro Asp Cys Lys Tyr Lys Ile Ser Lys Leu Val Asn Ile Arg Asn Cys
            35                  40                  45

Cys Tyr Ile Ser Gly Asn Gly Ala Glu Val Glu Ile Asp Thr Glu Asp
        50                  55                  60

Arg Val Ala Phe Arg Cys Ser Met Ile Asn Met Trp Pro Gly Val Leu
 65                 70                  75                  80

Gly Met Asp Gly Val Val Ile Met Asn Val Arg Phe Thr Gly Pro Asn
                85                  90                  95

Phe Ser Gly Thr Val Phe Leu Ala Asn Thr Asn Leu Ile Leu His Gly
            100                 105                 110

Val Ser Phe Tyr Gly Phe Asn Asn Thr Cys Val Glu Ala Trp Thr Asp
        115                 120                 125

Val Arg Val Arg Gly Cys Ala Phe Tyr Cys Cys Trp Lys Gly Val Val
130                 135                 140

Cys Arg Pro Lys Ser Arg Ala Ser Ile Lys Cys Leu Phe Glu Arg
145                 150                 155                 160

Cys Thr Leu Gly Ile Leu Ser Glu Gly Asn Ser Arg Val Arg His Asn
                165                 170                 175

Val Ala Ser Asp Cys Gly Cys Phe Met Leu Val Lys Ser Val Ala Val
            180                 185                 190

Ile Lys His Asn Met Val Cys Gly Asn Cys Glu Asp Arg Ala Ser Gln
        195                 200                 205

Met Leu Thr Cys Ser Asp Gly Asn Cys His Leu Leu Lys Thr Ile His
    210                 215                 220

Val Ala Ser His Ser Arg Lys Ala Trp Pro Val Phe Glu His Asn Ile
225                 230                 235                 240

Leu His Arg Cys Ser Leu His Leu Gly Asn Arg Arg Gly Val Phe Leu
                245                 250                 255

Pro Tyr Gln Cys Asn Leu Ser His Thr Lys Ile Leu Leu Glu Pro Glu
            260                 265                 270

Ser Met Ser Lys Val Asn Leu Asn Gly Val Phe Asp Met Thr Met Lys
        275                 280                 285

Ile Trp Lys Val Leu Arg Tyr Asp Glu Thr Arg Thr Arg Cys Arg Pro
    290                 295                 300

Cys Glu Cys Gly Gly Lys His Ile Arg Asn Gln Pro Val Met Leu Asp
305                 310                 315                 320

```
Val Thr Glu Glu Leu Arg Pro Asp His Leu Val Leu Ala Cys His Arg
            325                 330                 335

Ala Glu Phe Gly Ser Ser Asp Glu Asp Thr Asp
            340                 345

<210> SEQ ID NO 14
<211> LENGTH: 140
<212> TYPE: PRT
<213> ORGANISM: Human adenovirus type 5

<400> SEQUENCE: 14

Met Ser Thr Asn Ser Phe Asp Gly Ser Ile Val Ser Ser Tyr Leu Thr
  1               5                  10                  15

Thr Arg Met Pro Pro Trp Ala Gly Val Arg Gln Asn Val Met Gly Ser
             20                  25                  30

Ser Ile Asp Gly Arg Pro Val Leu Pro Ala Asn Ser Thr Thr Leu Thr
         35                  40                  45

Tyr Glu Thr Val Ser Gly Thr Pro Leu Glu Thr Ala Ala Ser Ala Ala
 50                  55                  60

Ala Ser Ala Ala Ala Thr Ala Arg Gly Ile Val Thr Asp Phe Ala
 65                  70                  75                  80

Phe Leu Ser Pro Leu Ala Ser Ser Ala Ala Ser Arg Ser Ser Ala Arg
             85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
            115                 120                 125

Ser Ala Leu Lys Ala Ser Ser Pro Pro Asn Ala Val
            130                 135                 140

<210> SEQ ID NO 15
<211> LENGTH: 5100
<212> TYPE: DNA
<213> ORGANISM: Bovine adenovirus type 3
<220> FEATURE:
<221> NAME/KEY: CDS
<222> LOCATION: (2)..(418)

<400> SEQUENCE: 15 c ctc atc aaa caa ccc gtg gtg ggc acc acc cac gtg gaa atg cct cgc        49
  Leu Ile Lys Gln Pro Val Val Gly Thr Thr His Val Glu Met Pro Arg
    1               5                  10                  15 aac gaa gtc cta gaa caa cat ctg acc tca cat ggc gct caa atc gcg         97
Asn Glu Val Leu Glu Gln His Leu Thr Ser His Gly Ala Gln Ile Ala
             20                  25                  30 ggc gga ggc gct gcg ggc gat tac ttt aaa agc ccc act tca gct cga        145
Gly Gly Gly Ala Ala Gly Asp Tyr Phe Lys Ser Pro Thr Ser Ala Arg
         35                  40                  45 acc ctt atc ccg ctc acc gcc tcc tgc tta aga cca gat gga gtc ttt        193
Thr Leu Ile Pro Leu Thr Ala Ser Cys Leu Arg Pro Asp Gly Val Phe
 50                  55                  60 caa cta gga gga ggc tcg cgt tca tct ttc aac ccc ctg caa aca gat        241
Gln Leu Gly Gly Gly Ser Arg Ser Ser Phe Asn Pro Leu Gln Thr Asp
 65                  70                  75                  80 ttt gcc ttc cac gcc ctg ccc tcc aga ccg cgc cac ggg ggc ata gga        289
Phe Ala Phe His Ala Leu Pro Ser Arg Pro Arg His Gly Gly Ile Gly
             85                  90                  95 tcc agg cag ttt gta gag gaa ttt gtg ccc gcc gtc tac ctc aac ccc        337
Ser Arg Gln Phe Val Glu Glu Phe Val Pro Ala Val Tyr Leu Asn Pro
            100                 105                 110
```

-continued

| | |
|---|---|
| tac tcg gga ccg ccg gac tct tat ccg gac cag ttt ata cgc cac tac<br>Tyr Ser Gly Pro Pro Asp Ser Tyr Pro Asp Gln Phe Ile Arg His Tyr<br>115                           120                       125 | 385 |
| aac gtg tac agc aac tct gtg agc ggt tat agc tgagattgta agactctcct<br>Asn Val Tyr Ser Asn Ser Val Ser Gly Tyr Ser<br>130                       135 | 438 |
| atctgtctct gtgctgcttt tccgcttcaa gccccacaag catgaagggg tttctgctca | 498 |
| tcttcagcct gcttgtgcat tgtccctaa ttcatgttgg gaccattagc ttctatgctg | 558 |
| caaggcccgg gtctgagcct aacgcgactt atgtttgtga ctatggaagc gagtcagatt | 618 |
| acaaccccac cacggttctg tggttggctc gagagaccga tggctcctgg atctctgttc | 678 |
| ttttccgtca caacggctcc tcaactgcag ccccgggggt cgtcgcgcac tttactgacc | 738 |
| acaacagcag cattgtggtg cccagtatt acctcctcaa caactcactc tctaagctct | 798 |
| gctgctcata ccggcacaac gagcgttctc agtttacctg caaacaagct gacgtcccta | 858 |
| cctgtcacga gcccggcaag ccgctcaccc tccgcgtctc ccccgcgctg ggaactgccc | 918 |
| accaagcagt cacttggttt ttcaaaatg tacccatagc tactgtttac cgaccttggg | 978 |
| gcaatgtaac ttggttttgt cctcccttca tgtgtacctt taatgtcagc ctgaactccc | 1038 |
| tacttattta caacttttct gacaaaaccg ggggcaata cacagctctc atgcactccg | 1098 |
| gacctgcttc cctcttttcag ctctttaagc caacgacttg tgtcaccaag gtggaggacc | 1158 |
| cgccgtatgc caacgacccg gcctcgcctg tgtggcgccc actgcttttt gccttcgtcc | 1218 |
| tctgcaccgg ctgcgcggtg ttgttaaccg ccttcggtcc atcgattcta tccggtaccc | 1278 |
| gaaagcttat ctcagcccgc ttttggagtc ccgagcccta taccaccctc cactaacagt | 1338 |
| cccccatgg agccagacgg agttcatgcc gagcagcagt ttatcctcaa tcagatttcc | 1398 |
| tgcgccaaca ctgccctcca gcgtcaaagg gaggaactag cttcccttgt catgttgcat | 1458 |
| gcctgtaagc gtgcctctt ttgtccagtc aaaacttaca agctcagcct caacgcctcg | 1518 |
| gccagcgagc acagcctgca ctttgaaaaa agtccctccc gattcaccct ggtcaacact | 1578 |
| cacgccggag cttctgtgcg agtggcccta caccaccagg gagcttccgg cagcatccgc | 1638 |
| tgttcctgtt cccacgccga gtgcctcccc gtcctcctca agaccctctg tgcctttaac | 1698 |
| tttttagatt agctgaaagc aaatataaaa tggtgtgctt accgtaattc tgttttgact | 1758 |
| tgtgtgcttg atttctcccc ctgcgccgta atccagtgcc cctcttcaaa actctcgtac | 1818 |
| cctatgcgat tcgcataggc atattttcta aaagctctga agtcaacatc actctcaaac | 1878 |
| acttctccgt tgtaggttac tttcatctac agataaagtc atccaccggt taacatcatg | 1938 |
| aagagaagtg tgccccagga ctttaatctt gtgtatccgt acaaggctaa gaggcccaac | 1998 |
| atcatgccgc ccttttttga ccgcaatggc tttgttgaaa accaagaagc cacgctagcc | 2058 |
| atgcttgtgg aaaagccgct cacgttcgac aaggaaggtg cgctgaccct gggcgtcgga | 2118 |
| cgcggcatcc gcattaaccc cgcggggctt ctggagacaa cgacctcgc gtccgctgtc | 2178 |
| ttcccaccgc tggcctccga tgaggccggc aacgtcacgc tcaacatgtc tgacgggcta | 2238 |
| tatactaagg acaacaagct agctgtcaaa gtaggtcccg ggctgtccct cgactccaat | 2298 |
| aatgctctcc aggtccacac aggcgacggg ctcacggtaa ccgatgacaa ggtgtctcta | 2358 |
| aatacccaag ctcccctctc gaccaccagc gcgggcctct ccctacttct gggtcccagc | 2418 |
| ctccacttag gtgaggagga acgactaaca gtaaacaccg gagcgggcct ccaaattagc | 2478 |
| aataacgctc tggccgtaaa agtaggttca ggtatcaccg tagatgctca aaaccagctc | 2538 |
| gctgcatccc tgggggacgg tctagaaagc agagataata aaactgtcgt taaggctggg | 2598 |

```
cccggactta caataactaa tcaagctctt actgttgcta ccgggaacgg ccttcaggtc    2658
aacccggaag ggcaactgca gctaaacatt actgccggtc agggcctcaa ctttgcaaac    2718
aacagcctcg ccgtggagct gggctcgggc ctgcattttc ccctggcca aaaccaagta    2778 agcctttatc ccggagatgg aatagacatc cgagataata gggtgactgt gcccgctggg    2838
ccaggcctga gaatgctcaa ccaccaactt gccgtagctt ccggagacgg tttagaagtc    2898
cacagcgaca ccctccggtt aaagctctcc cacggcctga catttgaaaa tggcgccgta    2958
cgagcaaaac taggaccagg acttggcaca gacgactctg gtcggtccgt ggttcgcaca    3018
ggtcgaggac ttagagttgc aaacggccaa gtccagatct tcagcggaag aggcaccgcc    3078
atcggcactg atagcagcct cactctcaac atccgggcgc ccctacaatt ttctggaccc    3138
gccttgactg ctagtttgca aggcagtggt ccgattactt acaacagcaa caatggcact    3198
ttcggtctct ctataggccc cggaatgtgg gtagaccaaa acagacttca ggtaaaccca    3258
ggcgctggtt tagtcttcca aggaaacaac cttgtcccaa accttgcgga tccgctggct    3318
atttccgaca gcaaaattag tctcagtctc ggtcccggcc tgacccaagc ttccaacgcc    3378
ctgactttaa gtttaggaaa cgggcttgaa ttctccaatc aagccgttgc tataaaagcg    3438
ggccggggct tacgctttga gtcttcctca caagctttag agagcagcct cacagtcgga    3498
aatggcttaa cgcttaccga tactgtgatc cgccccaacc taggggacgg cctagaggtc    3558
agagacaata aaatcattgt taagctgggc gcgaatcttc gttttgaaaa cggagccgta    3618
accgccggca ccgttaaccc ttctgcgccc gaggcaccac caactctcac tgcagaacca    3678
cccctccgag cctccaactc ccatcttcaa ctgtccctat cggagggctt ggttgtgcat    3738
aacaacgccc ttgctctcca actgggagac ggcatggaag taaatcagca cggacttact    3798
ttaagagtag gctcgggttt gcaaatgcgt gacggcattt taacagttac acccagcggc    3858
actcctattg agcccagact gactgcccca ctgactcaga cagagaatgg aatcgggctc    3918
gctctcggcg ccggcttgga attagacgag agcgcgctcc aagtaaaagt tgggcccggc    3978
atgcgcctga accctgtaga aaagtatgta accctgctcc tgggtcctgg ccttagtttt    4038
gggcagccgg ccaacaggac aaattatgat gtgcgcgttt ctgtggagcc ccccatggtt    4098
ttcggacagc gtggtcagct cacattttta gtgggtcacg gactacacat tcaaaattcc    4158
aaacttcagc tcaatttggg acaaggcctc agaactgacc ccgtcaccaa ccagctggaa    4218
gtgcccctcg gtcaaggttt ggaaattgca gacgaatccc aggttagggt taaattgggc    4278
gatggcctgc agtttgattc acaagctcgc atcactaccg ctcctaacat ggtcactgaa    4338
actctgtgga ccggaacagg cagtaatgct aatgttacat ggcggggcta cactgccccc    4398
ggcagcaaac tctttttgag tctcactcgg ttcagcactg gtctagtttt aggaaacatg    4458
actattgaca gcaatgcatc ctttgggcaa tacattaacg cgggacacga acagatcgaa    4518
tgctttatat tgttggacaa tcagggtaac ctaaaagaag gatctaactt gcaaggcact    4578
tgggaagtga gaacaacccc ctctgcttcc aaagctgctt ttttgccttc caccgcccta    4638 tacccatcc tcaacgaaag ccgagggagt cttcctggaa aaaatcttgt gggcatgcaa    4698
gccatactgg gaggcggggg cacttgcact gtgatagcca ccctcaatgg cagacgcagc    4758
aacaactatc ccgcgggcca gtccataatt ttcgtgtggc aagaattcaa caccatagcc    4818
cgccaacctc tgaaccactc tacacttact ttttcttact ggacttaaat aagttggaaa    4878
taaagagtta aactgaatgt ttaagtgcaa cagactttta ttggttttgg ctcacaacaa    4938
attacaacag catagacaag tcataccggt caaacaacac aggctctcga aaacgggcta    4998
```

```
accgctccaa gaatctgtca cgcagacgag caagtcctaa atgttttttc actctcttcg     5058
gggccaagtt cagcatgtat cggatttct gcttacacct tt                        5100

<210> SEQ ID NO 16
<211> LENGTH: 139
<212> TYPE: PRT
<213> ORGANISM: Bovine adenovirus type 3

<400> SEQUENCE: 16

Leu Ile Lys Gln Pro Val Val Gly Thr Thr His Val Glu Met Pro Arg
  1               5                  10                  15

Asn Glu Val Leu Glu Gln His Leu Thr Ser His Gly Ala Gln Ile Ala
             20                  25                  30

Gly Gly Gly Ala Ala Gly Asp Tyr Phe Lys Ser Pro Thr Ser Ala Arg
         35                  40                  45

Thr Leu Ile Pro Leu Thr Ala Ser Cys Leu Arg Pro Asp Gly Val Phe
     50                  55                  60

Gln Leu Gly Gly Gly Ser Arg Ser Ser Phe Asn Pro Leu Gln Thr Asp
 65                  70                  75                  80

Phe Ala Phe His Ala Leu Pro Ser Arg Pro Arg His Gly Gly Ile Gly
                 85                  90                  95

Ser Arg Gln Phe Val Glu Glu Phe Val Pro Ala Val Tyr Leu Asn Pro
            100                 105                 110

Tyr Ser Gly Pro Pro Asp Ser Tyr Pro Asp Gln Phe Ile Arg His Tyr
        115                 120                 125

Asn Val Tyr Ser Asn Ser Val Ser Gly Tyr Ser
        130                 135

<210> SEQ ID NO 17
<211> LENGTH: 5100
<212> TYPE: DNA
<213> ORGANISM: Bovine adenovirus type 3
<220> FEATURE:
<221> NAME/KEY: CDS
<222> LOCATION: (408)..(1331)

<400> SEQUENCE: 17
cctcatcaaa caacccgtgg tgggcaccac ccacgtggaa atgcctcgca acgaagtcct      60
agaacaacat ctgacctcac atggcgctca atcgcgggc ggaggcgctg cgggcgatta     120
ctttaaaagc cccacttcag ctcgaaccct tatcccgctc accgcctcct gcttaagacc     180
agatggagtc tttcaactag gaggaggctc gcgttcatct ttcaaccccc tgcaaacaga     240
ttttgccttc cacgccctgc cctccagacc gcgccacggg ggcataggat ccaggcagtt     300
tgtagaggaa tttgtgcccg ccgtctacct caacccctac tcgggaccgc cggactctta     360
tccggaccag tttatacgcc actacaacgt gtacagcaac tctgtga gcg gtt ata       416
                                                   Ala Val Ile
                                                     1 gct gag att gta aga ctc tcc tat ctg tct ctg tgc tgc ttt tcc gct       464
Ala Glu Ile Val Arg Leu Ser Tyr Leu Ser Leu Cys Cys Phe Ser Ala
      5                  10                  15 tca agc ccc aca agc atg aag ggg ttt ctg ctc atc ttc agc ctg ctt       512
Ser Ser Pro Thr Ser Met Lys Gly Phe Leu Leu Ile Phe Ser Leu Leu
 20                  25                  30                  35 gtg cat tgt ccc cta att cat gtt ggg acc att agc ttc tat gct gca       560
Val His Cys Pro Leu Ile His Val Gly Thr Ile Ser Phe Tyr Ala Ala
             40                  45                  50 agg ccc ggg tct gag cct aac gcg act tat gtt tgt gac tat gga agc       608
Arg Pro Gly Ser Glu Pro Asn Ala Thr Tyr Val Cys Asp Tyr Gly Ser
```

-continued

```
                      55                     60                     65
gag tca gat tac aac ccc acc acg gtt ctg tgg ttg gct cga gag acc        656
Glu Ser Asp Tyr Asn Pro Thr Thr Val Leu Trp Leu Ala Arg Glu Thr
            70                  75                  80 gat ggc tcc tgg atc tct gtt ctt ttc cgt cac aac ggc tcc tca act        704
Asp Gly Ser Trp Ile Ser Val Leu Phe Arg His Asn Gly Ser Ser Thr
        85                  90                  95 gca gcc ccc ggg gtc gtc gcg cac ttt act gac cac aac agc agc att        752
Ala Ala Pro Gly Val Val Ala His Phe Thr Asp His Asn Ser Ser Ile
100                 105                 110                 115 gtg gtg ccc cag tat tac ctc ctc aac aac tca ctc tct aag ctc tgc        800
Val Val Pro Gln Tyr Tyr Leu Leu Asn Asn Ser Leu Ser Lys Leu Cys
                120                 125                 130 tgc tca tac cgg cac aac gag cgt tct cag ttt acc tgc aaa caa gct        848
Cys Ser Tyr Arg His Asn Glu Arg Ser Gln Phe Thr Cys Lys Gln Ala
            135                 140                 145 gac gtc cct acc tgt cac gag ccc ggc aag ccg ctc acc ctc cgc gtc        896
Asp Val Pro Thr Cys His Glu Pro Gly Lys Pro Leu Thr Leu Arg Val
        150                 155                 160 tcc ccc gcg ctg gga act gcc cac caa gca gtc act tgg ttt ttt caa        944
Ser Pro Ala Leu Gly Thr Ala His Gln Ala Val Thr Trp Phe Phe Gln
165                 170                 175 aat gta ccc ata gct act gtt tac cga cct tgg ggc aat gta act tgg        992
Asn Val Pro Ile Ala Thr Val Tyr Arg Pro Trp Gly Asn Val Thr Trp
180                 185                 190                 195 ttt tgt cct ccc ttc atg tgt acc ttt aat gtc agc ctg aac tcc cta       1040
Phe Cys Pro Pro Phe Met Cys Thr Phe Asn Val Ser Leu Asn Ser Leu
                200                 205                 210 ctt att tac aac ttt tct gac aaa acc ggg ggg caa tac aca gct ctc       1088
Leu Ile Tyr Asn Phe Ser Asp Lys Thr Gly Gly Gln Tyr Thr Ala Leu
            215                 220                 225 atg cac tcc gga cct gct tcc ctc ttt cag ctc ttt aag cca acg act       1136
Met His Ser Gly Pro Ala Ser Leu Phe Gln Leu Phe Lys Pro Thr Thr
        230                 235                 240 tgt gtc acc aag gtg gag gac ccg ccg tat gcc aac gac ccg gcc tcg       1184
Cys Val Thr Lys Val Glu Asp Pro Pro Tyr Ala Asn Asp Pro Ala Ser
245                 250                 255 cct gtg tgg cgc cca ctg ctt ttt gcc ttc gtc ctc tgc acc ggc tgc       1232
Pro Val Trp Arg Pro Leu Leu Phe Ala Phe Val Leu Cys Thr Gly Cys
260                 265                 270                 275 gcg gtg ttg tta acc gcc ttc ggt cca tcg att cta tcc ggt acc cga       1280
Ala Val Leu Leu Thr Ala Phe Gly Pro Ser Ile Leu Ser Gly Thr Arg
                280                 285                 290 aag ctt atc tca gcc cgc ttt tgg agt ccc gag ccc tat acc acc ctc       1328
Lys Leu Ile Ser Ala Arg Phe Trp Ser Pro Glu Pro Tyr Thr Thr Leu
            295                 300                 305 cac taacagtccc cccatggagc cagacggagt tcatgccgag cagcagttta            1381
His tcctcaatca gatttcctgc gccaacactg ccctccagcg tcaagggag gaactagctt      1441 cccttgtcat gttgcatgcc tgtaagcgtg gcctcttttg tccagtcaaa acttacaagc     1501
tcagcctcaa cgcctcggcc agcgagcaca gcctgcactt tgaaaaaagt ccctcccgat     1561
tcaccctggt caacactcac gccggagctt ctgtgcgagt ggcctacac caccagggag      1621 cttccggcag catccgctgt tcctgttccc acgccgagtg cctccccgtc tcctcaaga     1681 ccctctgtgc ctttaacttt ttagattagc tgaaagcaaa tataaaatgg tgtgcttacc    1741
gtaattctgt tttgacttgt gtgcttgatt tctccccctg cgccgtaatc cagtgccct    1801 cttcaaaact ctcgtaccct atgcgattcg cataggcata ttttctaaaa gctctgaagt   1861
```

```
caacatcact ctcaaacact tctccgttgt aggttacttt catctacaga taaagtcatc    1921
caccggttaa catcatgaag agaagtgtgc cccaggactt taatcttgtg tatccgtaca    1981
aggctaagag gcccaacatc atgccgccct tttttgaccg caatggcttt gttgaaaacc    2041
aagaagccac gctagccatg cttgtggaaa agccgctcac gttcgacaag aaggtgcgc    2101 tgaccctggg cgtcggacgc ggcatccgca ttaaccccgc ggggcttctg gagacaaacg    2161
acctcgcgtc cgctgtcttc ccaccgctgg cctccgatga ggccggcaac gtcacgctca    2221
acatgtctga cgggctatat actaaggaca caagctagc tgtcaaagta ggtcccgggc    2281
tgtccctcga ctccaataat gctctccagg tccacacagg cgacgggctc acggtaaccg    2341
atgacaaggt gtctctaaat acccaagctc ccctctcgac caccagcgcg ggcctctccc    2401
tacttctggg tcccagcctc cacttaggtg aggaggaacg actaacagta aacaccggag    2461
cgggcctcca aattagcaat aacgctctgg ccgtaaaagt aggttcaggt atcaccgtag    2521
atgctcaaaa ccagctcgct gcatccctgg gggacggtct agaaagcaga gataataaaa    2581
ctgtcgttaa ggctgggccc ggacttacaa taactaatca agctcttact gttgctaccg    2641
ggaacggcct tcaggtcaac ccggaagggc aactgcagct aaacattact gccggtcagg    2701
gcctcaactt tgcaaacaac agcctcgccg tggagctggg ctcgggcctg cattttcccc    2761
ctggccaaaa ccaagtaagc ctttatcccg gagatggaat agacatccga gataataggg    2821
tgactgtgcc cgctgggcca ggcctgagaa tgctcaacca ccaacttgcc gtagcttccg    2881
gagacggttt agaagtccac agcgacaccc tccggttaaa gctctcccac ggcctgacat    2941
ttgaaaatgg cgccgtacga gcaaaactag gaccaggact tggcacagac gactctggtc    3001
ggtccgtggt tcgcacaggt cgaggactta gagttgcaaa cggccaagtc cagatcttca    3061
gcggaagagg caccgccatc ggcactgata gcagcctcac tctcaacatc cgggcgcccc    3121
tacaattttc tggacccgcc ttgactgcta gtttgcaagg cagtggtccg attacttaca    3181
acagcaacaa tggcactttc ggtctctcta taggccccgg aatgtgggta gaccaaaaca    3241
gacttcaggt aaacccaggc gctggtttag tcttccaagg aaacaaccct gtcccaaacc    3301
ttgcggatcc gctggctatt tccgacagca aaattagtct cagtctcggt cccggcctga    3361
cccaagcttc caacgccctg actttaagtt taggaaacgg gcttgaattc tccaatcaag    3421
ccgttgctat aaaagcgggc cggggcttac gctttgagtc ttcctcacaa gctttagaga    3481
gcagcctcac agtcggaaat ggcttaacgc ttaccgatac tgtgatccgc cccaacctag    3541
gggacggcct agaggtcaga gacaataaaa tcattgttaa gctgggcgcg aatcttcgtt    3601
ttgaaaacgg agccgtaacc gccggcaccg ttaacccttc tgcgcccgag gcaccaccaa    3661
ctctcactgc agaaccaccc ctccgagcct ccaactccca tcttcaactg tccctatcgg    3721
agggcttggt tgtgcataac aacgcccttg ctctccaact gggagacggc atggaagtaa    3781
atcagcacgg acttactta agagtaggct cgggtttgca aatgcgtgac ggcatttta    3841 cagttacacc cagcggcact cctattgagc ccagactgac tgccccactg actcagacag    3901
agaatggaat cgggctcgct ctcggcgccg gcttggaatt agacgagagc gcgctccaag    3961
taaaagttgg gccggcatg cgcctgaacc ctgtagaaaa gtatgtaacc ctgctcctgg    4021
gtcctggcct tagttttggg cagccggcca acaggacaaa ttatgatgtg cgcgtttctg    4081
tggagccccc catggttttc ggacagcgtg gtcagctcac atttttagtg ggtcacggac    4141
tacacattca aaattccaaa cttcagctca atttgggaca aggcctcaga actgaccccg    4201
tcaccaacca gctggaagtg cccctcggtc aaggtttgga aattgcagac gaatcccagg    4261
```

-continued

```
ttagggttaa attgggcgat ggcctgcagt ttgattcaca agctcgcatc actaccgctc    4321
ctaacatggt cactgaaact ctgtggaccg gaacaggcag taatgctaat gttacatggc    4381
ggggctacac tgccccggc agcaaactct ttttgagtct cactcggttc agcactggtc     4441
tagttttagg aaacatgact attgacagca atgcatcctt tgggcaatac attaacgcgg    4501
gacacgaaca gatcgaatgc tttatattgt tggacaatca gggtaaccta aaagaaggat    4561
ctaacttgca aggcacttgg gaagtgaaga caaccccctc tgcttccaaa gctgcttttt    4621
tgccttccac cgcccctatac cccatcctca acgaaagccg agggagtctt cctgaaaaaa   4681
atcttgtggg catgcaagcc atactgggag gcggggcac ttgcactgtg atagccaccc     4741
tcaatggcag acgcagcaac aactatcccg cgggccagtc cataattttc gtgtggcaag    4801
aattcaacac catagcccgc caacctctga accactctac acttactttt tcttactgga    4861
cttaaataag ttggaaataa agagttaaac tgaatgttta agtgcaacag acttttattg    4921
gttttggctc acaacaaatt acaacagcat agacaagtca taccggtcaa acaacacagg    4981
ctctcgaaaa cgggctaacc gctccaagaa tctgtcacgc agacgagcaa gtcctaaatg    5041
ttttttcact ctcttcgggg ccaagttcag catgtatcgg atttctgct tacacctttt     5100
```

<210> SEQ ID NO 18
<211> LENGTH: 308
<212> TYPE: PRT
<213> ORGANISM: Bovine adenovirus type 3

<400> SEQUENCE: 18

```
Ala Val Ile Ala Glu Ile Val Arg Leu Ser Tyr Leu Ser Leu Cys Cys
 1               5                  10                  15

Phe Ser Ala Ser Ser Pro Thr Ser Met Lys Gly Phe Leu Leu Ile Phe
                20                  25                  30

Ser Leu Leu Val His Cys Pro Leu Ile His Val Gly Thr Ile Ser Phe
            35                  40                  45

Tyr Ala Ala Arg Pro Gly Ser Glu Pro Asn Ala Thr Tyr Val Cys Asp
        50                  55                  60

Tyr Gly Ser Glu Ser Asp Tyr Asn Pro Thr Thr Val Leu Trp Leu Ala
 65                  70                  75                  80

Arg Glu Thr Asp Gly Ser Trp Ile Ser Val Leu Phe Arg His Asn Gly
                85                  90                  95

Ser Ser Thr Ala Ala Pro Gly Val Val Ala His Phe Thr Asp His Asn
            100                 105                 110

Ser Ser Ile Val Val Pro Gln Tyr Tyr Leu Leu Asn Asn Ser Leu Ser
        115                 120                 125

Lys Leu Cys Cys Ser Tyr Arg His Asn Glu Arg Ser Gln Phe Thr Cys
    130                 135                 140

Lys Gln Ala Asp Val Pro Thr Cys His Glu Pro Gly Lys Pro Leu Thr
145                 150                 155                 160

Leu Arg Val Ser Pro Ala Leu Gly Thr Ala His Gln Ala Val Thr Trp
                165                 170                 175

Phe Phe Gln Asn Val Pro Ile Ala Thr Val Tyr Arg Pro Trp Gly Asn
            180                 185                 190

Val Thr Trp Phe Cys Pro Pro Phe Met Cys Thr Phe Asn Val Ser Leu
        195                 200                 205

Asn Ser Leu Leu Ile Tyr Asn Phe Ser Asp Lys Thr Gly Gly Gln Tyr
    210                 215                 220

Thr Ala Leu Met His Ser Gly Pro Ala Ser Leu Phe Gln Leu Phe Lys
```

```
                     225                 230                 235                 240
     Pro Thr Thr Cys Val Thr Lys Val Glu Asp Pro Pro Tyr Ala Asn Asp
                     245                 250                 255

Pro Ala Ser Pro Val Trp Arg Pro Leu Leu Phe Ala Phe Val Leu Cys
                     260                 265                 270

Thr Gly Cys Ala Val Leu Leu Thr Ala Phe Gly Pro Ser Ile Leu Ser
                     275                 280                 285

Gly Thr Arg Lys Leu Ile Ser Ala Arg Phe Trp Ser Pro Glu Pro Tyr
                     290                 295                 300

Thr Thr Leu His
     305

<210> SEQ ID NO 19
<211> LENGTH: 5100
<212> TYPE: DNA
<213> ORGANISM: Bovine adenovirus type 3
<220> FEATURE:
<221> NAME/KEY: CDS
<222> LOCATION: (529)..(954)

<400> SEQUENCE: 19
cctcatcaaa caacccgtgg tgggcaccac ccacgtggaa atgcctcgca acgaagtcct      60
agaacaacat ctgacctcac atggcgctca atcgcgggc ggaggcgctg cgggcgatta     120
ctttaaaagc cccacttcag ctcgaaccct tatcccgctc accgcctcct gcttaagacc     180
agatggagtc tttcaactag gaggaggctc gcgttcatct ttcaacccc tgcaaacaga     240 ttttgccttc cacgccctgc cctccagacc gcgccacggg ggcataggat ccaggcagtt     300
tgtagaggaa tttgtgcccg ccgtctacct caaccctac tcgggaccgc cggactctta     360
tccggaccag tttatacgcc actacaacgt gtacagcaac tctgtgagcg gttatagctg     420
agattgtaag actctcctat ctgtctctgt gctgcttttc cgcttcaagc cccacaagca     480 tgaagggggtt tctgctcatc ttcagcctgc ttgtgcattg tcccctaa ttc atg ttg    537
                                                        Phe Met Leu
                                                          1 gga cca tta gct tct atg ctg caa ggc ccg ggt ctg agc cta acg cga    585
Gly Pro Leu Ala Ser Met Leu Gln Gly Pro Gly Leu Ser Leu Thr Arg
    5                  10                  15 ctt atg ttt gtg act atg gaa gcg agt cag att aca acc cca cca cgg    633
Leu Met Phe Val Thr Met Glu Ala Ser Gln Ile Thr Thr Pro Pro Arg
 20                  25                  30                  35 ttc tgt ggt tgg ctc gag aga ccg atg gct cct gga tct ctg ttc ttt    681
Phe Cys Gly Trp Leu Glu Arg Pro Met Ala Pro Gly Ser Leu Phe Phe
             40                  45                  50 tcc gtc aca acg gct cct caa ctg cag ccc ccg ggg tcg tcg cgc act    729
Ser Val Thr Thr Ala Pro Gln Leu Gln Pro Pro Gly Ser Ser Arg Thr
         55                  60                  65 tta ctg acc aca aca gca gca ttg tgg tgc ccc agt att acc tcc tca    777
Leu Leu Thr Thr Thr Ala Ala Leu Trp Cys Pro Ser Ile Thr Ser Ser
     70                  75                  80 aca act cac tct cta agc tct gct gct cat acc ggc aca acg agc gtt    825
Thr Thr His Ser Leu Ser Ser Ala Ala His Thr Gly Thr Thr Ser Val
 85                  90                  95 ctc agt tta cct gca aac aag ctg acg tcc cta cct gtc acg agc ccg    873
Leu Ser Leu Pro Ala Asn Lys Leu Thr Ser Leu Pro Val Thr Ser Pro
            100                 105                 110                 115 gca agc cgc tca ccc tcc gcg tct ccc ccg cgc tgg gaa ctg ccc acc    921
Ala Ser Arg Ser Pro Ser Ala Ser Pro Pro Arg Trp Glu Leu Pro Thr
                 120                 125                 130
```

| | |
|---|---|
| aag cag tca ctt ggt ttt ttc aaa atg tac cca tagctactgt ttaccgacct<br>Lys Gln Ser Leu Gly Phe Phe Lys Met Tyr Pro<br>            135                 140 | 974 |
| tggggcaatg taacttggtt ttgtcctccc ttcatgtgta cctttaatgt cagcctgaac | 1034 |
| tccctactta tttacaactt ttctgacaaa accgggggc aatacacagc tctcatgcac | 1094 |
| tccggacctg cttccctctt tcagctcttt aagccaacga cttgtgtcac caaggtggag | 1154 |
| gacccgccgt atgccaacga cccggcctcg cctgtgtggc gcccactgct ttttgccttc | 1214 |
| gtcctctgca ccggctgcgc ggtgttgtta accgccttcg gtccatcgat tctatccggt | 1274 |
| acccgaaagc ttatctcagc ccgcttttgg agtcccgagc cctataccac cctccactaa | 1334 |
| cagtccccc atggagccag acggagttca tgccgagcag cagtttatcc tcaatcagat | 1394 |
| ttcctgcgcc aacactgccc tccagcgtca agggaggaa ctagcttccc ttgtcatgtt | 1454 |
| gcatgcctgt aagcgtggcc tcttttgtcc agtcaaaact tacaagctca gcctcaacgc | 1514 |
| ctcggccagc gagcacagcc tgcactttga aaaagtcccc tcccgattca ccctggtcaa | 1574 |
| cactcacgcc ggagcttctg tgcgagtggc cctacaccac cagggagctt ccggcagcat | 1634 |
| ccgctgttcc tgttcccacg ccgagtgcct ccccgtcctc ctcaagaccc tctgtgcctt | 1694 |
| taacttttta gattagctga aagcaaatat aaaatggtgt gcttaccgta attctgtttt | 1754 |
| gacttgtgtg cttgatttct cccctgcgc cgtaatccag tgcccctctt caaaactctc | 1814 |
| gtaccctatg cgattcgcat aggcatattt tctaaaagct ctgaagtcaa catcactctc | 1874 |
| aaacacttct ccgttgtagg ttactttcat ctacagataa agtcatccac cggttaacat | 1934 |
| catgaagaga agtgtgcccc aggactttaa tcttgtgtat ccgtacaagg ctaagaggcc | 1994 |
| caacatcatg ccgccctttt ttgaccgcaa tggctttgtt gaaaaccaag aagccacgct | 2054 |
| agccatgctt gtggaaaagc cgctcacgtt cgacaaggaa ggtgcgctga ccctgggcgt | 2114 |
| cggacgcggc atccgcatta accccgcggg gcttctggag acaaacgacc tcgcgtccgc | 2174 |
| tgtcttccca ccgctggcct ccgatgaggc cggcaacgtc acgctcaaca tgtctgacgg | 2234 |
| gctatatact aaggacaaca agctagctgt caaagtaggt cccgggctgt ccctcgactc | 2294 |
| caataatgct ctccaggtcc acacaggcga cgggctcacg gtaaccgatg acaaggtgtc | 2354 |
| tctaaatacc caagctcccc tctcgaccac cagcgcgggc ctctccctac ttctgggtcc | 2414 |
| cagcctccac ttaggtgagg aggaacgact aacagtaaac accggagcgg gcctccaaat | 2474 |
| tagcaataac gctctggccg taaaagtagg ttcaggtatc accgtagatg ctcaaaacca | 2534 |
| gctcgctgca tccctggggg acggtctaga aagcagagat aataaaactg tcgttaaggc | 2594 |
| tgggcccgga cttacaataa ctaatcaagc tcttactgtt gctaccggga acggccttca | 2654 |
| ggtcaacccg gaagggcaac tgcagctaaa cattactgcc ggtcagggcc tcaactttgc | 2714 |
| aaacaacagc ctcgccgtgg agctgggctc gggcctgcat tttcccctg gccaaaacca | 2774 |
| agtaagcctt tatcccggag atggaataga catccgagat aataggtga ctgtgcccgc | 2834 |
| tgggccaggc ctgagaatgc tcaaccacca acttgccgta gcttccggag acggtttaga | 2894 |
| agtccacagc gacaccctcc ggttaaagct ctcccacggc ctgacatttg aaaatggcgc | 2954 |
| cgtacgagca aaactaggac caggacttgg cacagacgac tctggtcggt ccgtggttcg | 3014 |
| cacaggtcga ggacttagag ttgcaaacgg ccaagtccag atcttcagcg gaagaggcac | 3074 |
| cgccatcggc actgatagca gcctcactct caacatccgg gcgcccctac aattttctgg | 3134 |
| acccgccttg actgctagtt tgcaaggcag tggtccgatt acttacaaca gcaacaatgg | 3194 |
| cactttcggt ctctctatag gccccggaat gtgggtagac caaaacagac ttcaggtaaa | 3254 |

-continued

```
cccaggcgct ggtttagtct tccaaggaaa caaccttgtc ccaaaccttg cggatccgct     3314
ggctatttcc gacagcaaaa ttagtctcag tctcggtccc ggcctgaccc aagcttccaa     3374
cgccctgact ttaagtttag gaaacgggct tgaattctcc aatcaagccg ttgctataaa     3434
agcgggccgg ggcttacgct ttgagtcttc ctcacaagct ttagagagca gcctcacagt     3494
cggaaatggc ttaacgctta ccgatactgt gatccgcccc aacctagggg acggcctaga     3554
ggtcagagac aataaaatca ttgttaagct gggcgcgaat cttcgttttg aaaacggagc     3614
cgtaaccgcc ggcaccgtta acccttctgc gcccgaggca ccaccaactc tcactgcaga     3674 accaccccte cgagcctcca actcccatct tcaactgtcc ctatcggagg cttggttgt     3734 gcataacaac gcccttgctc tccaactggg agacggcatg gaagtaaatc agcacggact     3794
tactttaaga gtaggctcgg gtttgcaaat gcgtgacggc attttaacag ttacacccag     3854
cggcactcct attgagccca gactgactgc cccactgact cagacagaga atggaatcgg     3914
gctcgctctc ggcgccggct tggaattaga cgagagcgcg ctccaagtaa aagttgggcc     3974
cggcatgcgc ctgaaccctg tagaaaagta tgtaaccctg ctcctgggtc ctggccttag     4034
ttttgggcag ccgccaaca ggacaaatta tgatgtgcgc gtttctgtgg agcccccat     4094 ggttttcgga cagcgtggtc agctcacatt tttagtgggt cacggactac acattcaaaa     4154
ttccaaactt cagctcaatt tgggacaagg cctcagaact gaccccgtca ccaaccagct     4214
ggaagtgccc ctcggtcaag gtttggaaat tgcagacgaa tcccaggtta gggttaaatt     4274
gggcgatggc ctgcagtttg attcacaagc tcgcatcact accgctccta acatggtcac     4334
tgaaactctg tggaccggaa caggcagtaa tgctaatgtt acatggcggg gctacactgc     4394
ccccggcagc aaactctttt tgagtctcac tcggttcagc actggtctag ttttaggaaa     4454
catgactatt gacagcaatg catcctttgg gcaatacatt aacgcgggac acgaacagat     4514
cgaatgcttt atattgttgg acaatcaggg taacctaaaa gaaggatcta acttgcaagg     4574
cacttgggaa gtgaagaaca cccctctgc ttccaaagct gcttttttgc cttccaccgc     4634 cctataccc atcctcaacg aaagccgagg gagtcttcct ggaaaaaatc ttgtgggcat     4694
gcaagccata ctgggaggcg ggggcacttg cactgtgata gccaccctca atggcagacg     4754
cagcaacaac tatcccgcgg gccagtccat aatttcgtg tggcaagaat tcaacaccat     4814
agcccgccaa cctctgaacc actctacact tactttttct tactggactt aaataagttg     4874
gaaataaaga gttaaactga atgtttaagt gcaacagact tttattggtt ttggctcaca     4934
acaaattaca acagcataga caagtcatac cggtcaaaca acacaggctc tcgaaaacgg     4994
gctaaccgct ccaagaatct gtcacgcaga cgagcaagtc ctaaatgttt tttcactctc     5054
ttcggggcca agttcagcat gtatcggatt ttctgcttac accttt                   5100
```

<210> SEQ ID NO 20
<211> LENGTH: 142
<212> TYPE: PRT
<213> ORGANISM: Bovine adenovirus type 3

<400> SEQUENCE: 20

```
Phe Met Leu Gly Pro Leu Ala Ser Met Leu Gln Gly Pro Gly Leu Ser
 1               5                  10                  15

Leu Thr Arg Leu Met Phe Val Thr Met Glu Ala Ser Gln Ile Thr Thr
             20                  25                  30

Pro Pro Arg Phe Cys Gly Trp Leu Glu Arg Pro Met Ala Pro Gly Ser
         35                  40                  45

Leu Phe Phe Ser Val Thr Thr Ala Pro Gln Leu Gln Pro Pro Gly Ser
```

|     |     |     |     | 50  |     |     |     |     | 55  |     |     |     |     | 60  |     |     |
| --- | --- | --- | --- | --- | --- | --- | --- | --- | --- | --- | --- | --- | --- | --- | --- | --- |
| Ser | Arg | Thr | Leu | Leu | Thr | Thr | Thr | Ala | Ala | Leu | Trp | Cys | Pro | Ser | Ile |
| 65  |     |     |     |     | 70  |     |     |     |     | 75  |     |     |     |     | 80  |

Thr Ser Ser Thr Thr His Ser Leu Ser Ser Ala Ala His Thr Gly Thr
                85                      90                      95

Thr Ser Val Leu Ser Leu Pro Ala Asn Lys Leu Thr Ser Leu Pro Val
            100                     105                     110

Thr Ser Pro Ala Ser Arg Ser Pro Ser Ala Ser Pro Pro Arg Trp Glu
                115                     120                    125

Leu Pro Thr Lys Gln Ser Leu Gly Phe Phe Lys Met Tyr Pro
      130                     135                     140

<210> SEQ ID NO 21
<211> LENGTH: 5100
<212> TYPE: DNA
<213> ORGANISM: Bovine adenovirus type 3
<220> FEATURE:
<221> NAME/KEY: CDS
<222> LOCATION: (1246)..(1707)

<400> SEQUENCE: 21

```
cctcatcaaa caacccgtgg tgggcaccac ccacgtggaa atgcctcgca acgaagtcct      60
agaacaacat ctgacctcac atggcgctca atcgcgggc ggaggcgctg cgggcgatta     120
ctttaaaagc cccacttcag ctcgaaccct tatcccgctc accgcctcct gcttaagacc     180
agatggagtc tttcaactag gaggaggctc gcgttcatct ttcaaccccc tgcaaacaga     240
ttttgccttc cacgccctgc cctccagacc gcgccacggg ggcataggat ccaggcagtt     300
tgtagaggaa tttgtgcccg ccgtctacct caaccccctac tcgggaccgc cggactctta     360
tccggaccag tttatacgcc actacaacgt gtacagcaac tctgtgagcg gttatagctg     420
agattgtaag actctcctat ctgtctctgt gctgcttttc cgcttcaagc ccacaagca     480
tgaagggggtt tctgctcatc ttcagcctgc ttgtgcattg tcccctaatt catgttggga     540
ccattagctt ctatgctgca aggcccgggt ctgagcctaa cgcgacttat gtttgtgact     600
atggaagcga gtcagattac aaccccacca cggttctgtg gttggctcga gagaccgatg     660
gctcctggat ctctgttctt ttccgtcaca acggctcctc aactgcagcc cccggggtcg     720
tcgcgcactt tactgaccac aacagcagca ttgtggtgcc ccagtattac ctcctcaaca     780
actcactctc taagctctgc tgctcatacc ggcacaacga gcgttctcag tttacctgca     840
acaagctga cgtccctacc tgtcacgagc ccggcaagcc gctcaccctc cgcgtctccc     900
ccgcgctggg aactgcccac caagcagtca cttggttttt tcaaaatgta cccatagcta     960
ctgtttaccg accttgggc aatgtaactt ggttttgtcc tcccttcatg tgtacccttta    1020
atgtcagcct gaactcccta cttatttaca acttttctga caaaaccggg gggcaataca    1080
cagctctcat gcactccgga cctgcttccc tctttcagct ctttaagcca acgacttgtg    1140
tcaccaaggt ggaggacccg ccgtatgcca acgacccggc ctcgcctgtg tggcgcccac    1200
tgcttttgc cttcgtcctc tgcaccggct gcgcggtgtt gttaa ccg cct tcg gtc    1257
                                             Pro Pro Ser Val
                                                    1
cat cga ttc tat ccg gta ccc gaa agc tta tct cag ccc gct ttt gga    1305
His Arg Phe Tyr Pro Val Pro Glu Ser Leu Ser Gln Pro Ala Phe Gly
 5                  10                  15                  20 gtc ccg agc cct ata cca ccc tcc act aac agt ccc ccc atg gag cca    1353
Val Pro Ser Pro Ile Pro Pro Ser Thr Asn Ser Pro Pro Met Glu Pro
            25                  30                  35
```

```
gac gga gtt cat gcc gag cag cag ttt atc ctc aat cag att tcc tgc    1401
Asp Gly Val His Ala Glu Gln Gln Phe Ile Leu Asn Gln Ile Ser Cys
            40                  45                  50 gcc aac act gcc ctc cag cgt caa agg gag gaa cta gct tcc ctt gtc    1449
Ala Asn Thr Ala Leu Gln Arg Gln Arg Glu Glu Leu Ala Ser Leu Val
        55                  60                  65 atg ttg cat gcc tgt aag cgt ggc ctc ttt tgt cca gtc aaa act tac    1497
Met Leu His Ala Cys Lys Arg Gly Leu Phe Cys Pro Val Lys Thr Tyr
    70                  75                  80 aag ctc agc ctc aac gcc tcg gcc agc gag cac agc ctg cac ttt gaa    1545
Lys Leu Ser Leu Asn Ala Ser Ala Ser Glu His Ser Leu His Phe Glu
85                  90                  95                 100 aaa agt ccc tcc cga ttc acc ctg gtc aac act cac gcc gga gct tct    1593
Lys Ser Pro Ser Arg Phe Thr Leu Val Asn Thr His Ala Gly Ala Ser
                105                 110                 115 gtg cga gtg gcc cta cac cac cag gga gct tcc ggc agc atc cgc tgt    1641
Val Arg Val Ala Leu His His Gln Gly Ala Ser Gly Ser Ile Arg Cys
            120                 125                 130 tcc tgt tcc cac gcc gag tgc ctc ccc gtc ctc ctc aag acc ctc tgt    1689
Ser Cys Ser His Ala Glu Cys Leu Pro Val Leu Leu Lys Thr Leu Cys
        135                 140                 145 gcc ttt aac ttt tta gat tagctgaaag caaatataaa atggtgtgct           1737
Ala Phe Asn Phe Leu Asp
    150 taccgtaatt ctgttttgac ttgtgtgctt gatttctccc cctgcgccgt aatccagtgc  1797 ccctcttcaa aactctcgta ccctatgcga ttcgcatagg catattttct aaaagctctg  1857 aagtcaacat cactctcaaa cacttctccg ttgtaggtta ctttcatcta cagataaagt  1917 catccaccgg ttaacatcat gaagagaagt gtgccccagg actttaatct tgtgtatccg  1977 tacaaggcta agaggcccaa catcatgccg ccctttttg accgcaatgg ctttgttgaa   2037 aaccaagaag ccacgctagc catgcttgtg gaaaagccgc tcacgttcga caaggaaggt  2097 gcgctgaccc tgggcgtcgg acgcggcatc cgcattaacc ccgcgggct tctggagaca   2157 aacgacctcg cgtccgctgt cttcccaccg ctggcctccg atgaggccgg caacgtcacg  2217 ctcaacatgt ctgacgggct atatactaag gacaacaagc tagctgtcaa agtaggtccc  2277 gggctgtccc tcgactccaa taatgctctc caggtccaca caggcgacgg gctcacggta  2337 accgatgaca aggtgtctct aaatacccaa gctcccctct cgaccaccag cgcgggcctc  2397 tccctacttc tgggtcccag cctccactta ggtgaggagg aacgactaac agtaaacacc  2457 ggagcgggcc tccaaattag caataacgct ctggccgtaa aagtaggttc aggtatcacc  2517 gtagatgctc aaaaccagct cgctgcatcc ctggggggacg gtctagaaag cagagataat  2577 aaaactgtcg ttaaggctgg gcccggactt acaataacta atcaagctct tactgttgct  2637 accgggaacg gccttcaggt caacccggaa gggcaactgc agctaaacat tactgccggt  2697 cagggcctca actttgcaaa caacagcctc gccgtggagc tgggctcggg cctgcatttt  2757 cccccctggcc aaaaccaagt aagcctttat cccggagatg aatagacat ccgagataat   2817 agggtgactg tgcccgctgg gccaggcctg agaatgctca accaccaact tgccgtagct  2877 tccggagacg gtttagaagt ccacagcgac accctccggt taaagctctc ccacggcctg  2937 acatttgaaa atggcgccgt acgagcaaaa ctaggaccag gacttggcac agacgactct  2997 ggtcggtccg tggttcgcac aggtcgagga cttagagttg caaacggcca agtccagatc  3057 ttcagcggaa gaggcaccgc catcggcact gatagcagcc tcactctcaa catccgggcg  3117 cccctacaat tttctggacc cgccttgact gctagtttgc aaggcagtgg tccgattact  3177
```

```
tacaacagca acaatggcac tttcggtctc tctataggcc ccggaatgtg ggtagaccaa    3237
aacagacttc aggtaaaccc aggcgctggt ttagtcttcc aaggaaacaa ccttgtccca    3297
aaccttgcgg atccgctggc tatttccgac agcaaaatta gtctcagtct cggtcccggc    3357
ctgacccaag cttccaacgc cctgacttta agtttaggaa acgggcttga attctccaat    3417
caagccgttg ctataaaagc gggccggggc ttacgctttg agtcttcctc acaagctttta   3477 gagagcagcc tcacagtcgg aaatggctta acgcttaccg atactgtgat ccgcccaac     3537 ctaggggacg gcctagaggt cagagacaat aaaatcattg ttaagctggg cgcgaatctt    3597
cgttttgaaa acggagccgt aaccgccggc accgttaacc cttctgcgcc cgaggcacca    3657
ccaactctca ctgcagaacc accctccga gcctccaact cccatcttca actgtcccta     3717
tcggagggct tggttgtgca taacaacgcc cttgctctcc aactgggaga cggcatggaa    3777
gtaaatcagc acggacttac tttaagagta ggctcgggtt tgcaaatgcg tgacggcatt    3837
ttaacagtta cacccagcgg cactcctatt gagcccgac tgactgcccc actgactcag     3897
acagagaatg gaatcgggct cgctctcggc gccggcttgg aattagacga gagcgcgctc    3957
caagtaaaag ttgggcccgg catgcgcctg aaccctgtag aaaagtatgt aaccctgctc    4017
ctgggtcctg gccttagttt tgggcagccg gccaacagga caaattatga tgtgcgcgtt    4077
tctgtggagc cccccatggt tttcggacag cgtggtcagc tcacattttt agtgggtcac    4137
ggactacaca ttcaaaattc caacttcag ctcaatttgg acaaggcct cagaactgac      4197 cccgtcacca accagctgga agtgccctc ggtcaaggtt tggaaattgc agacgaatcc     4257
caggttaggg ttaaattggg cgatggcctg cagtttgatt cacaagctcg catcactacc    4317
gctcctaaca tggtcactga aactctgtgg accggaacag gcagtaatgc taatgttaca    4377
tggcggggct acactgcccc cggcagcaaa ctcttttgga gtctcactcg gttcagcact    4437
ggtctagttt taggaaacat gactattgac agcaatgcat cctttgggca atacattaac    4497
gcgggacacg aacagatcga atgctttata ttgttggaca atcagggtaa cctaaaagaa    4557
ggatctaact tgcaaggcac ttgggaagtg aagaacaacc cctctgcttc caaagctgct    4617
tttttgcctt ccaccgccct atacccatc ctcaacgaaa gccgagggag tcttcctgga     4677
aaaaatcttg tgggcatgca agccatactg ggaggcgggg gcacttgcac tgtgatagcc    4737
accctcaatg gcagacgcag caacaactat cccgcgggcc agtccataat tttcgtgtgg    4797
caagaattca acaccatagc ccgccaacct ctgaaccact ctacacttac ttttttcttac   4857 tggacttaaa taagttggaa ataaagagtt aaactgaatg tttaagtgca acagacttt     4917 attggttttg gctcacaaca aattacaaca gcatagacaa gtcataccgg tcaaacaaca    4977
caggctctcg aaaacgggct aaccgctcca agaatctgtc acgcagacga gcaagtccta    5037 aatgttttt cactctcttc ggggccaagt tcagcatgta tcggattttc tgcttacacc     5097
ttt                                                                   5100
```

<210> SEQ ID NO 22
<211> LENGTH: 154
<212> TYPE: PRT
<213> ORGANISM: Bovine adenovirus type 3

<400> SEQUENCE: 22

Pro Pro Ser Val His Arg Phe Tyr Pro Val Pro Glu Ser Leu Ser Gln
 1               5                  10                  15

Pro Ala Phe Gly Val Pro Ser Pro Ile Pro Pro Ser Thr Asn Ser Pro
            20                  25                  30

```
Pro Met Glu Pro Asp Gly Val His Ala Glu Gln Gln Phe Ile Leu Asn
         35                  40                  45

Gln Ile Ser Cys Ala Asn Thr Ala Leu Gln Arg Gln Arg Glu Glu Leu
     50                  55                  60

Ala Ser Leu Val Met Leu His Ala Cys Lys Arg Gly Leu Phe Cys Pro
 65                  70                  75                  80

Val Lys Thr Tyr Lys Leu Ser Leu Asn Ala Ser Ala Ser Glu His Ser
                 85                  90                  95

Leu His Phe Glu Lys Ser Pro Ser Arg Phe Thr Leu Val Asn Thr His
             100                 105                 110

Ala Gly Ala Ser Val Arg Val Ala Leu His His Gln Gly Ala Ser Gly
         115                 120                 125

Ser Ile Arg Cys Ser Cys Ser His Ala Glu Cys Leu Pro Val Leu Leu
     130                 135                 140

Lys Thr Leu Cys Ala Phe Asn Phe Leu Asp
145                 150

<210> SEQ ID NO 23
<211> LENGTH: 5100
<212> TYPE: DNA
<213> ORGANISM: Bovine adenovirus type 3
<220> FEATURE:
<221> NAME/KEY: CDS
<222> LOCATION: (1439)..(1702)

<400> SEQUENCE: 23
cctcatcaaa caacccgtgg tgggcaccac ccacgtggaa atgcctcgca acgaagtcct    60
agaacaacat ctgacctcac atggcgctca atcgcgggc ggaggcgctg cgggcgatta   120
ctttaaaagc cccacttcag ctcgaaccct tatcccgctc accgcctcct gcttaagacc   180
agatggagtc tttcaactag gaggaggctc gcgttcatct ttcaaccccc tgcaaacaga   240
ttttgccttc cacgccctgc cctccagacc gcgccacggg gcataggat ccaggcagtt    300 tgtagaggaa tttgtgcccg ccgtctacct caacccctac tcgggaccgc cggactctta   360
tccggaccag tttatacgcc actacaacgt gtacagcaac tctgtgagcg ttatagctg    420 agattgtaag actctcctat ctgtctctgt gctgcttttc cgcttcaagc cccacaagca   480
tgaaggggtt tctgctcatc ttcagcctgc ttgtgcattg tccctaatt catgttggga    540 ccattagctt ctatgctgca aggcccgggt ctgagcctaa cgcgactat gtttgtgact    600 atggaagcga gtcagattac aaccccacca cggttctgtg gttggctcga gagaccgatg   660
gctcctggat ctctgttctt ttccgtcaca acggctcctc aactgcagcc ccggggtcg    720 tcgcgcactt tactgaccac aacagcagca ttgtggtgcc ccagtattac ctcctcaaca   780
actcactctc taagctctgc tgctcatacc ggcacaacga gcgttctcag tttacctgca   840
aacaagctga cgtccctacc tgtcacgagc ccggcaagcc gctcaccctc cgcgtctccc   900
ccgcgctggg aactgcccac caagcagtca cttggttttt tcaaaatgta cccatagcta   960
ctgtttaccg accttgggc aatgtaactt ggttttgtcc tcccttcatg tgtaccttta  1020
atgtcagcct gaactcccta cttatttaca acttttctga caaaaccggg gggcaataca  1080
cagctctcat gcactccgga cctgcttccc tctttcagct cttttaagcca acgacttgtg  1140 tcaccaaggt ggaggacccg ccgtatgcca acgacccggc ctcgcctgtg tggcgcccac  1200 tgcttttttgc cttcgtcctc tgcaccggct gcgcggtgtt gttaaccgcc ttcggtccat  1260
cgattctatc cggtacccga aagcttatct cagcccgctt ttggagtccc gagccctata  1320
ccaccctcca ctaacagtcc ccccatggag ccagacggag ttcatgccga gcagcagttt  1380
```

```
atcctcaatc agatttcctg cgccaacact gccctccagc gtcaaaggga ggaactag       1438 ctt ccc ttg tca tgt tgc atg cct gta agc gtg gcc tct ttt gtc cag       1486
Leu Pro Leu Ser Cys Cys Met Pro Val Ser Val Ala Ser Phe Val Gln
 1               5                   10                  15 tca aaa ctt aca agc tca gcc tca acg cct cgg cca gcg agc aca gcc       1534
Ser Lys Leu Thr Ser Ser Ala Ser Thr Pro Arg Pro Ala Ser Thr Ala
             20                  25                  30 tgc act ttg aaa aaa gtc cct ccc gat tca ccc tgg tca aca ctc acg       1582
Cys Thr Leu Lys Lys Val Pro Pro Asp Ser Pro Trp Ser Thr Leu Thr
         35                  40                  45 ccg gag ctt ctg tgc gag tgg ccc tac acc acc agg gag ctt ccg gca       1630
Pro Glu Leu Leu Cys Glu Trp Pro Tyr Thr Thr Arg Glu Leu Pro Ala
     50                  55                  60 gca tcc gct gtt cct gtt ccc acg ccg agt gcc tcc ccg tcc tcc tca       1678
Ala Ser Ala Val Pro Val Pro Thr Pro Ser Ala Ser Pro Ser Ser Ser
 65              70                  75                  80 aga ccc tct gtg cct tta act ttt tagattagct gaaagcaaat ataaatggt       1732
Arg Pro Ser Val Pro Leu Thr Phe
                 85 gtgcttaccg taattctgtt ttgacttgtg tgcttgattt ctcccctgc gccgtaatcc      1792 agtgccctc ttcaaaactc tcgtacccta tgcgattcgc ataggcatat tttctaaaag      1852 ctctgaagtc aacatcactc tcaaacactt ctccgttgta ggttactttc atctacagat    1912 aaagtcatcc accggttaac atcatgaaga gaagtgtgcc ccaggacttt aatcttgtgt    1972 atccgtacaa ggctaagagg cccaacatca tgccgccctt ttttgaccgc aatggctttg   2032 ttgaaaacca agaagccacg ctagccatgc ttgtggaaaa gccgctcacg ttcgacaagg    2092 aaggtgcgct gaccctgggc gtcggacgcg gcatccgcat taaccccgcg gggcttctgg   2152 agacaaacga cctcgcgtcc gctgtcttcc caccgctggc ctccgatgag gccggcaacg    2212 tcacgctcaa catgtctgac gggctatata ctaaggacaa caagctagct gtcaaagtag   2272 gtcccgggct gtccctcgac tccaataatg ctctccaggt ccacacaggc gacgggctca   2332 cggtaaccga tgacaaggtg tctctaaata cccaagctcc cctctcgacc accagcgcgg   2392 gcctctccct acttctgggt cccagcctcc acttaggtga ggaggaacga ctaacagtaa    2452 acaccggagc gggcctccaa attagcaata acgctctggc cgtaaaagta ggttcaggta    2512 tcaccgtaga tgctcaaaac cagctcgctg catccctggg ggacggtcta gaaagcagag    2572 ataataaaac tgtcgttaag gctgggcccg gacttacaat aactaatcaa gctcttactg   2632 ttgctaccgg gaacggcctt caggtcaacc cggaagggca actgcagcta acattactg     2692 ccggtcaggg cctcaacttt gcaaacaaca gcctcgccgt ggagctgggc tcgggcctgc   2752 attttcccc tggccaaaac caagtaagcc tttatcccgg agatggaata gacatccgag     2812 ataatagggt gactgtgccc gctgggccag gcctgagaat gctcaaccac caacttgccg    2872 tagcttccgg agacggttta gaagtccaca gcgacaccct ccggttaaag ctctcccacg    2932 gcctgacatt tgaaaatggc gccgtacgag caaaactagg accaggactt ggcacagacg   2992 actctggtcg gtccgtggtt cgcacaggtc gaggacttag agttgcaaac ggccaagtcc    3052 agatcttcag cggaagaggc accgccatcg gcactgatag cagcctcact ctcaacatcc   3112 gggcgcccct acaattttct ggacccgcct tgactgctag tttgcaaggc agtggtccga   3172 ttacttacaa cagcaacaat ggcactttcg gtctctctat aggcccccgga atgtgggtag   3232 accaaaacag acttcaggta aacccaggcg ctggtttagt cttccaagga aacaaccttg   3292 tcccaaacct tgcggatccg ctggctattt ccgacagcaa aattagtctc agtctcggtc    3352
```

-continued

```
ccggcctgac ccaagcttcc aacgccctga ctttaagttt aggaaacggg cttgaattct    3412
ccaatcaagc cgttgctata aaagcgggcc ggggcttacg ctttgagtct tcctcacaag    3472
ctttagagag cagcctcaca gtcggaaatg cttaacgct taccgatact gtgatccgcc     3532
ccaacctagg ggacggccta gaggtcagag acaataaaat cattgttaag ctgggcgcga    3592
atcttcgttt tgaaaacgga gccgtaaccg ccggcaccgt taacccttct cgcccgagg     3652 caccaccaac tctcactgca gaaccacccc tccgagcctc caactcccat cttcaactgt    3712
ccctatcgga gggcttggtt gtgcataaca acgcccttgc tctccaactg ggagacggca    3772
tggaagtaaa tcagcacgga cttactttaa gagtaggctc gggtttgcaa atgcgtgacg    3832
gcattttaac agttacaccc agcggcactc ctattgagcc cagactgact gccccactga    3892
ctcagacaga gaatggaatc gggctcgctc tcggcgccgg cttggaatta gacgagagcg    3952
cgctccaagt aaaagttggg cccggcatgc gcctgaaccc tgtagaaaag tatgtaaccc    4012
tgctcctggg tcctggcctt agttttgggc agccggccaa caggacaaat tatgatgtgc    4072
gcgtttctgt ggagccccc atggttttcg gacagcgtgg tcagctcaca ttttttagtgg    4132 gtcacggact acacattcaa aattccaaac ttcagctcaa tttgggacaa ggcctcagaa    4192
ctgaccccgt caccaaccag ctggaagtgc ccctcggtca aggtttggaa attgcagacg    4252
aatcccaggt tagggttaaa ttgggcgatg gcctgcagtt tgattcacaa gctcgcatca    4312
ctaccgctcc taacatggtc actgaaactc tgtggaccgg aacaggcagt aatgctaatg    4372
ttacatggcg gggctacact gcccccggca gcaaactctt tttgagtctc actcggttca    4432
gcactggtct agttttagga aacatgacta ttgacagcaa tgcatccttt gggcaataca    4492
ttaacgcggg acacgaacag atcgaatgct ttatattgtt ggacaatcag ggtaacctaa    4552
aagaaggatc taacttgcaa ggcacttggg aagtgaagaa caacccctct gcttccaaag    4612 ctgcttttt gccttccacc gccctatacc ccatcctcaa cgaaagccga gggagtcttc    4672
ctggaaaaaa tcttgtgggc atgcaagcca tactgggagg cggggggcact tgcactgtga    4732 tagccaccct caatggcaga cgcagcaaca actatcccgc gggccagtcc ataattttcg    4792
tgtggcaaga attcaacacc atagcccgcc aacctctgaa ccactctaca cttacttttt    4852
cttactggac ttaaataagt tggaaataaa gagttaaact gaatgtttaa gtgcaacaga    4912
cttttattgg ttttggctca caacaaatta caacagcata gacaagtcat accggtcaaa    4972
caacacaggc tctcgaaaac gggctaaccg ctccaagaat ctgtcacgca gacgagcaag    5032
tcctaaatgt tttttcactc tcttcggggc caagttcagc atgtatcgga ttttctgctt    5092
acacctttt                                                           5100
```

<210> SEQ ID NO 24
<211> LENGTH: 88
<212> TYPE: PRT
<213> ORGANISM: Bovine adenovirus type 3

<400> SEQUENCE: 24

```
Leu Pro Leu Ser Cys Cys Met Pro Val Ser Val Ala Ser Phe Val Gln
 1               5                  10                  15

Ser Lys Leu Thr Ser Ser Ala Ser Thr Pro Arg Pro Ala Ser Thr Ala
            20                  25                  30

Cys Thr Leu Lys Lys Val Pro Asp Ser Pro Trp Ser Thr Leu Thr
        35                  40                  45

Pro Glu Leu Leu Cys Glu Trp Pro Tyr Thr Thr Arg Glu Leu Pro Ala
    50                  55                  60
```

Ala Ser Ala Val Pro Val Pro Thr Pro Ser Ala Ser Pro Ser Ser Ser
 65                  70                  75                  80

Arg Pro Ser Val Pro Leu Thr Phe
                 85

<210> SEQ ID NO 25
<211> LENGTH: 5100
<212> TYPE: DNA
<213> ORGANISM: Bovine adenovirus type 3
<220> FEATURE:
<221> NAME/KEY: CDS
<222> LOCATION: (1915)..(4863)

<400> SEQUENCE: 25

| | | | | | |
|---|---|---|---|---|---|
| cctcatcaaa | caacccgtgg | tgggcaccac | ccacgtggaa | atgcctcgca acgaagtcct | 60 |
| agaacaacat | ctgacctcac | atggcgctca | aatcgcgggc | ggaggcgctg cgggcgatta | 120 |
| cttaaaagc | cccacttcag | ctcgaaccct | atcccgctc | accgcctcct gcttaagacc | 180 |
| agatggagtc | tttcaactag | gaggaggctc | gcgttcatct | ttcaaccccc tgcaaacaga | 240 |
| ttttgccttc | cacgccctgc | cctccagacc | gcgccacggg | ggcataggat ccaggcagtt | 300 |
| tgtagaggaa | tttgtgcccg | ccgtctacct | caaccctac | tcgggaccgc cggactctta | 360 |
| tccggaccag | tttatacgcc | actacaacgt | gtacagcaac | tctgtgagcg gttatagctg | 420 |
| agattgtaag | actctcctat | ctgtctctgt | gctgcttttc | cgcttcaagc cccacaagca | 480 |
| tgaagggggtt | tctgctcatc | ttcagcctgc | ttgtgcattg | tcccctaatt catgttggga | 540 |
| ccattagctt | ctatgctgca | aggcccgggt | ctgagcctaa | cgcgacttat gtttgtgact | 600 |
| atggaagcga | gtcagattac | aaccccacca | cggttctgtg | gttggctcga gagaccgatg | 660 |
| gctcctggat | ctctgttctt | ttccgtcaca | acggctcctc | aactgcagcc ccgggggtcg | 720 |
| tcgcgcactt | tactgaccac | aacagcagca | ttgtggtgcc | ccagtattac ctcctcaaca | 780 |
| actcactctc | taagctctgc | tgctcatacc | ggcacaacga | gcgttctcag tttacctgca | 840 |
| aacaagctga | cgtccctacc | tgtcacgagc | ccggcaagcc | gctcaccctc cgcgtctccc | 900 |
| ccgcgctggg | aactgcccac | caagcagtca | cttggttttt | tcaaaatgta cccatagcta | 960 |
| ctgtttaccg | accttggggc | aatgtaactt | ggttttgtcc | tcccttcatg tgtacccttta | 1020 |
| atgtcagcct | gaactcccta | cttatttaca | acttttctga | caaaaccggg gggcaataca | 1080 |
| cagctctcat | gcactccgga | cctgcttccc | tctttcagct | ctttaagcca acgacttgtg | 1140 |
| tcaccaaggt | ggaggacccg | ccgtatgcca | acgacccggc | ctcgcctgtg tggcgcccac | 1200 |
| tgcttttttgc | cttcgtcctc | tgcaccggct | gcgcggtgtt | gttaaccgcc ttcggtccat | 1260 |
| cgattctatc | cggtacccga | aagcttatct | cagcccgctt | ttggagtccc gagccctata | 1320 |
| ccaccctcca | ctaacagtcc | ccccatggag | ccagacggag | ttcatgccga gcagcagttt | 1380 |
| atcctcaatc | agatttcctg | cgccaacact | gccctccagc | gtcaaaggga ggaactagct | 1440 |
| tcccttgtca | tgttgcatgc | ctgtaagcgt | ggcctctttt | gtccagtcaa aacttacaag | 1500 |
| ctcagcctca | acgcctcggc | cagcgagcac | agcctgcact | ttgaaaaaag tccctcccga | 1560 |
| ttcaccctgg | tcaacactca | cgccggagct | tctgtgcgag | tggccctaca ccaccaggga | 1620 |
| gcttccggca | gcatccgctg | ttcctgttcc | cacgccgagt | gcctcccgt cctcctcaag | 1680 |
| accctctgtg | cctttaactt | tttagattag | ctgaaagcaa | atataaaatg gtgtgcttac | 1740 |
| cgtaattctg | ttttgacttg | tgtgcttgat | ttctcccct | gcgccgtaat ccagtgcccc | 1800 |
| tcttcaaaac | tctcgtaccc | tatgcgattc | gcataggcat | attttctaaa agctctgaag | 1860 |

-continued

```
tcaacatcac tctcaaacac ttctccgttg taggttactt tcatctacag ataa agt           1917
                                                              Ser
                                                                1 cat cca ccg gtt aac atc atg aag aga agt gtg ccc cag gac ttt aat           1965
His Pro Pro Val Asn Ile Met Lys Arg Ser Val Pro Gln Asp Phe Asn
          5                  10                  15 ctt gtg tat ccg tac aag gct aag agg ccc aac atc atg ccg ccc ttt           2013
Leu Val Tyr Pro Tyr Lys Ala Lys Arg Pro Asn Ile Met Pro Pro Phe
         20                  25                  30 ttt gac cgc aat ggc ttt gtt gaa aac caa gaa gcc acg cta gcc atg           2061
Phe Asp Arg Asn Gly Phe Val Glu Asn Gln Glu Ala Thr Leu Ala Met
 35                  40                  45 ctt gtg gaa aag ccg ctc acg ttc gac aag gaa ggt gcg ctc acc ctg           2109
Leu Val Glu Lys Pro Leu Thr Phe Asp Lys Glu Gly Ala Leu Thr Leu
 50                  55                  60                  65 ggc gtc gga cgc ggc atc cgc att aac ccc gcg ggg ctt ctg gag aca           2157
Gly Val Gly Arg Gly Ile Arg Ile Asn Pro Ala Gly Leu Leu Glu Thr
             70                  75                  80 aac gac ctc gcg tcc gct gtc ttc cca ccg ctg gcc tcc gat gag gcc           2205
Asn Asp Leu Ala Ser Ala Val Phe Pro Pro Leu Ala Ser Asp Glu Ala
                 85                  90                  95 ggc aac gtc acg ctc aac atg tct gac ggg cta tat act aag gac aac           2253
Gly Asn Val Thr Leu Asn Met Ser Asp Gly Leu Tyr Thr Lys Asp Asn
                100                 105                 110 aag cta gct gtc aaa gta ggt ccc ggg ctg tcc ctc gac tcc aat aat           2301
Lys Leu Ala Val Lys Val Gly Pro Gly Leu Ser Leu Asp Ser Asn Asn
115                 120                 125 gct ctc cag gtc cac aca ggc gac ggg ctc acg gta acc gat gac aag           2349
Ala Leu Gln Val His Thr Gly Asp Gly Leu Thr Val Thr Asp Asp Lys
130                 135                 140                 145 gtg tct cta aat acc caa gct ccc ctc tcg acc acc agc gcg ggc ctc           2397
Val Ser Leu Asn Thr Gln Ala Pro Leu Ser Thr Thr Ser Ala Gly Leu
                150                 155                 160 tcc cta ctt ctg ggt ccc agc ctc cac tta ggt gag gag gaa cga cta           2445
Ser Leu Leu Leu Gly Pro Ser Leu His Leu Gly Glu Glu Glu Arg Leu
            165                 170                 175 aca gta aac acc gga gcg ggc ctc caa att agc aat aac gct ctg gcc           2493
Thr Val Asn Thr Gly Ala Gly Leu Gln Ile Ser Asn Asn Ala Leu Ala
                180                 185                 190 gta aaa gta ggt tca ggt atc acc gta gat gct caa aac cag ctc gct           2541
Val Lys Val Gly Ser Gly Ile Thr Val Asp Ala Gln Asn Gln Leu Ala
195                 200                 205 gca tcc ctg ggg gac ggt cta gaa agc aga gat aat aaa act gtc gtt           2589
Ala Ser Leu Gly Asp Gly Leu Glu Ser Arg Asp Asn Lys Thr Val Val
210                 215                 220                 225 aag gct ggg ccc gga ctt aca ata act aat caa gct ctt act gtt gct           2637
Lys Ala Gly Pro Gly Leu Thr Ile Thr Asn Gln Ala Leu Thr Val Ala
                230                 235                 240 acc ggg aac ggc ctt cag gtc aac ccg gaa ggg caa ctg cag cta aac           2685
Thr Gly Asn Gly Leu Gln Val Asn Pro Glu Gly Gln Leu Gln Leu Asn
            245                 250                 255 att act gcc ggt cag ggc ctc aac ttt gca aac aac agc ctc gcc gtg           2733
Ile Thr Ala Gly Gln Gly Leu Asn Phe Ala Asn Asn Ser Leu Ala Val
                260                 265                 270 gag ctg ggc tcg ggc ctg cat ttt ccc cct ggc caa aac caa gta agc           2781
Glu Leu Gly Ser Gly Leu His Phe Pro Pro Gly Gln Asn Gln Val Ser
275                 280                 285 ctt tat ccc gga gat gga ata gac atc cga gat aat agg gtg act gtg           2829
Leu Tyr Pro Gly Asp Gly Ile Asp Ile Arg Asp Asn Arg Val Thr Val
290                 295                 300                 305
```

```
ccc gct ggg cca ggc ctg aga atg ctc aac cac caa ctt gcc gta gct   2877
Pro Ala Gly Pro Gly Leu Arg Met Leu Asn His Gln Leu Ala Val Ala
            310                 315                 320 tcc gga gac ggt tta gaa gtc cac agc gac acc ctc cgg tta aag ctc   2925
Ser Gly Asp Gly Leu Glu Val His Ser Asp Thr Leu Arg Leu Lys Leu
            325                 330                 335 tcc cac ggc ctg aca ttt gaa aat ggc gcc gta cga gca aaa cta gga   2973
Ser His Gly Leu Thr Phe Glu Asn Gly Ala Val Arg Ala Lys Leu Gly
            340                 345                 350 cca gga ctt ggc aca gac gac tct ggt cgg tcc gtg gtt cgc aca ggt   3021
Pro Gly Leu Gly Thr Asp Asp Ser Gly Arg Ser Val Val Arg Thr Gly
        355                 360                 365 cga gga ctt aga gtt gca aac ggc caa gtc cag atc ttc agc gga aga   3069
Arg Gly Leu Arg Val Ala Asn Gly Gln Val Gln Ile Phe Ser Gly Arg
370                 375                 380                 385 ggc acc gcc atc ggc act gat agc agc ctc act ctc aac atc cgg gcg   3117
Gly Thr Ala Ile Gly Thr Asp Ser Ser Leu Thr Leu Asn Ile Arg Ala
                390                 395                 400 ccc cta caa ttt tct gga ccc gcc ttg act gct agt ttg caa ggc agt   3165
Pro Leu Gln Phe Ser Gly Pro Ala Leu Thr Ala Ser Leu Gln Gly Ser
            405                 410                 415 ggt ccg att act tac aac agc aac aat ggc act ttc ggt ctc tct ata   3213
Gly Pro Ile Thr Tyr Asn Ser Asn Asn Gly Thr Phe Gly Leu Ser Ile
            420                 425                 430 ggc ccc gga atg tgg gta gac caa aac aga ctt cag gta aac cca ggc   3261
Gly Pro Gly Met Trp Val Asp Gln Asn Arg Leu Gln Val Asn Pro Gly
435                 440                 445 gct ggt tta gtc ttc caa gga aac aac ctt gtc cca aac ctt gcg gat   3309
Ala Gly Leu Val Phe Gln Gly Asn Asn Leu Val Pro Asn Leu Ala Asp
450                 455                 460                 465 ccg ctg gct att tcc gac agc aaa att agt ctc agt ctc ggt ccc ggc   3357
Pro Leu Ala Ile Ser Asp Ser Lys Ile Ser Leu Ser Leu Gly Pro Gly
                470                 475                 480 ctg acc caa gct tcc aac gcc ctg act tta agt tta gga aac ggg ctt   3405
Leu Thr Gln Ala Ser Asn Ala Leu Thr Leu Ser Leu Gly Asn Gly Leu
            485                 490                 495 gaa ttc tcc aat caa gcc gtt gct ata aaa gcg ggc cgg ggc tta cgc   3453
Glu Phe Ser Asn Gln Ala Val Ala Ile Lys Ala Gly Arg Gly Leu Arg
            500                 505                 510 ttt gag tct tcc tca caa gct tta gag agc agc ctc aca gtc gga aat   3501
Phe Glu Ser Ser Ser Gln Ala Leu Glu Ser Ser Leu Thr Val Gly Asn
515                 520                 525 ggc tta acg ctt acc gat act gtg atc cgc ccc aac cta ggg gac ggc   3549
Gly Leu Thr Leu Thr Asp Thr Val Ile Arg Pro Asn Leu Gly Asp Gly
530                 535                 540                 545 cta gag gtc aga gac aat aaa atc att gtt aag ctg ggc gcg aat ctt   3597
Leu Glu Val Arg Asp Asn Lys Ile Ile Val Lys Leu Gly Ala Asn Leu
                550                 555                 560 cgt ttt gaa aac gga gcc gta acc gcc ggc acc gtt aac cct tct gcg   3645
Arg Phe Glu Asn Gly Ala Val Thr Ala Gly Thr Val Asn Pro Ser Ala
            565                 570                 575 ccc gag gca cca cca act ctc act gca gaa cca ccc ctc cga gcc tcc   3693
Pro Glu Ala Pro Pro Thr Leu Thr Ala Glu Pro Pro Leu Arg Ala Ser
            580                 585                 590 aac tcc cat ctt caa ctg tcc cta tcg gag ggc ttg gtt gtg cat aac   3741
Asn Ser His Leu Gln Leu Ser Leu Ser Glu Gly Leu Val Val His Asn
            595                 600                 605 aac gcc ctt gct ctc caa ctg gga gac ggc atg gaa gta aat cag cac   3789
Asn Ala Leu Ala Leu Gln Leu Gly Asp Gly Met Glu Val Asn Gln His
610                 615                 620                 625
```

| | |
|---|---|
| gga ctt act tta aga gta ggc tcg ggt ttg caa atg cgt gac ggc att<br>Gly Leu Thr Leu Arg Val Gly Ser Gly Leu Gln Met Arg Asp Gly Ile<br>630                    635                        640 | 3837 |
| tta aca gtt aca ccc agc ggc act cct att gag ccc aga ctg act gcc<br>Leu Thr Val Thr Pro Ser Gly Thr Pro Ile Glu Pro Arg Leu Thr Ala<br>645                    650                       655 | 3885 |
| cca ctg act cag aca gag aat gga atc ggg ctc gct ctc ggc gcc ggc<br>Pro Leu Thr Gln Thr Glu Asn Gly Ile Gly Leu Ala Leu Gly Ala Gly<br>660                    665                       670 | 3933 |
| ttg gaa tta gac gag agc gcg ctc caa gta aaa gtt ggg ccc ggc atg<br>Leu Glu Leu Asp Glu Ser Ala Leu Gln Val Lys Val Gly Pro Gly Met<br>675                    680                      685 | 3981 |
| cgc ctg aac cct gta gaa aag tat gta acc ctg ctc ctg ggt cct ggc<br>Arg Leu Asn Pro Val Glu Lys Tyr Val Thr Leu Leu Leu Gly Pro Gly<br>690                    695                      700                      705 | 4029 |
| ctt agt ttt ggg cag ccg gcc aac agg aca aat tat gat gtg cgc gtt<br>Leu Ser Phe Gly Gln Pro Ala Asn Arg Thr Asn Tyr Asp Val Arg Val<br>                    710                      715                      720 | 4077 |
| tct gtg gag ccc ccc atg gtt ttc gga cag cgt ggt cag ctc aca ttt<br>Ser Val Glu Pro Pro Met Val Phe Gly Gln Arg Gly Gln Leu Thr Phe<br>                    725                      730                      735 | 4125 |
| tta gtg ggt cac gga cta cac att caa aat tcc aaa ctt cag ctc aat<br>Leu Val Gly His Gly Leu His Ile Gln Asn Ser Lys Leu Gln Leu Asn<br>      740                    745                      750 | 4173 |
| ttg gga caa ggc ctc aga act gac ccc gtc acc aac cag ctg gaa gtg<br>Leu Gly Gln Gly Leu Arg Thr Asp Pro Val Thr Asn Gln Leu Glu Val<br>755                    760                      765 | 4221 |
| ccc ctc ggt caa ggt ttg gaa att gca gac gaa tcc cag gtt agg gtt<br>Pro Leu Gly Gln Gly Leu Glu Ile Ala Asp Glu Ser Gln Val Arg Val<br>770                    775                      780                      785 | 4269 |
| aaa ttg ggc gat ggc ctg cag ttt gat tca caa gct cgc atc act acc<br>Lys Leu Gly Asp Gly Leu Gln Phe Asp Ser Gln Ala Arg Ile Thr Thr<br>                    790                      795                      800 | 4317 |
| gct cct aac atg gtc act gaa act ctg tgg acc gga aca ggc agt aat<br>Ala Pro Asn Met Val Thr Glu Thr Leu Trp Thr Gly Thr Gly Ser Asn<br>      805                    810                      815 | 4365 |
| gct aat gtt aca tgg cgg ggc tac act gcc ccc ggc agc aaa ctc ttt<br>Ala Asn Val Thr Trp Arg Gly Tyr Thr Ala Pro Gly Ser Lys Leu Phe<br>              820                    825                      830 | 4413 |
| ttg agt ctc act cgg ttc agc act ggt cta gtt tta gga aac atg act<br>Leu Ser Leu Thr Arg Phe Ser Thr Gly Leu Val Leu Gly Asn Met Thr<br>835                    840                      845 | 4461 |
| att gac agc aat gca tcc ttt ggg caa tac att aac gcg gga cac gaa<br>Ile Asp Ser Asn Ala Ser Phe Gly Gln Tyr Ile Asn Ala Gly His Glu<br>850                    855                      860                      865 | 4509 |
| cag atc gaa tgc ttt ata ttg ttg gac aat cag ggt aac cta aaa gaa<br>Gln Ile Glu Cys Phe Ile Leu Leu Asp Asn Gln Gly Asn Leu Lys Glu<br>                    870                      875                      880 | 4557 |
| gga tct aac ttg caa ggc act tgg gaa gtg aag aac aac ccc tct gct<br>Gly Ser Asn Leu Gln Gly Thr Trp Glu Val Lys Asn Asn Pro Ser Ala<br>                885                    890                    895 | 4605 |
| tcc aaa gct gct ttt ttg cct tcc acc gcc cta tac ccc atc ctc aac<br>Ser Lys Ala Ala Phe Leu Pro Ser Thr Ala Leu Tyr Pro Ile Leu Asn<br>      900                    905                      910 | 4653 |
| gaa agc cga ggg agt ctt cct gga aaa aat ctt gtg ggc atg caa gcc<br>Glu Ser Arg Gly Ser Leu Pro Gly Lys Asn Leu Val Gly Met Gln Ala<br>      915                    920                      925 | 4701 |
| ata ctg gga ggc ggg ggc act tgc act gtg ata gcc acc ctc aat ggc<br>Ile Leu Gly Gly Gly Gly Thr Cys Thr Val Ile Ala Thr Leu Asn Gly<br>930                    935                      940                      945 | 4749 |

-continued

| | | |
|---|---|---|
| aga cgc agc aac aac tat ccc gcg ggc cag tcc ata att ttc gtg tgg<br>Arg Arg Ser Asn Asn Tyr Pro Ala Gly Gln Ser Ile Ile Phe Val Trp<br>950                          955                      960 | 4797 |
| caa gaa ttc aac acc ata gcc cgc caa cct ctg aac cac tct aca ctt<br>Gln Glu Phe Asn Thr Ile Ala Arg Gln Pro Leu Asn His Ser Thr Leu<br>          965                        970                        975 | 4845 |
| act ttt tct tac tgg act taaataagtt ggaaataaag agttaaactg<br>Thr Phe Ser Tyr Trp Thr<br>          980 | 4893 |
| aatgtttaag tgcaacagac ttttattggt tttggctcac aacaaattac aacagcatag | 4953 |
| acaagtcata ccggtcaaac aacacaggct ctcgaaaacg ggctaaccgc tccaagaatc | 5013 |
| tgtcacgcag acgagcaagt cctaaatgtt ttttcactct cttcggggcc aagttcagca | 5073 |
| tgtatcggat tttctgctta caccttt | 5100 |

<210> SEQ ID NO 26
<211> LENGTH: 983
<212> TYPE: PRT
<213> ORGANISM: Bovine adenovirus type 3

<400> SEQUENCE: 26

Ser His Pro Pro Val Asn Ile Met Lys Arg Ser Val Pro Gln Asp Phe
  1                    5                    10                    15

Asn Leu Val Tyr Pro Tyr Lys Ala Lys Arg Pro Asn Ile Met Pro Pro
                20                    25                    30

Phe Phe Asp Arg Asn Gly Phe Val Glu Asn Gln Glu Ala Thr Leu Ala
                35                    40                    45

Met Leu Val Glu Lys Pro Leu Thr Phe Asp Lys Glu Gly Ala Leu Thr
 50                     55                    60

Leu Gly Val Gly Arg Gly Ile Arg Ile Asn Pro Ala Gly Leu Leu Glu
65                   70                    75                    80

Thr Asn Asp Leu Ala Ser Ala Val Phe Pro Leu Ala Ser Asp Glu
                85                    90                    95

Ala Gly Asn Val Thr Leu Asn Met Ser Asp Gly Leu Tyr Thr Lys Asp
             100                 105                110

Asn Lys Leu Ala Val Lys Val Gly Pro Gly Leu Ser Leu Asp Ser Asn
            115                 120                125

Asn Ala Leu Gln Val His Thr Gly Asp Gly Leu Thr Val Thr Asp Asp
    130                    135                  140

Lys Val Ser Leu Asn Thr Gln Ala Pro Leu Ser Thr Thr Ser Ala Gly
145                  150                   155                    160

Leu Ser Leu Leu Gly Pro Ser Leu His Leu Gly Glu Glu Arg
               165                 170                175

Leu Thr Val Asn Thr Gly Ala Gly Leu Gln Ile Ser Asn Asn Ala Leu
            180                 185                190

Ala Val Lys Val Gly Ser Gly Ile Thr Val Asp Ala Gln Asn Gln Leu
        195                 200                205

Ala Ala Ser Leu Gly Asp Gly Leu Glu Ser Arg Asp Asn Lys Thr Val
    210                    215                  220

Val Lys Ala Gly Pro Gly Leu Thr Ile Thr Asn Gln Ala Leu Thr Val
225                  230                   235                    240

Ala Thr Gly Asn Gly Leu Gln Val Asn Pro Glu Gly Gln Leu Gln Leu
            245                 250                255

Asn Ile Thr Ala Gly Gln Gly Leu Asn Phe Ala Asn Asn Ser Leu Ala
            260                 265                270

Val Glu Leu Gly Ser Gly Leu His Phe Pro Pro Gly Gln Asn Gln Val

```
                     275                 280                 285
Ser Leu Tyr Pro Gly Asp Gly Ile Asp Ile Arg Asp Asn Arg Val Thr
    290                 295                 300

Val Pro Ala Gly Pro Gly Leu Arg Met Leu Asn His Gln Leu Ala Val
305                 310                 315                 320

Ala Ser Gly Asp Gly Leu Glu Val His Ser Asp Thr Leu Arg Leu Lys
                325                 330                 335

Leu Ser His Gly Leu Thr Phe Glu Asn Gly Ala Val Arg Ala Lys Leu
                340                 345                 350

Gly Pro Gly Leu Gly Thr Asp Asp Ser Gly Arg Ser Val Val Arg Thr
                355                 360                 365

Gly Arg Gly Leu Arg Val Ala Asn Gly Gln Val Gln Ile Phe Ser Gly
370                 375                 380

Arg Gly Thr Ala Ile Gly Thr Asp Ser Ser Leu Thr Leu Asn Ile Arg
385                 390                 395                 400

Ala Pro Leu Gln Phe Ser Gly Pro Ala Leu Thr Ala Ser Leu Gln Gly
                405                 410                 415

Ser Gly Pro Ile Thr Tyr Asn Ser Asn Gly Thr Phe Gly Leu Ser
                420                 425                 430

Ile Gly Pro Gly Met Trp Val Asp Gln Asn Arg Leu Gln Val Asn Pro
            435                 440                 445

Gly Ala Gly Leu Val Phe Gln Gly Asn Asn Leu Val Pro Asn Leu Ala
    450                 455                 460

Asp Pro Leu Ala Ile Ser Asp Ser Lys Ile Ser Leu Ser Leu Gly Pro
465                 470                 475                 480

Gly Leu Thr Gln Ala Ser Asn Ala Leu Thr Leu Ser Leu Gly Asn Gly
                485                 490                 495

Leu Glu Phe Ser Asn Gln Ala Val Ala Ile Lys Ala Gly Arg Gly Leu
                500                 505                 510

Arg Phe Glu Ser Ser Ser Gln Ala Leu Glu Ser Ser Leu Thr Val Gly
            515                 520                 525

Asn Gly Leu Thr Leu Thr Asp Thr Val Ile Arg Pro Asn Leu Gly Asp
    530                 535                 540

Gly Leu Glu Val Arg Asp Asn Lys Ile Ile Val Lys Leu Gly Ala Asn
545                 550                 555                 560

Leu Arg Phe Glu Asn Gly Ala Val Thr Ala Gly Thr Val Asn Pro Ser
                565                 570                 575

Ala Pro Glu Ala Pro Thr Leu Thr Ala Glu Pro Pro Leu Arg Ala
                580                 585                 590

Ser Asn Ser His Leu Gln Leu Ser Leu Ser Glu Gly Leu Val Val His
            595                 600                 605

Asn Asn Ala Leu Ala Leu Gln Leu Gly Asp Gly Met Glu Val Asn Gln
    610                 615                 620

His Gly Leu Thr Leu Arg Val Gly Ser Gly Leu Gln Met Arg Asp Gly
625                 630                 635                 640

Ile Leu Thr Val Thr Pro Ser Gly Thr Pro Ile Glu Pro Arg Leu Thr
                645                 650                 655

Ala Pro Leu Thr Gln Thr Glu Asn Gly Ile Gly Leu Ala Leu Gly Ala
                660                 665                 670

Gly Leu Glu Leu Asp Glu Ser Ala Leu Gln Val Lys Val Gly Pro Gly
                675                 680                 685

Met Arg Leu Asn Pro Val Glu Lys Tyr Val Thr Leu Leu Leu Gly Pro
            690                 695                 700
```

```
Gly Leu Ser Phe Gly Gln Pro Ala Asn Arg Thr Asn Tyr Asp Val Arg
705                 710                 715                 720

Val Ser Val Glu Pro Pro Met Val Phe Gly Gln Arg Gly Gln Leu Thr
            725                 730                 735

Phe Leu Val Gly His Gly Leu His Ile Gln Asn Ser Lys Leu Gln Leu
        740                 745                 750

Asn Leu Gly Gln Gly Leu Arg Thr Asp Pro Val Thr Asn Gln Leu Glu
    755                 760                 765

Val Pro Leu Gly Gln Gly Leu Glu Ile Ala Asp Glu Ser Gln Val Arg
770                 775                 780

Val Lys Leu Gly Asp Gly Leu Gln Phe Asp Ser Gln Ala Arg Ile Thr
785                 790                 795                 800

Thr Ala Pro Asn Met Val Thr Glu Thr Leu Trp Thr Gly Thr Gly Ser
                805                 810                 815

Asn Ala Asn Val Thr Trp Arg Gly Tyr Thr Ala Pro Gly Ser Lys Leu
            820                 825                 830

Phe Leu Ser Leu Thr Arg Phe Ser Thr Gly Leu Val Leu Gly Asn Met
        835                 840                 845

Thr Ile Asp Ser Asn Ala Ser Phe Gly Gln Tyr Ile Asn Ala Gly His
    850                 855                 860

Glu Gln Ile Glu Cys Phe Ile Leu Leu Asp Asn Gln Gly Asn Leu Lys
865                 870                 875                 880

Glu Gly Ser Asn Leu Gln Gly Thr Trp Glu Val Lys Asn Asn Pro Ser
                885                 890                 895

Ala Ser Lys Ala Ala Phe Leu Pro Ser Thr Ala Leu Tyr Pro Ile Leu
            900                 905                 910

Asn Glu Ser Arg Gly Ser Leu Pro Gly Lys Asn Leu Val Gly Met Gln
        915                 920                 925

Ala Ile Leu Gly Gly Gly Thr Cys Thr Val Ile Ala Thr Leu Asn
    930                 935                 940

Gly Arg Arg Ser Asn Asn Tyr Pro Ala Gly Gln Ser Ile Ile Phe Val
945                 950                 955                 960

Trp Gln Glu Phe Asn Thr Ile Ala Arg Gln Pro Leu Asn His Ser Thr
                965                 970                 975

Leu Thr Phe Ser Tyr Trp Thr
            980

<210> SEQ ID NO 27
<211> LENGTH: 227
<212> TYPE: PRT
<213> ORGANISM: Human adenovirus type 2

<400> SEQUENCE: 27

Met Ser Lys Glu Ile Pro Thr Pro Tyr Met Trp Ser Tyr Gln Pro Gln
1               5                   10                  15

Met Gly Leu Ala Ala Gly Ala Ala Gln Asp Tyr Ser Thr Arg Ile Asn
            20                  25                  30

Tyr Met Ser Ala Gly Pro His Met Ile Ser Arg Val Asn Gly Ile Arg
        35                  40                  45

Ala His Arg Asn Arg Ile Leu Leu Glu Gln Ala Ile Thr Thr Thr
    50                  55                  60

Pro Arg Asn Asn Leu Asn Pro Arg Ser Trp Pro Ala Ala Leu Val Tyr
65                  70                  75                  80

Gln Glu Ser Pro Ala Pro Thr Thr Val Val Leu Pro Arg Asp Ala Gln
            85                  90                  95
```

```
Ala Glu Val Gln Met Thr Asn Ser Gly Ala Gln Leu Ala Gly Gly Phe
            100                 105                 110
Arg His Arg Val Arg Ser Pro Gly Gln Gly Ile Thr His Leu Lys Ile
        115                 120                 125
Arg Gly Arg Gly Ile Gln Leu Asn Asp Glu Ser Val Ser Ser Ser Leu
130                 135                 140
Gly Leu Arg Pro Asp Gly Thr Phe Gln Ile Gly Gly Ala Gly Arg Ser
145                 150                 155                 160
Ser Phe Thr Pro Arg Gln Ala Ile Leu Thr Leu Gln Thr Ser Ser Ser
                165                 170                 175
Glu Pro Arg Ser Gly Gly Ile Gly Thr Leu Gln Phe Ile Glu Glu Phe
            180                 185                 190
Val Pro Ser Val Tyr Phe Asn Pro Phe Ser Gly Pro Pro Gly His Tyr
        195                 200                 205
Pro Asp Gln Phe Ile Pro Asn Phe Asp Ala Val Lys Asp Ser Ala Asp
    210                 215                 220
Gly Tyr Asp
225

<210> SEQ ID NO 28
<211> LENGTH: 128
<212> TYPE: PRT
<213> ORGANISM: Human adenovirus type 5

<400> SEQUENCE: 28

Met Thr Asp Thr Leu Asp Leu Glu Met Asp Gly Ile Ile Thr Glu Gln
  1               5                  10                  15
Arg Leu Leu Glu Arg Arg Arg Ala Ala Ala Glu Gln Gln Arg Met Asn
             20                  25                  30
Gln Glu Leu Gln Asp Met Val Asn Leu His Gln Cys Lys Arg Gly Ile
         35                  40                  45
Phe Cys Leu Val Lys Gln Ala Lys Val Thr Tyr Asp Ser Asn Thr Thr
     50                  55                  60
Gly His Arg Leu Ser Tyr Lys Leu Pro Thr Lys Arg Gln Lys Leu Val
 65                  70                  75                  80
Val Met Val Gly Glu Lys Pro Ile Thr Ile Thr Gln His Ser Val Glu
                 85                  90                  95
Thr Glu Gly Cys Ile His Ser Pro Cys Gln Gly Pro Glu Asp Leu Cys
            100                 105                 110
Thr Leu Ile Lys Thr Leu Cys Gly Leu Lys Asp Leu Ile Pro Phe Asn
        115                 120                 125

<210> SEQ ID NO 29
<211> LENGTH: 582
<212> TYPE: PRT
<213> ORGANISM: Human adenovirus type 2

<400> SEQUENCE: 29

Met Lys Arg Ala Arg Pro Ser Glu Asp Thr Phe Asn Pro Val Tyr Pro
  1               5                  10                  15
Tyr Asp Thr Glu Thr Gly Pro Pro Thr Val Pro Phe Leu Thr Pro Pro
             20                  25                  30
Phe Val Ser Pro Asn Gly Phe Gln Glu Ser Pro Pro Gly Val Leu Ser
         35                  40                  45
Leu Arg Val Ser Glu Pro Leu Asp Thr Ser His Gly Met Leu Ala Leu
     50                  55                  60
Lys Met Gly Ser Gly Leu Thr Leu Asp Lys Ala Gly Asn Leu Thr Ser
```

```
              65                  70                  75                  80
Gln Asn Val Thr Thr Val Thr Gln Pro Leu Lys Thr Lys Ser Asn
                        85                  90                  95
Ile Ser Leu Asp Thr Ser Ala Pro Leu Thr Ile Thr Ser Gly Ala Leu
                100                 105                 110
Thr Val Ala Thr Thr Ala Pro Leu Ile Val Thr Ser Gly Ala Leu Ser
            115                 120                 125
Val Gln Ser Gln Ala Pro Leu Thr Val Gln Asp Ser Lys Leu Ser Ile
130                 135                 140
Ala Thr Lys Gly Pro Ile Thr Val Ser Asp Gly Lys Leu Ala Leu Gln
145                 150                 155                 160
Thr Ser Ala Pro Leu Ser Gly Ser Asp Ser Asp Thr Leu Thr Val Thr
                165                 170                 175
Ala Ser Pro Pro Leu Thr Thr Ala Thr Gly Ser Leu Gly Ile Asn Met
                180                 185                 190
Glu Asp Pro Ile Tyr Val Asn Asn Gly Lys Ile Gly Ile Lys Ile Ser
                195                 200                 205
Gly Pro Leu Gln Val Ala Gln Asn Ser Asp Thr Leu Thr Val Val Thr
        210                 215                 220
Gly Pro Gly Val Thr Val Glu Gln Asn Ser Leu Arg Thr Lys Val Ala
225                 230                 235                 240
Gly Ala Ile Gly Tyr Asp Ser Ser Asn Met Glu Ile Lys Thr Gly
                    245                 250                 255
Gly Gly Met Arg Ile Asn Asn Asn Leu Leu Ile Leu Asp Val Asp Tyr
                260                 265                 270
Pro Phe Asp Ala Gln Thr Lys Leu Arg Leu Lys Leu Gly Gln Gly Pro
                275                 280                 285
Leu Tyr Ile Asn Ala Ser His Asn Leu Asp Ile Asn Tyr Asn Arg Gly
            290                 295                 300
Leu Tyr Leu Phe Asn Ala Ser Asn Asn Thr Lys Lys Leu Glu Val Ser
305                 310                 315                 320
Ile Lys Lys Ser Ser Gly Leu Asn Phe Asp Asn Thr Ala Ile Ala Ile
                325                 330                 335
Asn Ala Gly Lys Gly Leu Glu Phe Asp Thr Asn Thr Ser Glu Ser Pro
                340                 345                 350
Asp Ile Asn Pro Ile Lys Thr Lys Ile Gly Ser Gly Ile Asp Tyr Asn
            355                 360                 365
Glu Asn Gly Ala Met Ile Thr Lys Leu Gly Ala Gly Leu Ser Phe Asp
        370                 375                 380
Asn Ser Gly Ala Ile Thr Ile Gly Asn Lys Asn Asp Asp Lys Leu Thr
385                 390                 395                 400
Leu Trp Thr Thr Pro Asp Pro Ser Pro Asn Cys Arg Ile His Ser Asp
                    405                 410                 415
Asn Asp Cys Lys Phe Thr Leu Val Leu Thr Lys Cys Gly Ser Gln Val
            420                 425                 430
Leu Ala Thr Val Ala Ala Leu Ala Val Ser Gly Asp Leu Ser Ser Met
            435                 440                 445
Thr Gly Thr Val Ala Ser Val Ser Ile Phe Leu Arg Phe Asp Gln Asn
        450                 455                 460
Gly Val Leu Met Glu Asn Ser Ser Leu Lys Lys His Tyr Trp Asn Phe
465                 470                 475                 480
Arg Asn Gly Asn Ser Thr Asn Ala Asn Pro Tyr Thr Asn Ala Val Gly
                    485                 490                 495
```

-continued

```
Phe Met Pro Asn Leu Leu Ala Tyr Pro Lys Thr Gln Ser Gln Thr Ala
            500                 505                 510

Lys Asn Asn Ile Val Ser Gln Val Tyr Leu His Gly Asp Lys Thr Lys
            515                 520                 525

Pro Met Ile Leu Thr Ile Thr Leu Asn Gly Thr Ser Glu Ser Thr Glu
            530                 535                 540

Thr Ser Glu Val Ser Thr Tyr Ser Met Ser Phe Thr Trp Ser Trp Glu
545                 550                 555                 560

Ser Gly Lys Tyr Thr Thr Glu Thr Phe Ala Thr Asn Ser Tyr Thr Phe
                565                 570                 575

Ser Tyr Ile Ala Gln Glu
            580

<210> SEQ ID NO 30
<211> LENGTH: 21
<212> TYPE: PRT
<213> ORGANISM: Artificial
<220> FEATURE:
<221> NAME/KEY: Modified-sites
<222> LOCATION: 2, 3, 5-17, 19-20
<223> OTHER INFORMATION: Xaa can be any amino acid; consensus
      metal-binding sequence

<400> SEQUENCE: 30

Cys Xaa Xaa Cys Xaa Xaa Xaa Xaa Xaa Xaa Xaa Xaa Xaa Xaa Xaa Xaa
1               5                   10                  15

Xaa Cys Xaa Xaa Cys
            20

<210> SEQ ID NO 31
<211> LENGTH: 7
<212> TYPE: PRT
<213> ORGANISM: Bovine adenovirus type 3; human adenovirus type 5
<220> FEATURE:
<221> NAME/KEY: Modified-site
<222> LOCATION: (4)
<223> OTHER INFORMATION: Xaa can be any amino acid; region of homology

<400> SEQUENCE: 31

Gln Ser Ser Xaa Ser Thr Ser
1               5

<210> SEQ ID NO 32
<211> LENGTH: 27
<212> TYPE: PRT
<213> ORGANISM: Bovine adenovirus type 3

<400> SEQUENCE: 32

Pro Leu Leu Phe Ala Phe Val Leu Cys Thr Gly Cys Ala Val Leu Leu
1               5                   10                  15

Thr Ala Phe Gly Pro Ser Ile Leu Ser Gly Thr
            20                  25

<210> SEQ ID NO 33
<211> LENGTH: 57
<212> TYPE: PRT
<213> ORGANISM: Bovine adenovirus type 3

<400> SEQUENCE: 33

Glu Glu Val Thr Ser His Phe Phe Leu Asp Cys Pro Glu Asp Pro Ser
1               5                   10                  15

Arg Glu Cys Ser Ser Cys Gly Phe His Gln Ala Gln Ser Gly Ile Pro
            20                  25                  30
```

```
Gly Ile Met Cys Ser Leu Cys Tyr Met Arg Gln Thr Tyr His Cys Ile
            35                  40                  45

Tyr Ser Pro Val Ser Glu Glu Met
    50              55

<210> SEQ ID NO 34
<211> LENGTH: 12
<212> TYPE: PRT
<213> ORGANISM: Bovine adenovirus type 3

<400> SEQUENCE: 34

Val Asp Leu Glu Cys His Glu Val Leu Pro Pro Ser
1               5                   10
```

RECOMBINANT BOVINE ADENOVIRUSES

This application is a division of application Ser. No. 08/164,292, filed Dec. 9, 1993, now U.S. Pat. No. 5,820,868.

TECHNICAL FIELD

The present invention relates novel bovine adenovirus (BAV) expression vector systems in which one or both of the early region 1 (E1) and the early region 3 (E3) gene deletions are replaced by a foreign gene and novel recombinant mammalian cell lines stably transformed with BAV E1 sequences, and therefore, expresses E1 gene products, to allow a bovine adenovirus with an E1 gene deletion replaced by a foreign gene to replicate therein. These materials are used in production of recombinant BAV expressing heterologous (antigenic) polypeptides or fragments for the purpose of live recombinant virus or subunit vaccines or for other therapies.

BACKGROUND OF THE INVENTION

The adenoviruses cause enteric or respiratory infection in humans as well as in domestic and laboratory animals.

The bovine adenoviruses (BAVs) comprise at least nine serotypes divided into two subgroups. These subgroups have been characterized based on enzyme-linked immunoassays (ELISA), serologic studies with immunofluorescence assays, virus-neutralization tests, immunoelectron microscopy, by their host specificity and clinical syndromes. Subgroup 1 viruses include BAV 1, 2, 3 and 9 and grow relatively well in established bovine cells compared to subgroup 2 which includes BAV 4, 5, 6, 7 and 8.

BAV3 was first isolated in 1965 and is the best characterized of the BAV genotypes and contains a genome of approximately 35 kb (Kurokawa et al (1978) *J. Virol.* 28:212–218). The locations of hexon (Hu et al (1984) *J. Viol.* 49:604–608) and proteinase (Cai et al., (1990) *Nuc. Acids Res.*, 18:5568), genes in the BAV3 genome have been identified and sequenced. However, the location and sequences of other genes such as early region 1 (E1) and 3 (E3) in the BAV genome have not been reported.

In the human adenovirus (HAd) genome there are two important regions: E1 and E3 in which foreign genes can be inserted to generate recombinant adenoviruses (Berkner and Sharp (1984) *Nuc. Acid Res.*, 12:1925–1941 and Haj-Ahmad and Graham (1986) *J. Virol.*, 57:267–274). E1 proteins are essential for virus replication in tissue culture, however, conditional-helper adenovirus recombinants containing foreign DNA in the E1 region, can be generated in a cell line which constitutively expresses E1 (Graham et al., (1977) *J. Gen. Virol.*, 36:59–72). In contrast, E3 gene products of HAd 2 and HAd 5 are not required for in vitro or in vivo infectious virion production, but have an important role in host immune responses to virus infection (Andersson et al (1985) *Cell* 43:215–222; Burgert et al (1987) *EMBO J.* 6:2019–2026; Carlin et al (1989) Cell 57:135–144; Ginsberg et al (1989) *PNAS, USA* 86:3823–3827; Gooding et al (1988) *Cell* 53:341–346; Tollefson et al (1991) *J. Virol.* 65:3095–3105; Wold and Gooding (1989) *Mol. Biol. Med.* 6:433–452 and Wold and Gooding (1991) *Virolology* 184:1–8). The E3–19 kiloDalton (kDa) glycoprotein (gp19) of human adenovirus type 2 (HAd2) binds to the heavy chain of a number of class 1 major histocompatibility complex (MHC) antigens in the endoplasmic reticulum thus inhibiting their transport to the plasma membrane (Andersson et al. (1985) *Cell* 43:215–222; Burgert and Kvist, (1985) *Cell* 41:987–997; Burgert and Kvist, (1987) *EMBO J.* 6:2019–2026). The E3–14.7 kDa protein of HAd2 or HAd5 prevents lysis of virus-infected mouse cells by tumor necrosis factor (TNF) (Gooding et al. (1988) *Cell* 53:341–346). In addition, the E3–10.4 kDa and E3–14.5 kDa proteins form a complex to induce endosomal-mediated internalization and degradation of the epidermal growth factor receptor (EGF-R) in virus-infected cells (Carlin et al. *Cell* 57:135–144; Tollefson et al. (1991) *J. Virol.* 65:3095–3105). The helper-independent recombinant adenoviruses having foreign genes in the E3 region replicate and express very well in every permissive cell line (Chanda et al (1990) *Virology* 175:535–547; Dewar et al (1989) *J. Virol.* 63:129–136; Johnson et al (1988) *Virology* 164:1–14; Lubeck et al (1989) *PNAS, USA* 86:6763–6767; McDermott et al (1989) *Virology* 169:244–247; Mittal et al (1993) *Virus Res.* 28:67–90; Morin et al (1987) *PNAS, USA* 84:4626–4630; Prevec et al (1990) *J. Inf. Dis.* 161:27–30; Prevec et al (1989) *J. Gen. Virol.* 70:429–434; Schneider et al (1989) *J. Gen. Virol.* 70:417–427 and Yuasa et al (1991) *J. Gen. Virol.* 72:1927–1934). Based on the above studies and the suggestion that adenoviruses can package approximately 105% of the wild-type (wt) adenovirus genome (Bett et al (1993) *J. Virol.* 67:5911–5921 and Ghosh-Choudhury et al (1987) *EMBO. J.* 6:1733–1739), an insertion of up to 1.8 kb foreign DNA can be packaged into adenovirus particles for use as an expression vector for foreign proteins without any compensating deletion.

It is assumed that an indigenous adenovirus vector would be better suited for use as a live recombinant virus vaccine in different animal species compared to an adenovirus of human origin. Non-human adenovirus-based expression vectors have not been reported so far. If like HAds E3, the E3 regions in other adenoviruses are not essential for virus replication in cultured cells, adenovirus recombinants containing foreign gene inserts in the E3 region could be generated.

BAV3 is a common pathogen of cattle usually resulting in subclinical infection though occasionally associated with a more serious respiratory tract infection (Darbyshire et al., 1966 *Res. Vet Sci* 7:81–93; Mattson et al., 1988 *J. Vet Res* 49:67–69). BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465–473; Motoi et al., 1972 *Gann* 63:415–418; M. Hitt, personal communication). Cross hybridization was observed between BAV3 and human adenovirus type 2 (HAd2) (Hu et al., 1984 *J. Virol.* 49:604–608) in most regions of the genome including some regions near but not at the left end of the genome.

The E1A gene products of the group C human adenoviruses have been very extensively studied and shown to mediate transactivation of both viral and cellular genes (Berk et al., 1979 *Cell* 17:935–944; Jones and Shenk, 1979 *Cell* 16:683–689; Nevins, 1981 *Cell* 26:213–220; Nevins, 1982 *Cell* 29:913–919; reviewed in Berk, 1986 *Ann. Res. Genet* 20:45–79), to effect transformation of cells in culture (reviewed in Graham, F. L. (1984) "Transformation by and oncogenicity of human adenoviruses. In:The Adenoviruses." H. S. Ginsberg, Editor. Plenum Press, New York; Branton et al., 1985 *Biochim. Biophys. Acta* 780:67–94) and induce cell DNA synthesis and mitosis (Zerler et al., 1987 *Mol. Cell Biol.* 7:821–929; Bellet et al., 1989 *J. Virol.* 63:303–310; Howe et al., 1990 *PNAS, USA* 87:5883–5887; Howe and Bayley, 1992 *Virology* 186:15–24). The E1A transcription unit comprises two coding sequences separated by an intron region which is deleted from all processed E1A transcripts.

In the two largest mRNA species produced from the E1A transcription unit, the first coding regions is further subdivided into exon 1, a sequence found in both the 12s and 13s mRNA species, and the unique region, which is found only in the 13s mRNA species. By comparisons between E1A proteins of human and simian adenoviruses three regions of somewhat conserved protein sequence (CR) have been defined (Kimelman et al., 1985 *J. Virol.* 53:399–409). CR1 and CR2 are encoded in exon 1, while CR3 is encoded in the unique sequence and a small portion of exon 2. Binding sites for a number of cellular proteins including the retinoblastoma protein Rb, cyclin A and an associated protein kinase $p33^{cdk2}$, and other, as yet unassigned, proteins have been defined in exon 1 encoded regions of E1A proteins (Yee and Branton, 1985 *Virology* 147:142–153; Harlow et al., 1986 *Mol. Cell Biol.* 6:1579–1589; Barbeau et al., 1992 *Biochem. Cell Biol.* 70:1123–1134). Interaction of E1A with these cellular proteins has been implicated as the mechanism through which E1A participates in immortalization and oncogenic transformation (Egan et al, 1989 *Oncogene* 4:383–388; Whyte et al., 1988 *Nature* 334:124–129; Whyte et al, 1988 *J. Virol.* 62:257–265). While E1A alone may transform or immortalize cells in culture, the coexpression of both E1A and either the E1B-19k protein or the E1B-55k protein separately or together is usually required for high frequency transformation of rodent cells in culture (reviewed in Graham, 1984 supra; Branton et al., 1985 supra; McLorie et al., 1991 *J. Gen Virol.* 72:1467–1471).

Transactivation of other viral early genes in permissive infection of human cells is principally mediated by the amino acid sequence encoded in the CR3 region of E1A (Lillie et al., 1986 *Cell* 46:1043–1051). Conserved cysteine residues in a $CysX_2CysX_{13}CysX_2Cys$ sequence motif (SEQ ID NO:30) in the unique region are associated with metal ion binding activity (Berg, 1986 supra) and are essential for transactivation activity (Jelsma et al., 1988 *Virology* 163:494–502; Culp et al., 1988 *PNAS, USA* 85:6450–6454). As well, the amino acids in CR3 which are immediately amino (N)-terminal to the metal binding domain have been shown to be important in transcription activation, while those immediately carboxy (C)-terminal to the metal binding domain are important in forming associations with the promoter region (Lillie and Green, 1989 *Nature* 338:39–44; see FIG. 3).

The application of genetic engineering has resulted in several attempts to prepare adenovirus expression systems for obtaining vaccines. Examples of such research include the disclosures in U.S. Pat. No. 4,510,245 on an adenovirus major late promoter for expression in a yeast host; U.S. Pat. No. 4,920,209 on a live recombinant adenovirus type 7 with a gene coding for hepatitis-B surface antigen located at a deleted early region 3; European patent 389 286 on a non-defective human adenovirus 5 recombinant expression system in human cells for HCMV major envelope glycoprotein; WO 91/11525 on live non-pathogenic immunogenic viable canine adenovirus in a cell expressing E1a proteins; French patent 2 642 767 on vectors containing a leader and/or promoter from the E3 of adenovirus 2.

The selection of a suitable virus to act as a vector for foreign gene expression, and the identification of a suitable non-essential region as a site for insertion of the gene pose a challenge. In particular, the insertion site must be non-essential for the viable replication of the virus and its effective operation in tissue culture and also in vivo. Moreover, the insertion site must be capable of accepting new genetic material, whilst ensuring that the virus continues to replicate. An essential region of a virus genome can also be utilized for foreign gene insertion if the recombinant virus is grown in a cell line which complements the function of that particular essential region in trans.

The present inventors have now identified suitable regions in the BAV genome and have succeeded in inserting foreign genes to generate BAV recombinants.

DISCLOSURE OF THE INVENTION

The present invention relates to novel bovine adenovirus expression vector systems in which part or all of one or both of the E1 and E3 gene regions are deleted and to recombinant mammalian cell lines of bovine origin transformed with the BAV E1 sequences, and thus, constitutively express the E1 gene products to allow bovine adenovirus, having a deletion of part or all of the E1 gene region replaced by a heterologous nucleotide sequence encoding a foreign gene or fragment thereof, to replicate therein and use of these materials in production of heterologous (antigenic) polypeptides or fragments thereof.

The invention also related to a method of preparing a live recombinant virus or subunit vaccines for producing antibodies or cell mediated immunity to an infectious organism in a mammal, such as bovine, which comprises inserting into the bovine adenovirus genome the gene or fragment coding for the antigen which corresponds to said antibodies or induces said cell mediated immunity, together with or without an effective promoter therefore, to produce BAV recombinants.

Generally, the foreign gene construct is cloned into a nucleotide sequence which represents only a part of the entire viral genome having one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Multiple copies of a coding sequence or more than one coding sequences can be inserted so that the recombinant vector can express more than one foreign protein. The foreign gene can have additions, deletions or substitutions to enhance expression and/or immunological effects of the expressed protein.

The invention also includes an expression system comprising an bovine adenovirus expression vector wherein heterologous nucleotide sequences with or without any exogenous regulatory elements, replace the E1 gene region and/or part or all of the E3 gene region.

The invention also includes (A) a recombinant vector system comprising the entire BAV DNA and a plasmid or two plasmids capable of generating a recombinant virus by in vivo recombination following cotransfection of a suitable cell line comprising BAV DNA representing the entire wild-type BAV genome and a plasmid comprising a bovine adenovirus left or right end sequences containing the E1 or E3 gene regions, respectively, with a heterologous nucleotide sequence encoding a foreign gene or fragment thereof substituted for part or all of the E1 or E3 gene regions; (B) a live recombinant bovine adenovirus vector (BAV) system selected from the group consisting of: (a) a system wherein part or all of the E1 gene region is replaced by a heterologous nucleotide sequence encoding a foreign gene or fragment thereof; (b) a system wherein a part or all of the E3 gene region is replaced by a heterologous nucleotide sequence encoding a foreign gene or fragment thereof; and (c) a system wherein part or all of the E1 gene region and part or all of the E3 gene region are deleted and a heterologous nucleotide sequence encoding a foreign gene or fragment thereof is inserted into at least one of the deletions; (C) a recombinant bovine adenovirus (BAV) comprising a deletion of part or all of E1 gene region, a deletion of part or all of E3 gene region or deletion of both, and inserted into at least one deletion a heterologous nucleotide sequence coding for an antigenic determinant of a disease causing organism; (D) a recombinant bovine adenovirus expression system comprising a deletion of part or all of E1, a deletion of part or all of E3, or both deletions, and inserted into at least one deletion a heterologous nucleotide sequence coding for a foreign gene or fragment thereof under control of an expression promoter: or (E) a recombinant bovine adenovirus (BAV) for producing an immune response in a mammalian host comprising: (1) BAV recombinant containing a heterologous nucleotide sequence coding for an antigenic determinant needed to obtain the desired immune response in association with or without (2) an effective promoter to provide expression of said antigenic determinant in immunogenic quantities for use as a live recombinant virus or recombinant protein or subunit vaccine; (F) a mutant bovine adenovirus (BAV) comprising a deletion of part or all of E1 and/or a deletion of part or all of E3.

Recombinant mammalian cell lines stably transformed with BAV E1 gene region sequences, said recombinant cell lines thereby capable of allowing replication therein of a bovine adenovirus comprising a deletion of part or all of the E1 or E3 gene regions replaced by a heterologous or homologous nucleotide sequence encoding a foreign gene or fragment thereof. The invention also includes production, isolation and purification of polypeptides or fragments thereof, such as growth factors, receptors and other cellular proteins from recombinant bovine cell lines expressing BAV E1 gene products.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in a target organ or tissue.

Another aspect of the invention provides a virus vaccine composition which comprises the recombinant virus or recombinant protein in association with or without a pharmaceutically acceptable carrier. The recombinant virus vaccine can be formulated for administration by an oral dosage (e.g. as an enteric coated tablet), by injection or otherwise. More specifically, these include a vaccine for protecting a mammalian host against infection comprising a live recombinant adenovirus or recombinant protein produced by the recombinant adenovirus of the invention wherein the foreign gene or fragment encodes an antigen and formulated with or without a pharmaceutically acceptable carrier.

The invention also includes methods of producing antibodies or cell mediated immunity in a mammal including (1) a method for eliciting an immune response in a mammalian host against an infection comprising: administering a vaccine comprising a live BAV recombinant of the invention wherein the foreign gene or fragment encodes an antigen with or without a pharmaceutically acceptable carrier, and (2) a method for eliciting an immune response in a mammalian host against an infection comprising: administering a vaccine comprising a recombinant antigen prepared by culturing a BAV recombinant wherein the foreign gene or fragment encodes the desired antigen with or without a pharmaceutically acceptable carrier.

The following disclosure will render these and other embodiments of the present invention readily apparent to those of skill in the art. While the disclosure often refers to bovine adenovirus type 3 (BAV3), it should be understood that this is for the purpose of illustration and that the same features apply to bovine adenovirus of the other type, 1, 2, 4, 5, 6, 7 8, and 9 and the invention described and claimed herein is intended to cover all of these bovine adenovirus types.

BRIEF DESCRIPTION OF THE DRAWINGS

FIGS. 1A–1L. Sequence and major open reading frames of the left 11% of the BAV3 genome (SEQ ID NO: 1 through SEQ ID NO: 8). The region comprises the E1 and protein IX transcription region. The 195 nucleotide inverted terminal repeat sequence identified by Shinagawa et al., 1987 *Gene* 55:85–93 is shown in italics. The amino acid sequence for the largest E1A protein, two E1B proteins and protein IX are presented. The probable splice donor ([), splice acceptor (]) and intron sequence (underlined italics) within the E1A region are marked. A 35 base pair repeat sequence between E1A and E1B is indicated in bold underline. Possible transcription promoter TATA sequences and possible poly A addition sequences AATAA are also indicated.

FIGS. 2A–2B. Regions of homology in the E1A proteins of BAV3 and human adenovirus type 5 (HAd5). The amino acid residue of each serotype is indicated. A. Conserved region 3 (CR3) of HAd5 (SEQ ID NO:9) subdivided into three functional regions as defined by Lillie et al (1989) *Nature* 338:39–44 and described in the Background of the Invention. The intron sequence of BAV3 E1A occurs within the serine amino acid codon at position 204 (nucleotide positions 1216–1322 of SEQ ID NO: 1). B. A portion of conserved region 2 (CR2) of HAd5 (SEQ ID NO: 10), showing the residues thought to be important in the binding of retinoblastoma protein Rb (Dyson et al., 1990 *J. Virol.* 64:1353–1356), and the comparable sequence from BAV3 (SEQ ID NO: 34).

FIGS. 3A–3B. Homology regions between the HAd5 and E1B 19 k (176R) protein (SEQ ID NO: 11 through SEQ ID NO: 12) and the corresponding BAV3 (157R) protein (amino acid positions 83–99 and 136–142 of SEQ ID NO: 4. The amino acid residue number for each of the viruses is indicated.

FIGS. 4A–4C. The C-terminal 346R of HAd5 E1B 56k (496R) (SEQ ID NO: 13) and the corresponding BAV3 protein (420R) (amino acid positions 74–420 of (SEQ ID NO: 6). The HAd5 protein comparison begins at residue 150 and the BAV3 (in italics) at residue 74. The amino terminal regions of these proteins which are not presented show no significant homology.

FIG. 5. Homology comparison of the amino acid sequence of HAd5 protein IX (SEQ ID NO: 14) and the corresponding protein of BAV3 (SEQ ID NO: 8) (in italics).

FIGS. 7A–7R. Nucleotide sequence of BAV3 between 77 and 92 m.u. (SEQ ID NO: 15 through SEQ ID NO: 26) showing ORFs that have the potential to encode polypeptides of at least 50 amino acids after the initiating methionine. The nucleotide sequence was analyzed using the program DISPCOD (PC/GENE). Potential N-glycosylation sites (N-X-T/S) and polyadenylation signals are underlined and the first methionine of each ORF is shown in bold.

FIGS. 8(a), 8(b), 8(c)-1, 8(c)-2, and 8(c)-3. Comparison between the predicted amino acid sequences for the ORFs of BAV3 and known proteins of HAd2 or –5 using the computer program PALIGN (PC/GENE), with comparison matrix structural-genetic matrix; open gap cost 6; unit gap cost 2. Identical residues are indicated by a colon and similar residues by a dot. (a) Comparison between the predicted amino acid sequence encoded by the 3' end of BAV3 ORF 1 (SEQ ID NO: 16) and the HAd2 hexon-associated pVIII precursor (SEQ ID NO: 27). (b) Comparison between the ORF 4 (amino acid positions 34–154 of SEQ ID NO: 22) and the HAd5 14.7K E3 protein (SEQ ID NO: 28). (c) Comparison between the predicted amino acid sequence encoded by BAV3 ORF 6 (amino acid positions 8–893 of SEQ ID NO: 26) and the HAd2 fibre protein (SEQ ID NO: 29).

B: BamHI, E: EcoRI, Xb: XbaI, 3.1: BAV3-Luc (3.1), 3.2: BAV3-Luc (3.2) and wt: wild-type BAV3.

Figure 12:
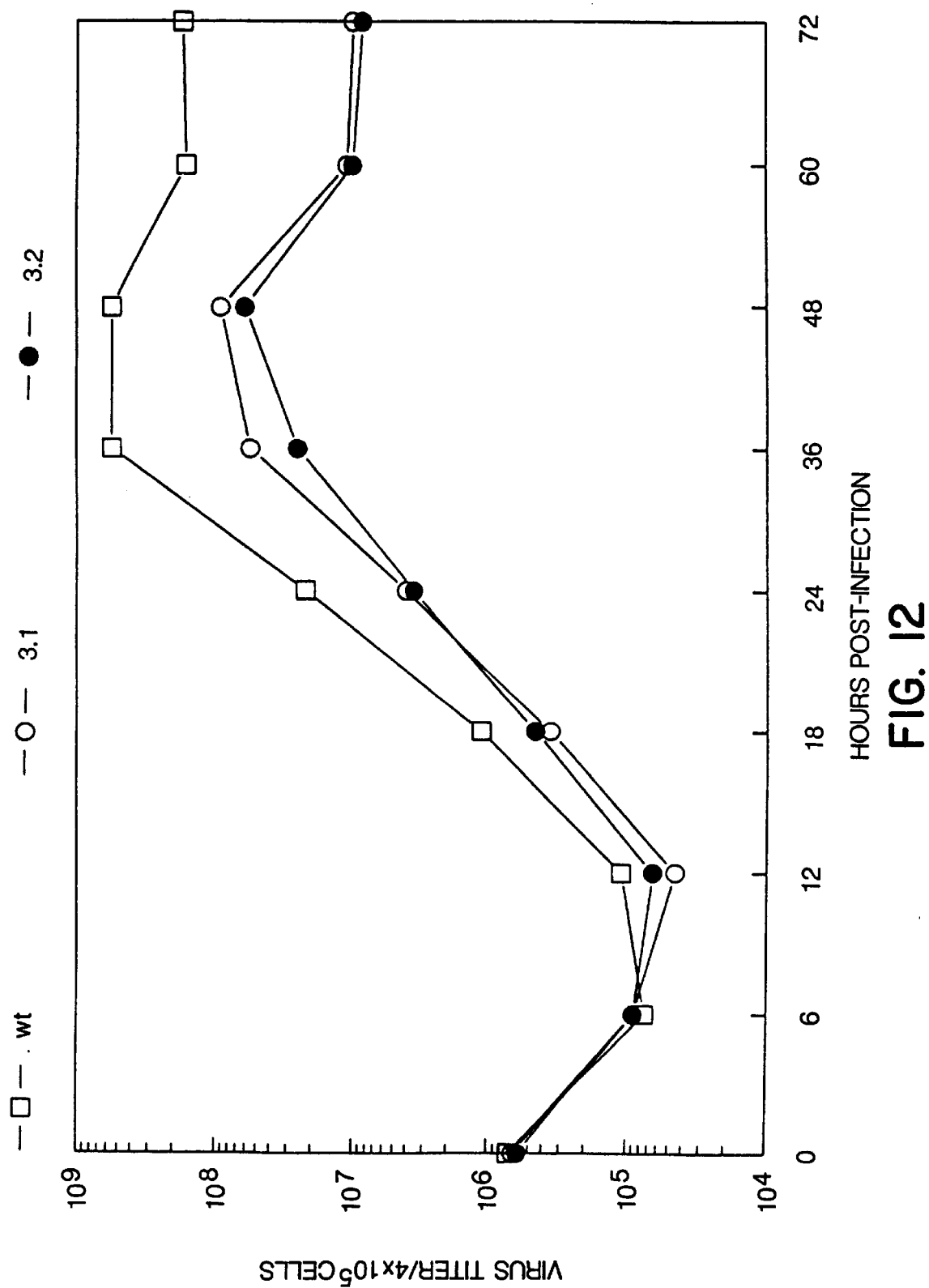

FIG. 12. Single step growth curve for wt BAV3 and BAV3-Luc. Confluent monolayers of MDBK cells in 25 mm multi-well culture plates were inoculated with the wt BAV3, BAV3-Luc (3.1) or BAV3-Luc (3.2) at a m.o.i. of 10 p.f.u. per cell. The virus was allowed to adsorb for 1 h at 37° C., cell monolayers were washed 3 times with PBS$^{++}$ (0.137 M NaCl, 2.7 mM KCl, 8 mM Na$_2$HPO$_4$, 1.5 mM KH$_2$PO$_4$, containing 0.01% CaCl$_2$.2H$_2$O & 0.01% MgCl$_2$.6H$_2$O) and incubated at 37° C. in 1 ml maintenance medium containing 2% horse serum. At various times post-infection, cells were harvested along with the supernatant, frozen and thawed three times and titrated on MDBK cells by plaque assay. Results are the means of duplicate samples.

Figure 13:
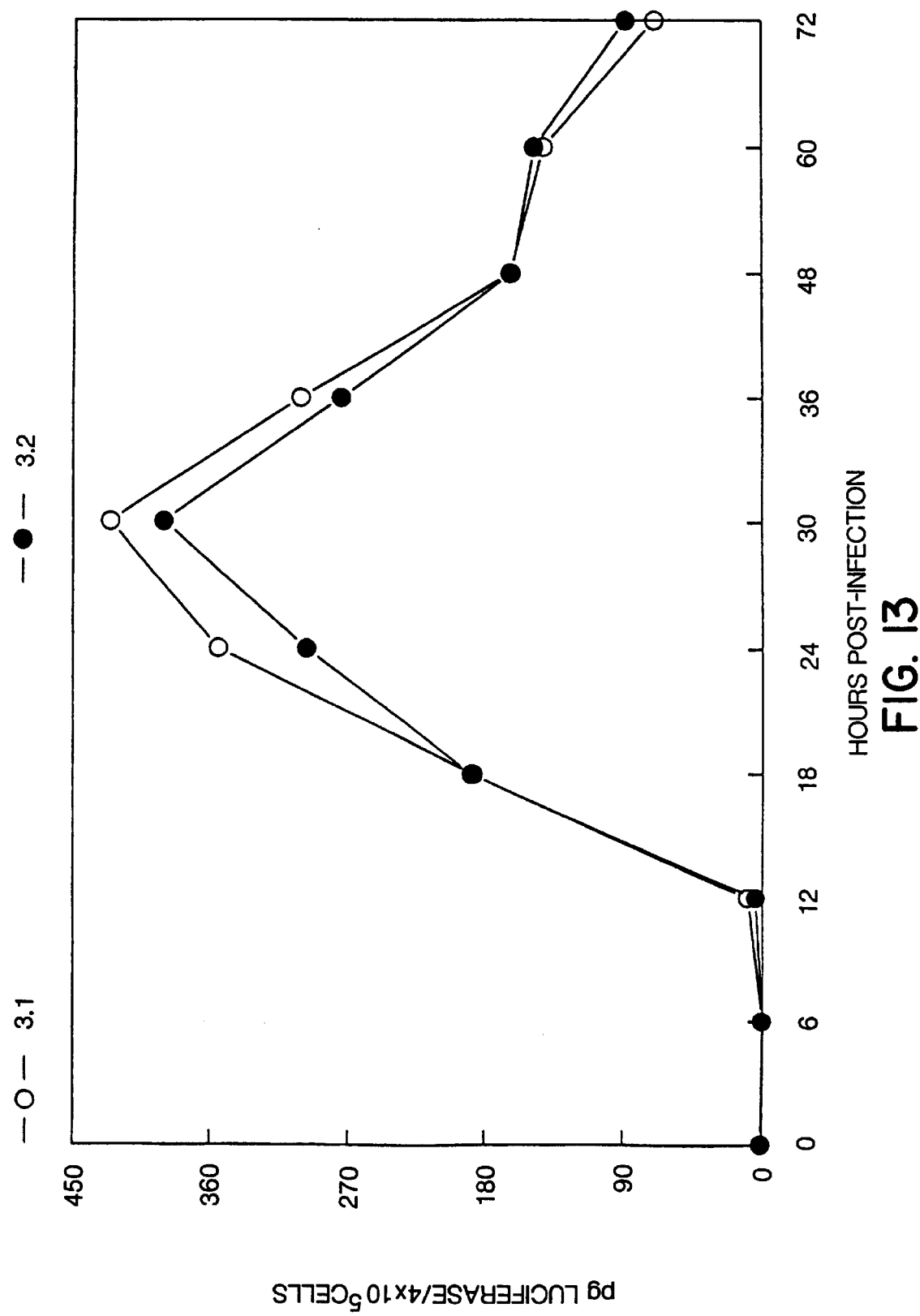

FIG. 13. Kinetics of luciferase expression in MDBK cells-infected with BAV3-Luc. Confluent MDBK cell monolayers in 25 mm multi-well culture plates were infected with BAV3-Luc (3.1) or BAV3-Luc (3.2) at a m.o.i. of 50 p.f.u. per cell. At indicated time points post-infection, virus-infected cells were harvested and assayed in duplicate for luciferase activity.

Figure 14A:
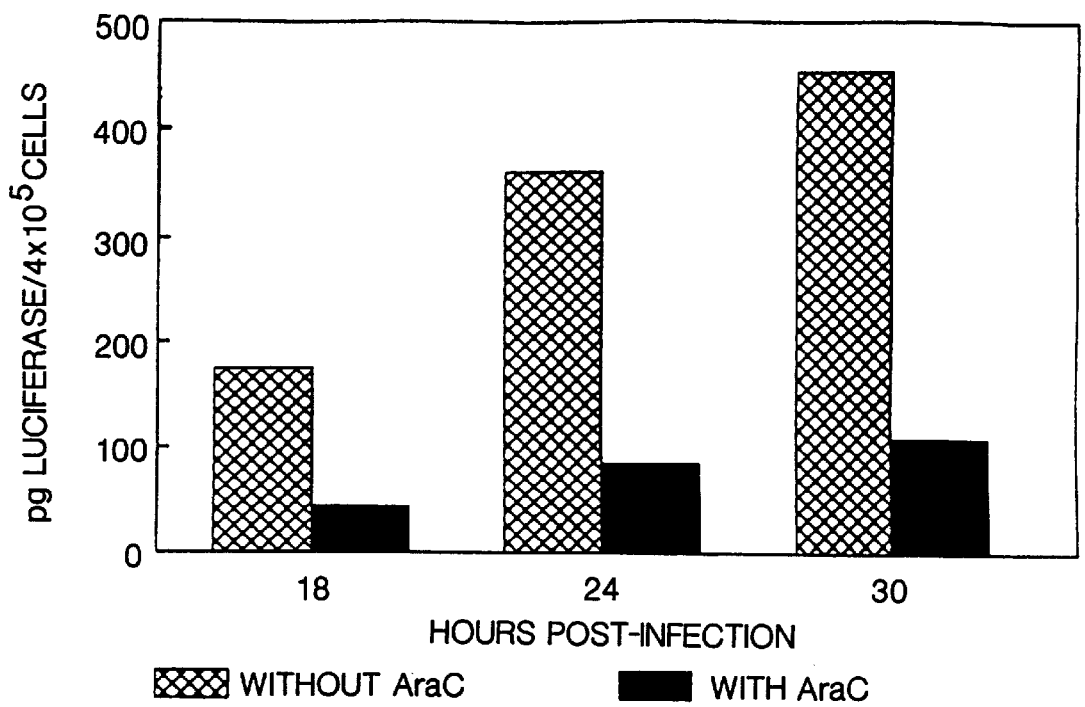
Figure 14B:
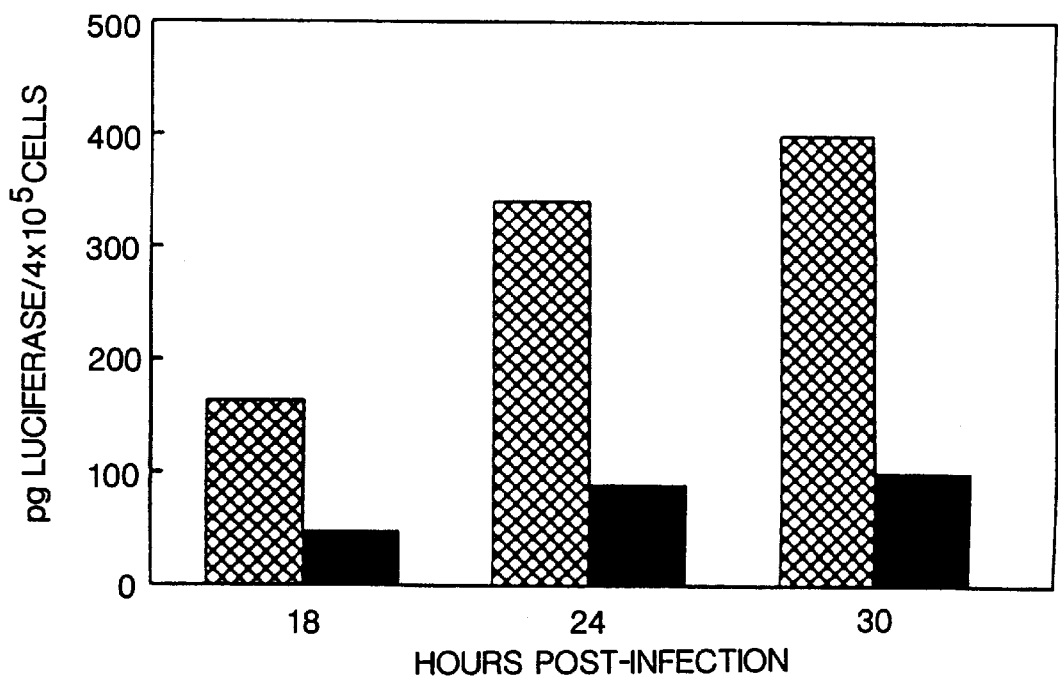

FIGS. 14A–14B. Luciferase expression in the presence of 1-β-D-arabinofluranosyl cytosine (AraC) in MDBK cells-infected with BAV3-Luc. Confluent MDBK cell monolayers in 25 mm multi-well culture plates were infected with A) BAV3-Luc (3.1) or B) BAV3-Luc (3.2) at a m.o.i. of 50 p.f.u. per cell and incubated in the absence or presence of 50 μg AraC per ml of maintenance medium. At indicated time points post-infection, virus-infected cells were harvested and assayed in duplicate for luciferase activity.

Figure 15A:
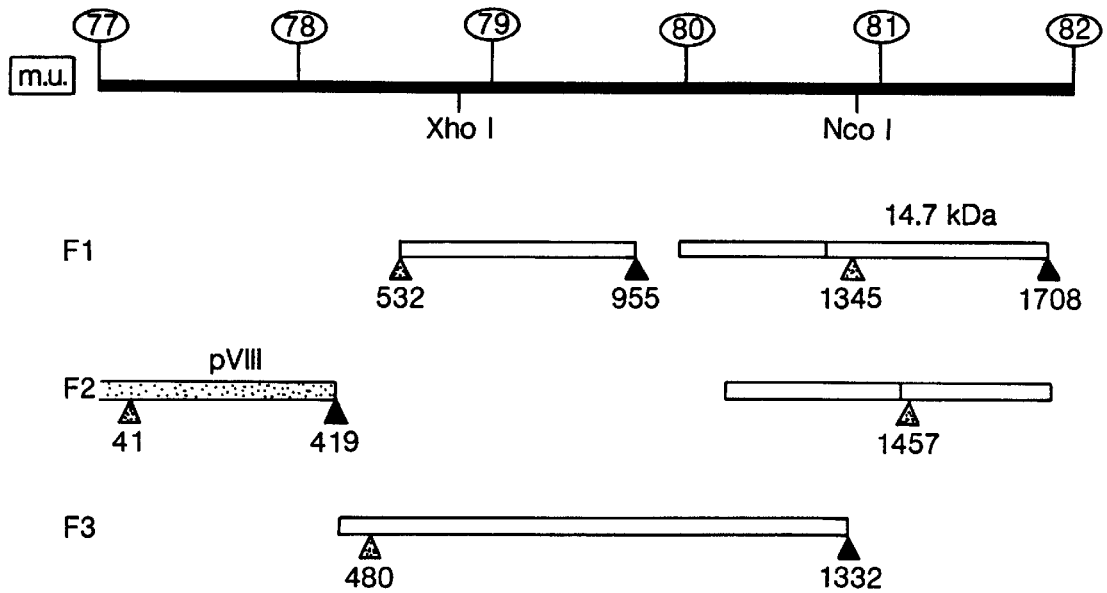
Figure 15B:
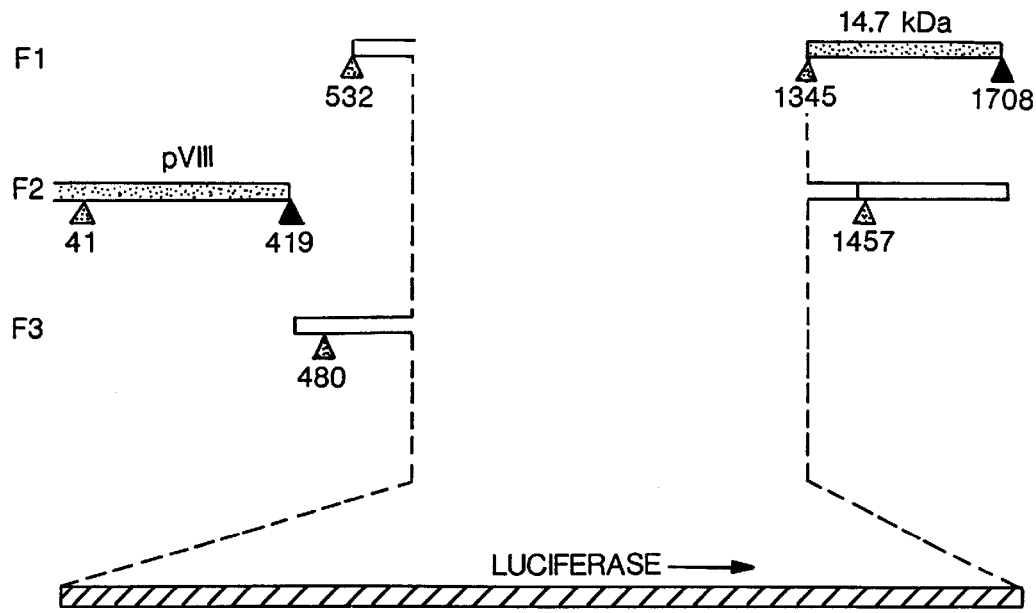

FIGS. 15A–15B. Transcription maps of the wt BAV3 and BAV3-Luc genomes in the E3 region. The genome of wt BAV3 between m.u. 77 and 82 is shown which represents the E3 region. The location of XhoI and NcoI sites which were used to make an E3 deletion are shown. (a) The three frames (F1, F2 and F3) representing the open reading frames (ORFs) in the upper strand of the wt BAV3 genome in the E3 region are represented by bars. The shaded portions indicate regions of similarities to pVIII and E3–14.7 kDa proteins of HAd5. The positions of the initiation and termination codons for ORFs likely to code for viral proteins are shown by open and closed triangles, respectively. (b) The predicted ORFs for the upper strand in E3 of the BAV3-Luc genome are shown after a 696 bp XhoI-NcoI E3 deletion replaced by the luciferase gene. The ORFs for pVIII and E3–14.7 kDa proteins are intact. The transcription map of the wt BAV3 E3 was adapted from the DNA sequence submitted to the GenBank database under accession number D16839.

Figure 16:
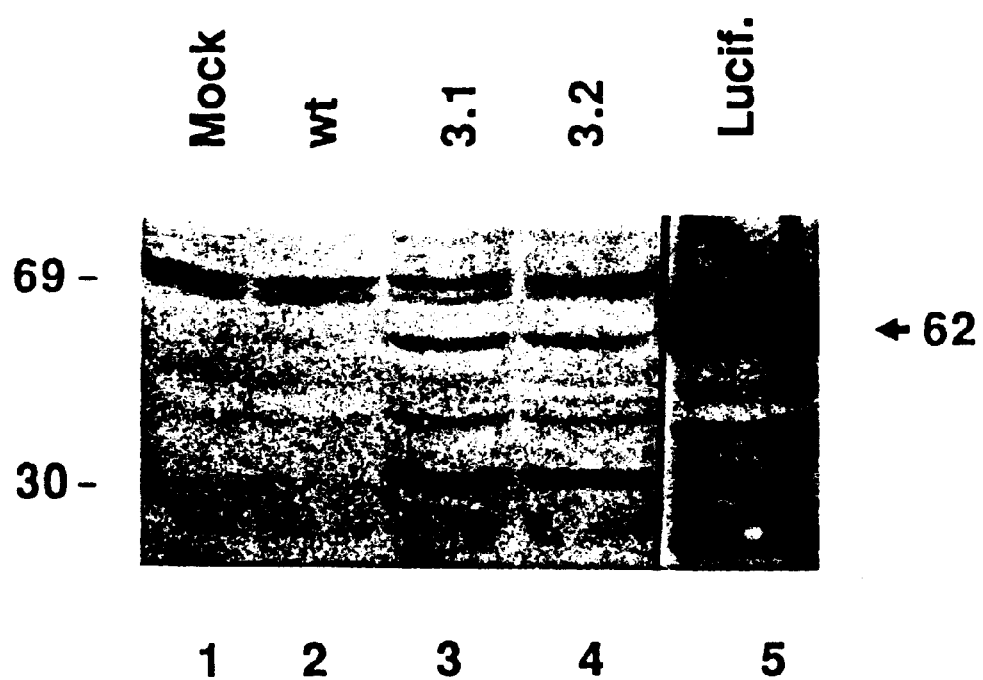

FIG. 16. Western blot analysis of virus-infected MDBK cells using an anti-luciferase antibody. Confluent monolayers of MDBK cells were mock-infected (lane 1) or infected with the wt BAV3 (lane 2), BAV3-Luc (3.1) (lane 3) and BAV3-Luc (3.2) (lane 4) at a m.o.i. of 50 p.f.u. per cell, harvested at 18 h post-infection, cell extracts prepared and analyzed by SDS-PAGE and Western blotting using a rabbit anti-luciferase antibody. Purified firefly luciferase was used as a positive control (lane 5). The lane 5 was excised to obtain a shorter exposure. The protein molecular weight markers in kDa are shown on the left. The arrow indicates the 62 kDa luciferase bands reacted with the anti-luciferase antibody.

wt: wild-type BAV3, 3.1: BAV3-Luc (3.1) and 3.2: BAV3-Luc (3.2).

Figure 17:
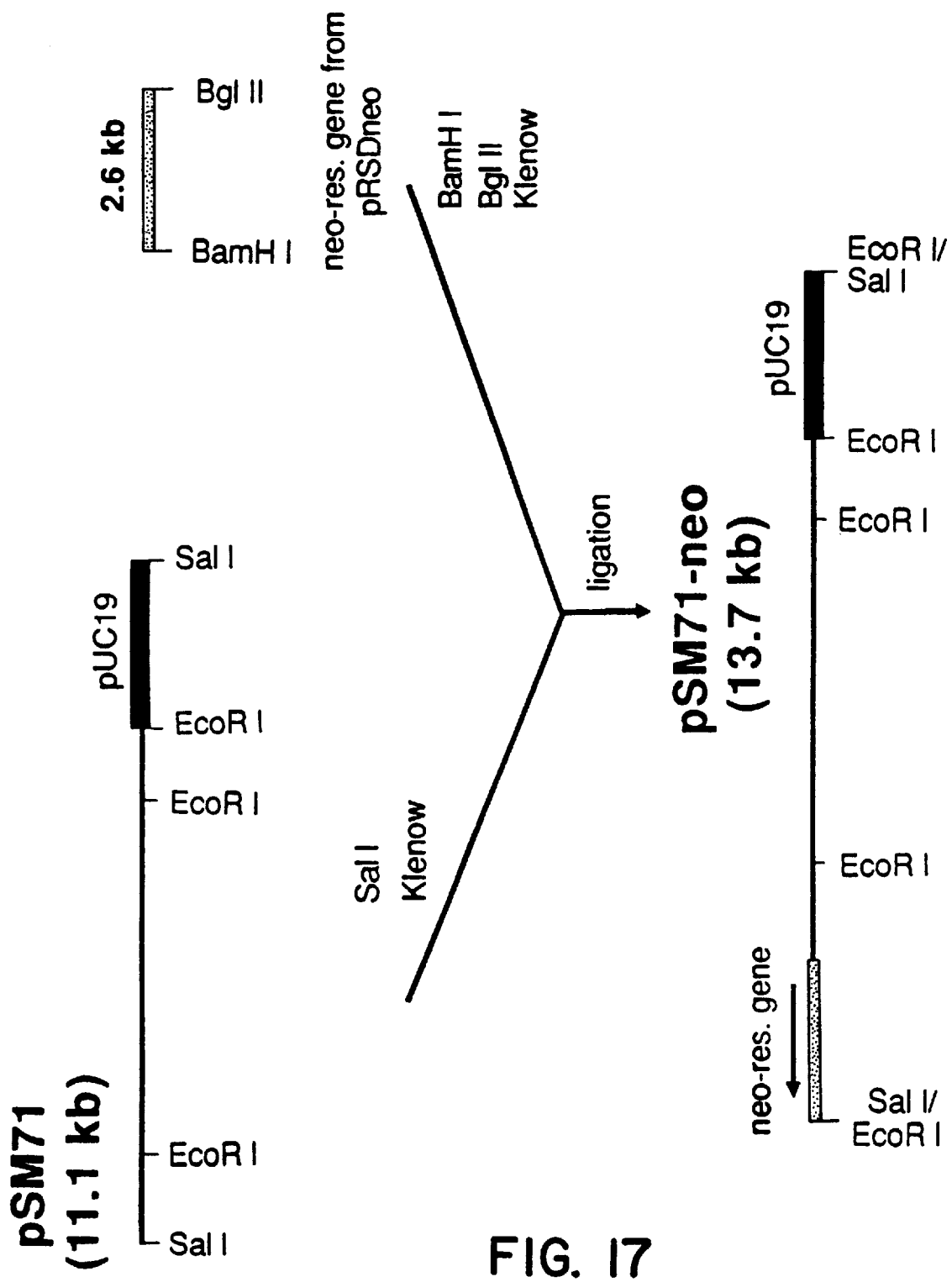

FIG. 17. Construction of pSM71-neo. A 8.4 kb SalI fragment of the BAV3 genome which falls between m.u. 0 and 24 was isolated and inserted into pUC19 at the SalI-SmaI site to generate pSM71. The plasmid, pRSDneo (Fitzpatrick et al (1990) *Virology* 176:145–157) contains the neomycin-resistant (neo$^r$ gene flanked with the simian virus 40 (SV40) regulatory sequences originally from the plasmid, pSV2neo (Southern et al (1982) *J. Mol. Appl. Genet* 1:327–341) after deleting a portion of the SV40 sequences upstream of the neo$^r$ gene to remove several false initiation codons. A 2.6 kb fragment containing the neo$^r$ gene under the control of the SV40 regulatory sequences, was obtained from the plasmid, pRSDneo after digestion with BamHI and BglII, and cloned into pSM71 at the SalI site by blunt end ligation to obtain pSM71-neo containing the neo$^r$ gene in the E1 parallel orientation.

Figure 18:
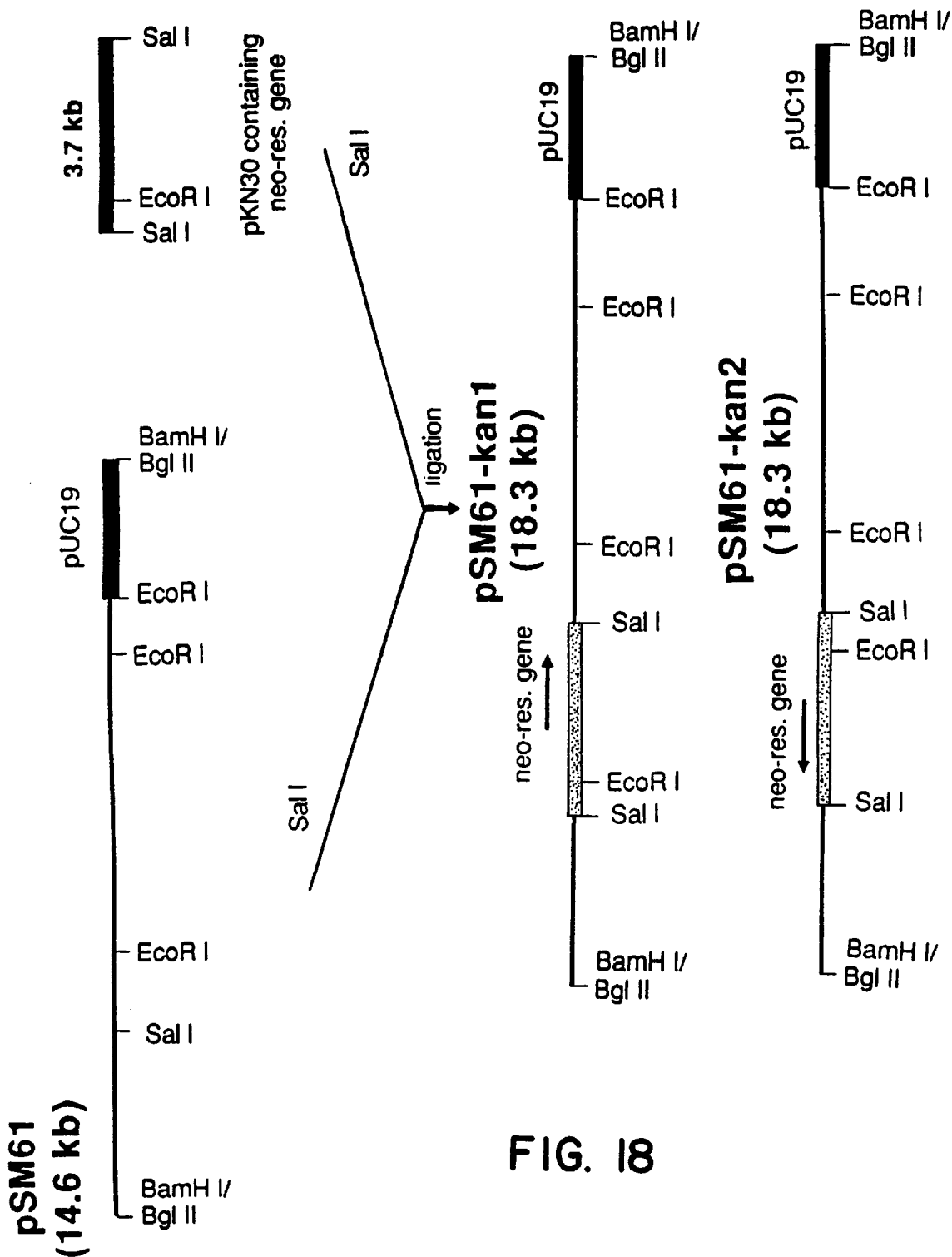

FIG. 18. Construction of pSM61-kan 1 and pSM61-kan2. A 11.9 kb BglII fragment of the BAV3 genome which extends between m.u. 0 and 34 was purified and introduced into pUC19 at the BamHI-HincII site to obtain pSM61. The plasmid, pKN30 contains the neo$^r$ gene along with SV40 promoter and polyadenylation sequences from the plasmid pSV2neo without any modification. The entire pKN30 plasmid was inserted into pSM61 at the SalI site to generate pSM61-kan1 having the neo$^r$ gene in the E1 anti-parallel orientation and pSM61-kan2 when the neo$^r$ gene is in the E1 parallel orientation.

Figure 19:
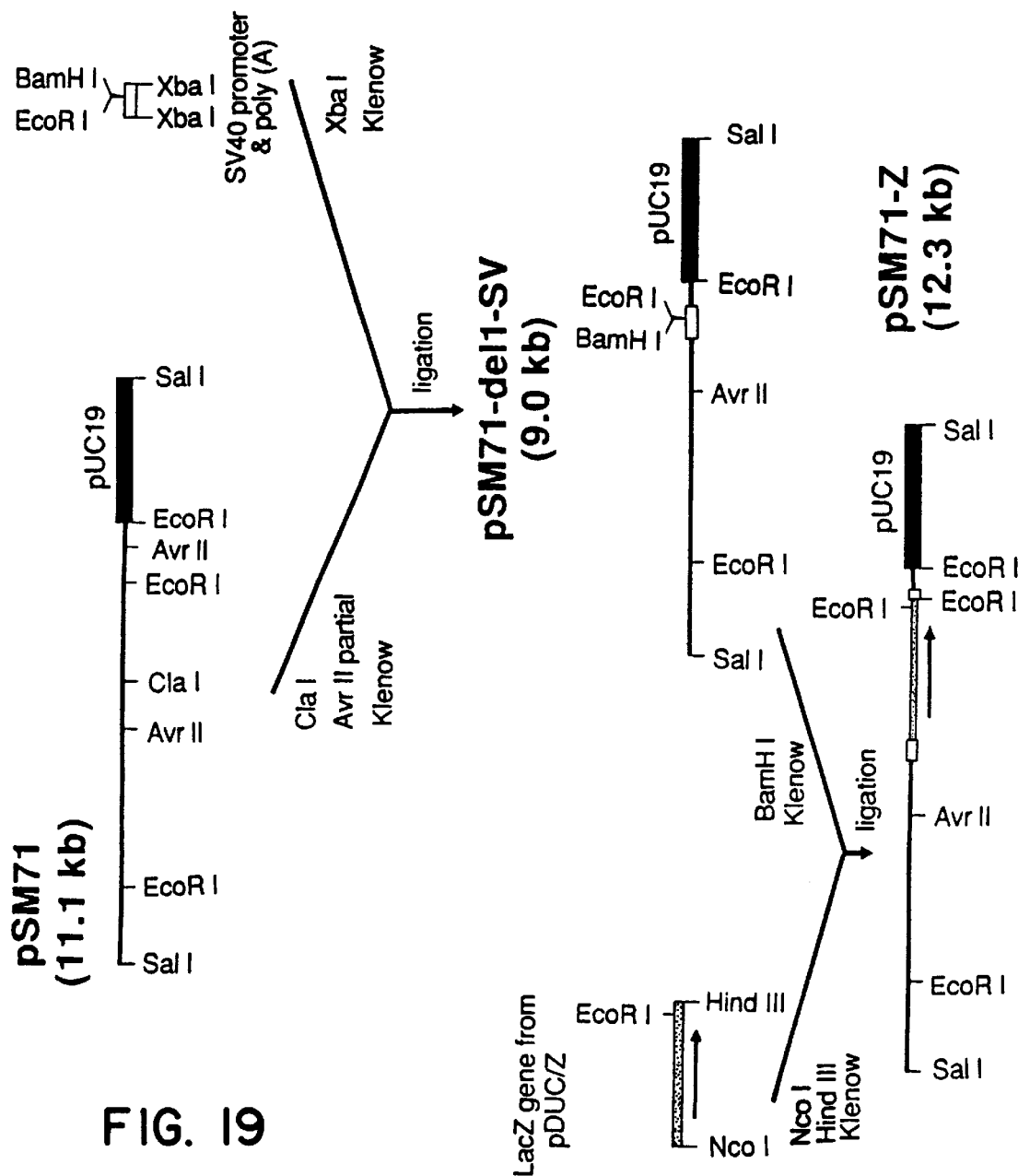

FIG. 19. Construction of an E1 transfer plasmid containing the beta-galactosidase gene.

The plasmid, pSM71 which contains the BAV3 genome between m.u. 0 and 24, was cleaved with ClaI and partially with AvrII to delete a 2.6 kb AvrII-ClaI fragment (between m.u. 1.3 and 8.7) which falls within the E1 region. A 0.5 kb fragment containing the SV40 promoter and polyadenylation sequences was obtained from pFG144K5-SV by digesting with XbaI and inserted into pSM71 to replace the 2.6 kb deletion to generate pSM71-del1-SV. A 3.26 kb fragment containing the bacterial beta-galactosidase gene was isolated from pDUC/Z (Liang et al (1993) *Virology* 195:42–50) after cleavage with NcoI and HindIII and cloned into pSM71-del1-SV at the BamHI site to put the beta-galactosidase gene under the control of the SV40 regulatory sequences to obtain pSM71-Z.

MODES OF CARRYING OUT THE INVENTION

The practice of the present invention will employ, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984). Sambrook et al., Molecular Cloning: A Laboratory Manual (2nd Edition); vols. I, II & III (1989).

A. Definitions

In describing the present invention, the following terminology, as defined below, will be used.

A "replicon" is any genetic element (e.g., plasmid, chromosome, virus) that functions as an autonomous unit of DNA replication in vivo; i.e., is capable of replication under its own control.

A "vector" is a replicon, such as a plasmid, phage, cosmid or virus, to which another DNA segment may be attached so as to bring about the replication of the attached segment.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments of DNA from viruses, plasmids, and chromosomes). In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence will usually be located 3' to the coding sequence.

A "transcriptional promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAAT" boxes. Procaryotic promoters contain Shine-Dalgarno sequences in addition to the −10 and −35 consensus sequences.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence or sequence encoding is "operably linked to" or "under the control of" control sequences in a cell when RNA polymerase will bind the promoter sequence and transcribe the coding sequence into MRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols. I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Bovine host" refers to cattle of any breed, adult or infant.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Fusion protein" is usually defined as the expression product of a gene comprising a first region encoding a leader sequence or a stabilizing polypeptide, and a second region encoding a heterologous protein. It involves a polypeptide comprising an antigenic protein fragment or a full length BAV protein sequence as well as (a) heterologous sequence (s), typically a leader sequence functional for secretion in a recombinant host for intracellularly expressed polypeptide, or an N-terminal sequence that protects the protein from host cell proteases, such as SOD. An antigenic protein fragment is usually about 5–7 amino acids in length.

"Native" proteins or polypeptides refer to proteins or polypeptides recovered from BAV or BAV-infected cells. Thus, the term "native BAV polypeptide" would include naturally occurring BAV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

A "substantially pure" protein will be free of other proteins, preferably at least 10% homogeneous, more preferably 60% homogeneous, and most preferably 95% homogeneous.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or the like, either (i) the prevention of infection or reinfection (prophylaxis), or (ii) the reduction or elimination of symptoms of an infection. The vaccine comprises the recombinant BAV itself or recombinant antigen produced by recombinant BAV.

By "infectious" is meant having the capacity to deliver the viral genome into cells.

B. General Method

The present invention identifies and provides a means of deleting part or all of the nucleotide sequence of bovine adenovirus E1 and/or E3 gene regions to provide sites into which heterologous or homologous nucleotide sequences encoding foreign genes or fragments thereof can be inserted to generate bovine adenovirus recombinants. By "deleting part of" the nucleotide sequence is meant using conventional genetic engineering techniques for deleting the nucleotide sequence of part of the E1 and/or E3 region.

Various foreign genes or coding sequences (prokaryotic, and eukaryotic) can be inserted in the bovine adenovirus nucleotide sequence, e.g., DNA, in accordance with the present invention, particularly to provide protection against a wide range of diseases and many such genes are already known in the art. The problem heretofore having been to provide a safe, convenient and effective vaccine vector for the genes or coding sequences.

It is also possible that only fragments of nucleotide sequences of genes can be used (where these are sufficient to generate a protective immune response) rather than the complete sequence as found in the wild-type organism. Where available, synthetic genes or fragments thereof can also be used. However, the present invention can be used with a wide variety of genes, fragment and the like, and is not limited to those set out above.

In some cases the gene for a particular antigen can contain a large number of introns or can be from an RNA virus, in these cases a complementary DNA copy (cDNA) can be used.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

The foreign protein produced by expression in vivo in a recombinant virus-infected cell may be itself immunogenic.

More than one foreign gene can be inserted into the viral genome to obtain successful production of more than one effective protein.

Thus with the recombinant virus of the present invention, it is possible to provide protection against a wide variety of diseases affecting cattle. Any of the recombinant antigenic determinant or recombinant live virus of the invention can be formulated and used in substantially the same manner as described for the antigenic determinant vaccines or an live vaccine vectors.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host an "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bovine pathogens such as bovine rotavirus, bovine coronavirus, bovine herpes virus type 1, bovine respiratory syncytial virus, bovine parainfluenza virus type 3 (BPI-3), bovine diarrhea virus, *Pasteurella haemolytica, Haemophilus somnus* and the like. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity in combination with systemic immunity, which plays an important role in protection against pathogens infecting the gastrointestinal tract.

In addition, the vaccine be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between $10^3$ pfu and $10^8$ pfu and the like can be used. As with in vitro subunit vaccines, additional dosages can be given as determined by the clinical factors involved.

In one embodiment of the invention, a number of recombinant cell lines are produced according to the present invention by constructing an expression cassette comprising the BAV E1 region and transforming host cells therewith to provide cell lines or cultures expressing the E1 proteins. These recombinant cell lines are capable of allowing a recombinant BAV, having an E1 gene region deletion replaced by heterologous nucleotide sequence encoding for a foreign gene or fragment, to replicate and express the desired foreign gene or fragment thereof which is encoded within the recombinant BAV. These cell lines are also extremely useful in generating recombinant BAV, having an E3 gene deletion replaced by heterologous nucleotide sequence encoding for a foreign gene or fragment, by in vivo recombination following DNA-mediated cotransfection.

In one embodiment of the invention, the recombinant expression cassette can be obtained by cleaving the wild-type BAV genome with an appropriate restriction enzyme to produce a DNA fragment representing the left end or the right end of the genome comprising E1 or E3 gene region sequences, respectively and inserting the left or right end fragment into a cloning vehicle, such as plasmid and thereafter inserting at least one DNA sequence encoding a foreign protein, into E1 or E3 deletion with or without the control of an exogenous promoter. The recombinant expression cassette is contacted with the wild-type BAV DNA through homologous recombination or other conventional genetic engineering method within an E1 transformed cell line to obtain the desired recombinant.

The invention also includes an expression system comprising an bovine adenovirus expression vector wherein a heterologous nucleotide, e.g. DNA, replaces part or all of the E3 region and/or part or all of the E1 region. The expression system can be used wherein the foreign nucleotide sequences, e.g. DNA, is with or without the control of any other heterologous promoter.

The BAV E1 gene products of the adenovirus of the invention transactivate most of the cellular genes, and therefore, cell lines which constitutively express E1 proteins can express cellular polypeptides at a higher level than normal cell lines. The recombinant mammalian, particularly bovine, cell lines of the invention can be used to prepare and isolate polypeptides, including those such as (a) proteins associated with adenovirus E1A proteins: e.g. p300, retinoblastoma(Rb) protein, cyclins, kinases and the like.; (b) proteins associated with adenovirus E1B protein: e.g. p53 and the like.; (c) growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IFG-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity and the like; (f) other cellular proteins such as actins, collagens, fibronectins, integrins, phospholipids, proteoglycans, histones and the like, and (g) proteins involved in regulation of transcription such as TATA-box-binding protein (TBP), TBP-associated factors (TAFs). SPI binding protein and the like.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are recently being used by those of skill in the art to replace a defective gene or portion thereof. Examples of foreign genes nucleotide sequences or portions thereof that can be incorporated for use in a conventional gene therapy include, cystic fibrosis transmembrane conductance regulator gene, human minidystrophin gene, alphal-antitrypsin gene and the like.

EXAMPLES

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

Cells and Viruses

Cell culture media and reagents were obtained from GIBCO/BRL Canada (Burlington, Ontario, Canada). Media were supplemented with 25 mM Hepes and 50 µg/ml gentamicin. MDBK cells or MDBK cells transformed with a plasmid containing BAV3 E1 sequences were grown in MEM supplemented with 10% Fetal bovine serum. The wild-type BAV3 ((strain WBR-1) (Darbyshire et al, 1965 *J. Comparative Pathology* 75:327) was kindly provided by Dr. B. Darbyshire, University of Guelph, Guelph, Canada) and BAV3-luciferase recombinants working stocks and virus titrations were done in MDBK cells.

Enzymes, Bacteria and Plasmids

Restriction endonucleases, polymerase chain reaction (PCR) and other enzymes required for DNA manipulations were purchased from Pharmacia LKB Biotechnology (Canada) Ltd. (Dorval, Quebec, Canada), Boehringer-Mannheim, Inc. (Laval or Montreal, Quebec, Canada), New England BioLabs (Beverly, Mass.), or GIBCO/BRL Canada (Burlington, Ontario, Canada) and used as per manufacturer's instructions. Restriction enzyme fragments of BAV3 DNA were inserted into pUC18 or pUC19 (Yanich-Penon et al (1985) *Gene* 33:103–109) following standard procedures (Sambrook et al (1989) Molecular Cloning: A Laboratory Manual, 2nd ed. Cold Spring Harbour Laboratory, New York). *E. coli* strain DH5 (supE44 hsdR17 recA1 endA1 gyrA96 thi-1 relA1) was transformed with recombinant plasmids by electroporation (Dower et al. (1988) *Nuc. Acids Res.*, 16:6127–6145). Plasmid DNA was prepared using the alkaline lysis procedure (Bernboim and Doly (1978) *Nuc. Acids Res.*, 7:1513–1523). The plasmid, pSVOA/L containing the entire cDNA encoding firefly luciferase (de Wet et al (1987) *Mol. Cell. Biol.* 7:725–737), was a gift from D. R. Helinski, University of California, San Diego, La Jolla, Calif.

Construction of Recombinant BAV3

MDBK cells transformed with a plasmid containing BAV3 E1 sequences were cotransfected with the wt BAV3 DNA digested with PvuI and the plasmid, pSM51-Luc (FIGS. 9 and 10) using the lipofection-mediated cotransfection protocol (GIBCO/BRL, Life Technologies, Inc., Grand Island, N.Y.). The virus plaques produced following cotransfection were isolated, plaque purified and the presence of the luciferase gene in the BAV3 genome was detected by agarose gel electrophoresis of recombinant virus DNA digested with appropriate restriction enzymes.

Southern Blot and Hybridization

Mock or virus-infected MDBK cells were harvested in lysis buffer (500 $\mu$g/ml pronase in 0.01 M Tris, pH 7.4, 0.01 M EDTA, 0.5% SDS) and DNA was extracted (Graham et al (1991) Manipulation of adenovirus vectors In: Methods and Molecular Biology, 7:Gene Transfer and Expression Techniques (Eds. Murray and Walker) Humana Press, Clifton, N.J. pp. 109–128). 100 ng DNA was digested either with BamHI, EcoRI or XbaI and resolved on a 1% agarose gel by electrophoresis. DNA bands from the agarose gel were transferred to a GeneScreenPlus™ membrane (Du Pont Canada Inc. (NEN Products), Lachine, Quebec, Canada) by the capillary blot procedure (Southern, E. M. (1975) *J. Mol. Biol.* 98:503–517). Probes were labeled with $^{32}$P using an Oligolabeling Kit (Pharmacia LKB Biotechnology (Canada) Ltd., Dorval, Quebec, Canada) and the unincorporated label was removed by passing the labeled probe through a sephadex G-50 column (Sambrook et al (1989) supra). Probes were kept in a boiling water bath for 2 min and used in hybridization experiments following GeneScreenPlus™ hybridization protocol. The DNA bands which hybridized with the probe were visualized by autoradiography.

Luciferase Assays

The protocol was essentially the same as described (Mittal et al (1993) *Virus Res.* 28:67–90). Briefly, MDBK cell monolayers in 25 mm multi-well dishes (Corning Glass Works, Corning, N.Y.) were infected in duplicate either with BAV3-Luc (3.1) or BAV3-Luc (3.2) at a m.o.i. of 50 p.f.u. per cell. At indicated time points post-infection, recombinant virus-infected cell monolayers were washed once with PBS (0.137 M NaCl, 2.7 mM KCl, 8 mM $Na_2HPO_4$, 1.5 mM $KH_2PO_4$) and harvested in 1 ml luciferase extraction buffer (100 mM potassium phosphate, pH 7.8, 1 mM dithiothreitol). The cell pellets were resuspended in 200 $\mu$l of luciferase extraction buffer and lysed by three cycles of freezing and thawing. The supernatants were assayed for luciferase activity. For the luciferase assay, 20 $\mu$l of undiluted or serially diluted cell extract was mixed with 350 $\mu$l of luciferase assay buffer (25 mM glycylglycine, pH 7.8, 15 mM $MgCl_2$, 5 mM ATP) in a 3.5 ml tube (Sarstedt Inc., St-Laurent, Quebec, Canada). Up to 48 tubes can be kept in the luminometer rack and the equipment was programed to inject 100 $\mu$l of luciferin solution (1 mM luciferin in 100 mM potassium phosphate buffer, pH 7.8) in the tube present in the luminometer chamber to start the enzyme reaction. The Luminometer (Packard Picolite Luminometer, Packard Instrument Canada, Ltd., Mississauga, Ontario, Canada) used in the present study produced 300 to 450 light units of background count in a 10 sec reaction time. Known amounts of the purified firefly luciferase were used in luciferase assays to calculate the amount of active luciferase present in each sample.

Western Blotting

Mock or virus-infected MDBK cells were lysed in 1:2 diluted 2× loading buffer (80 mM Tris-HCl, pH 6.8, 0.67 M urea, 25% glycerol, 2.5% SDS, 1 M mercaptoethanol, 0.001% bromophenol blue), boiled for 3 min and then centrifuged to pellet cell debris. Proteins were separated by SDS-polyacrylamide gel electrophoresis (SDS-PAGE) on 0.1% SDS-10% polyacrylamide gels (Laemmli, et al (1970) *Nature* 227:680–685). After the end of the run, polypeptide bands in the gel were electrophoretically transferred to a nitrocellulose membrane (Bio-Rad Laboratories, Richmond, Calif.). The membrane was incubated at room temperature for 2 h with 1:4000 diluted rabbit anti-luciferase antibody (Mittal et al (1993) supra). The binding of anti-luciferase antibody to the specific protein band/s on the membrane was detected with 1:5000 diluted horseradish peroxidase conjugated-goat anti-rabbit IgG (Bio-Rad Laboratories, Richmond, Calif.) and with an ECL Western blotting detection system (Amersham Canada Ltd., Oakville, Ontario).

Example 1

Cloning of BAV3 E1 Region DNA for Sequencing

To complement the restriction site (Kurokawa et al, 1978 *J. Virol.*, 28:212–218; Hu et al, 1984 *J. Virol.* 49:604–608) other restriction enzyme sites in the BAV3 genome were defined. The 8.4 kilobase pair (kb) SalI B fragment which extends from the left end of the genome to approximately 24% was cloned into the SmaI-SalI sites of pUC18 essentially as described previously (Graham et al, 1989 *EMBO Journal* 8:2077–2085). Beginning at the left end of the BAV3 genome, the relevant restriction sites used for subsequent subcloning and their approximate positions are: SacI (2%), EcoRI (3.5%), HindIII (5%), SacI (5.5%), SmaI (5.6%) and HindIII (11%). Through the use of appropriate restriction enzymes, the original plasmid was collapsed to contain smaller inserts which could be sequenced using the pUC universal primers. Some fragments were also subcloned in both pUC18 and pUC19 to allow confirmational sequencing in both directions. These procedures, together with the use of twelve different oligonucleotide primers hybridizing with BAV3 sequences, allowed to sequence the BAV3 genome from its left end to the HindIII site at 11%.

To ensure that some features of the sequence obtained were not unique to the initial clone selected for sequencing, two more pUC19 clones were prepared containing the SalI fragment from a completely independent DNA preparation. These clones were used to confirm the original sequence for the region from approximately 3% to 5.5% of the BAV3 genome.

DNA sequencing reactions were based on the chain-termination method (Sanger et al. 1977 *PNAS, USA* 74:5463–5467) and manual sequencing followed the DNA sequencing protocol described in the Sequenase kit produced by US Biochemical. [α-$^{35}$S]dATPs was obtained from Amersham Canada Ltd. All oligonucleotides used as primers were synthesized by the Central Facility of the Molecular Biology and Biotechnology Institute (MOBIX) at McMaster University, Hamilton, Ontario. The entire region (0 to 11%) of the BAV3 genome was sequenced by at least two independent determinations for each position by automated sequencing on a 373A DNA Sequencer (Applied Biosystems) using Taq-Dye terminators. Over half of the region was further sequenced by manual procedures to confirm overlaps and other regions of interest.

DNA sequence analysis and protein comparisons were carried out on a MICROGENIE program.

Example 2
Coding Sequences of the BAV3 E1 Region

Figure 2A:
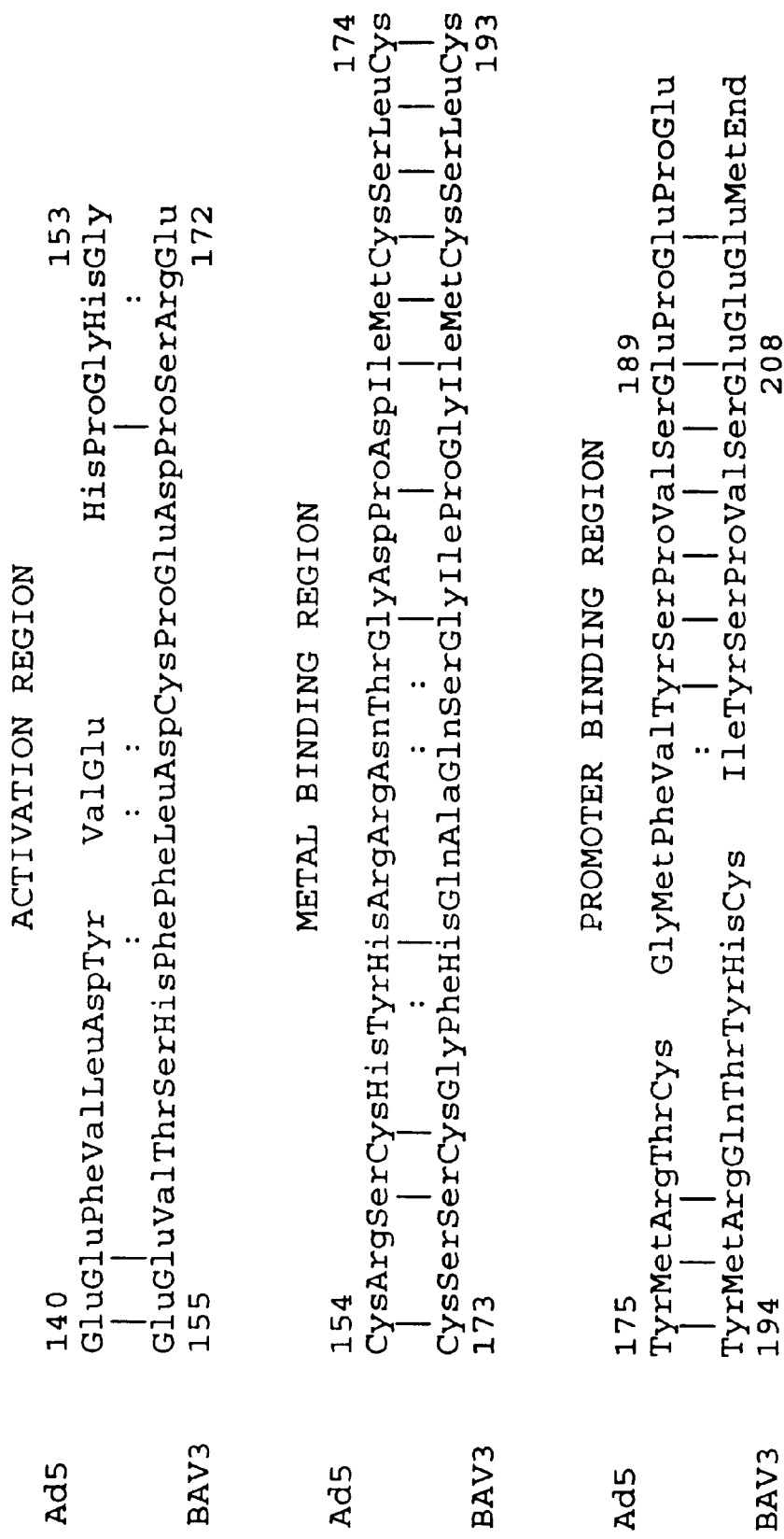

BAV3 genomic DNA, from the left end of the genome to the HindIII site at approximately 11%, was cloned into plasmids and sequenced by a combination of manual and automated sequencing. An examination of the resultant BAV3 E1 genomic sequence (FIG. 1) revealed a number of interesting features relevant both to transactivation and to other functions associated with adenovirus E1 proteins. On the basis of open reading frames (ORFs) it was possible to assign potential coding regions analogous to those defined in human Ad5 (HAd5). As shown in FIG. 1, ORFs corresponding roughly to the first exon and unique region of HAd5 E1A as well are ORFs corresponding to the 19k and 58k proteins of E1B and the ORF corresponding to protein IX were all defined in this sequence. The open reading frame defining the probable E1A coding region begins at the ATG at nt 606 and continues to a probable splice donor site at position 1215. The first consensus splice acceptor site after this is located after nt 1322 and defines an intron of 107 base pairs with an internal consensus splice branching site at position 1292. The putative BAV3 E1A polypeptide encoded by a message corresponding to these splice sites would have 211 amino acids and a unmodified molecular weight of 23,323. The major homology of the protein encoded by this ORF and HAd5 E1A is in the residues corresponding to CR3 (shown in FIG. 2). The homology of amino acid sequences on both sides of the putative intron strengthens the assignment of probable splice donor and acceptor sites. The CR3 has been shown to be of prime importance in the transactivation activity of HAd5 E1A gene products. As seen in FIG. 2A the homology of this sequence in the BAV3 protein to the corresponding region of the 289R E1A protein of HAd5 includes complete conservation of the $CysX_2CysX_{13}CysX_2Cys$ sequence motif (SEQ ID NO: 30) which defines the metal binding site of this protein (Berg, 1986 *Science* 232:485–487) as well as conservation of a number of amino acids within this region and within the promoter binding region as defined by Lillie and Green 1989 *Nature* 338:39–44).

The only other region of significant homology between the BAV3 E1A protein and that of HAd5 was a stretch of amino acids known to be important in binding of the cellular Rb protein to the HAd5 E1A protein (Dyson et al, 1990 *J. Virol.* 64:1353–1356). As shown in FIG. 2B, this sequence, which is located between amino acids 120 and 132 in the CR2 region of HAd5 E1A, is found near the amino (N-) terminus of the BAV3 protein between amino acids 26 and 37.

An open reading frame from the ATG at nt 1476 to the termination signal at 1947 defines a protein of 157 amino acids with two regions of major homology to the HAd5 E1B 19k protein. As shown in FIG. 3 both the BAV3 and the HAd5 proteins have a centrally located hydrophobic amino acid sequence. The sequence in BAV3, with substitutions of valine for alanine and leucine for valine, should result in a somewhat more hydrophobic pocket than the corresponding HAd5 region. The other portion of HAd5 19k that may be conserved in the BAV3 protein is the serine rich sequence found near the N-terminus (residues 20 to 26) in HAd5 19k and near the C-terminus (residues 136 to 142) in the BAV3 protein (also shown in FIG. 3).

On ORF beginning at the ATG at nt 1850 and terminating at nt 3110 overlaps the preceding BAV3 protein reading frame and thus has the same relationship to it as does the HAd5 E1B 56k protein to E1B 19k protein. As shown in FIG. 4 this BAV3 protein of 420R and the corresponding HAd5 E1B 56k protein of 496R show considerable sequence homology over their C-terminal 346 residues. The N-terminal regions of these proteins (not depicted in the figure) show no significant homology and differ in overall length.

Following the E1B ORFS, the open reading frame beginning at nt 3200 and ending at the translation terminator TAA at nt 3575 defines a protein of 125R with an unmodified molecular weight of 13,706. As seen in FIG. 5 this protein shares some homology with the structural protein IX of HAd5 particularly in N-terminal sequences.

Possible Transcription Control Regions in BAV3 E1

The inverted terminal repeats (ITR) at the ends of the BAV3 genome have been shown to extend to 195 nt (Shinagawa et al, 1987 *Gene* 55:85–93). The GC-rich 3' portion of the ITR contains a number of consensus binding sites for the transcription stimulating protein SP1 (Dynan and Tijan (1983) *Cell* 35:79–87) and possible consensus sites for the adenovirus transcription factor (ATF) (Lee et al. (1987) *Nature* 325:368–372) occur at nts 60 and 220. While there are no exact consensus sites for the factors EF-1A (Bruder and Healing (1989) *Mol. Cell Biol.* 9:5143–5153) or E2F (Kovesdi et al, 1987 *PNAS, USA* 84:2180–2184) upstream of the ATG at nt 606, there are numerous degenerate sequences which may define the enhancer region comparable to that seen in HAd5 (Hearing and Shenk, 1986 *Cell* 45:229–236).

The proposed BAV3 E1A coding sequence. terminates at a TGA residue at nt 1346 which is located within a 35 base pair sequence which is immediately directly repeated (see FIG. 1). Two repeats of this sequence were detected in three independently derived clones for a plaque purified stock of BAV3. The number of direct repeats can vary in any BAV3 population though plaque purification allows for isolation of a relatively homogeneous population of viruses. That direct repeats in the sequences can function as promoter or enhancer elements for E1B transcription is being tested. There are no strong polyA addition consensus sites between the E1A and the E1B coding sequences and in fact no AATAA sequence is found until after the protein IX coding sequences following E1B. The TATAAA sequence beginning at nt 1453 could function as the proximal promoter for E1B but it is located closer to the ATG at 1476 than is considered usual (McKnight et al, 1982 *Science* 217:316–322). The TATA sequence located further upstream immediately before the proposed E1A intron sequence also seems inappropriately positioned to serve as a transcription box for the E1B proteins. There are clearly some unique features in this region of the BAV3 genome.

The transcriptional control elements for the protein IX transcription unit are conventional and well defined. Almost immediately following the open reading frame for the larger E1B protein there is, at nt 3117, a SP1 binding sequence. This is followed at 3135 by a TATAAAT sequence which could promote a transcript for the protein IX open reading frame beginning at the ATG at 3200 and ending with the TAA at 3575. One polyA addition sequence begins within the translation termination codon and four other AATAA sequences are located at nts 3612, 3664, 3796 and 3932.

In keeping with the general organization of the E1A region of other adenoviruses, the BAV3E1A region contains an intron sequence with translation termination codons in all three reading frames and which is therefore probably deleted by splicing from all E1A mRNA transcripts. The largest possible protein produced from the BAV3 E1A region will have 211 amino acid residues and is the equivalent of the 289 amino acid protein translated from the 13s mRNA of HAd5. Two striking features in a comparison of these proteins are the high degree of homology in a region corresponding to CR3 and the absence in BAV3 of most of amino acids corresponding to the second exon of HAd5. In fact the only amino acids encoded in the second exon of BAV3 are, those which are considered to constitute part of CR3. A great deal of work carried out with HAd5 has identified the importance of the CR3 sequences in transactivation of other HAd5 genes. While a detailed analysis of the corresponding BAV3 region and its possible role in transactivation of BAV3 genes needs to be carried out, it is none-the-less interesting to note a couple of possibly pertinent features. The HAd5 CR3 region has been operationally subdivided into three regions (Lillie et al, 1989 *Nature* 338:39–44; see FIG. 8); an N-terminal region from 139 to 153 which has four acidic residues and is thought to be important in transcription activation, a central, metal-binding, region defined by the Cys-$X_2$-Cys-$X_{13}$-Cys$X_2$-Cys sequence (SEQ ID NO: 30) which is essential for both promoter binding and activation, and a C-terminal region (residues 175–189) which is essential for promoter binding. Since, in most instances, E1A protein is thought not to interact directly with DNA (Ferguson et al 1985), the promoter binding regions may be involved in forming associations with proteins which then allow association with DNA. In FIG. 2*a* the BAV3 E1A protein contains the central, metal binding domain and has considerable homology in the carboxy portion of this region. The BAV3 E1A protein also shows identity of sequence with HAd5 in the carboxy 6 amino acids of the promoter binding domain. These features may allow the BAV3 E1A protein to interact with the same transcription activating factors required for HAd5 E1A function. In contrast, except for a Glu—Glu pair there is little homology between the bovine and human viruses in the activation domain. The fact that this domain can be functionally substituted by a heterologous acidic activation sequence (Lillie et al, 1989 supra) suggests that protein specificity is not required in this region and this may allow the BAV3 E1A protein to function in the activation of BAV3 genes. The BAV3 E1A activation region contains six acidic residues in the 18 residues amino to the metal binding domain.

The other interesting feature of BAV3 E1A, which is undoubtedly relevant to the oncogenic potential of this virus, is the presence of the sequence Asp27-Leu-Glu-Cys-His-Glu which conforms to, a core sequence known to be important in the binding of cellular Rb and related proteins by the transforming proteins of a number of DNA tumor viruses (Dyson et al, 1990 supra). From deletion mutant analysis there is a clear association between the potential of HAd5 E1A proteins to bind Rb and the ability of the protein to induce morphological transformation in appropriate cells (see references in Dyson et al, 1990 supra). The BAV3 E1A protein is distinct from its HAd5 counterpart in the relative position of this Rb binding sequence which is in the CR2 of HAd5 E1A and near the N-terminus of the BAV3 E1A protein.

Through the use of alternative splice sites HAd5 E1A transcripts can give rise to at least 5 distinct mRNA species (Berk et al, 1978 *Cell* 14:695–711; Stephens et al, 1987 *EMBO Journal* 6:2027–2035). Whether BAV3, like HAd5, can generate a number of different mRNA species through the use of alternative splice sites in the E1A transcripts remains to be determined. For example a potential splice donor site which could delete the sequence equivalent to the unique sequence of HAd5 is present immediately after nt 1080 but it is not known if this site is actually used.

HAd5 E1B encodes two proteins (19k and 56k) either of which can cooperate with E1A, by pathways which are additive and therefore presumably independent (McLorie et al, 1991 *J. Gen. Virol*. 72:1467–1471), to produce morphological transformation of cells in culture (see for example: Branton et al, 1985 supra; Graham, 1984 supra). The significance of the conservation of the hydrophobic stretch of amino acids in the central portion of the shorter E1B proteins of HAd5 and BAV3 is not clear as yet. A second short region of homology Gln-Ser-Ser-X-Ser-Thr-Ser at residue 136 near the C-terminus of the BAV3 protein is located near the N-terminus at residue 20 in the HAd5 19k protein. The major difference in both length and sequence of the larger (420R) E1B protein of BAV3 from the corresponding HAd5 protein (496R) is confined to the N-terminus of these proteins. The two proteins show considerable evolutionary homology in the 345 amino acids that extend to their C-termini. A similar degree of homology extends into the N-terminal halves of protein IX of BAV3 and HAd5. Taken together these analyses suggest that while BAV3 and the human adenoviruses have diverged by simple point mutational events in some regions, more dramatic genetic events such as deletion and recombination may have been operating in other regions particularly those defining the junction between E1A and E1B.

Example 3

Cloning and Sequencing of the BAV3 E3 and Fibre Genes

Figure 6:
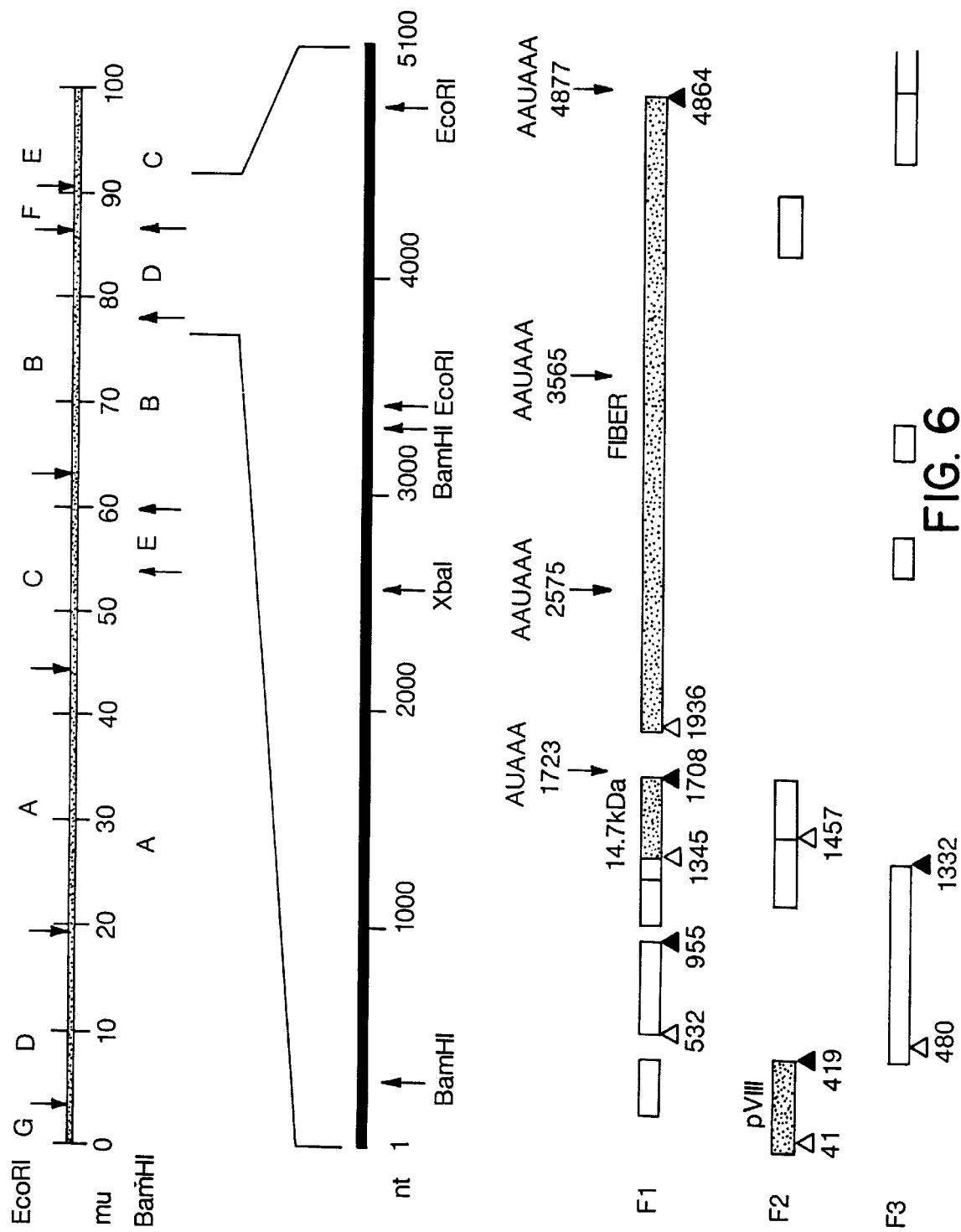
FIG. 6. The genome of BAV3 showing the location of EcoRI, XbaI and BAMHI sites and the structure of the 5100 bp segment from 77 to 92 m.u. ORFs for the upper strand which can encode 60 amino acids or more are represented by bars. Shaded portions indicate regions of similarity to pVIII, 14.7 K E3 and fibre proteins of HAd2 or –5. The first methionine followed by a stretch of amino acids of at least 50 is shown by an open triangle. Termination codons for ORFs likely to code for viral proteins are shown by closed triangles.

The general organization of adenovirus genomes seems to be relatively well conserved so it was possible to predict, from the locations of a number of HAd E3 regions, that BAV E3 should lie between map units (m.u.) 77 to 86. To prepare DNA for cloning and sequencing, BAV3 (strain WBR-1) was grown in Madin-Darby bovine kidney (MDBK) cells, virions were purified and DNA was extracted (Graham, F. L. & Prevec, L. (1991) Methods in Molecular Biology, vol. 7, Gene Transfer and Expression Protocols, pp. 109–146. Edited by E. J. Murray, Clifton, N.J.; Humana Press.). Previously published restriction maps for EcoRI and BamHI (Kurokawa et al., 1978) were confirmed (FIG. 6). The BamHI D and EcoRI F fragments of BAV3 DNA were isolated and inserted into pUC18 and pUC19 vectors, and nested sets of deletions were made using exonuclease III and S1 nuclease (Henikoff, S. (1984) *Gene*, 28:351–359). The resulting clones were sequenced by the dideoxynucleotide chain termination technique (Sanger, F., Nicklen, S. & Coulson, A. R. (1977) *Proceedings of the National Academy of Sciences, U.S.A.*, 74:5463–5467). The nucleotide sequence from positions 1 to 287 was obtained from the right end of the BamHI B fragment (FIG. 6). The sequence of the regions spanning (i) the BamHI site at nucleotide 3306 and the EcoRI site at nucleotide 3406, and (ii) the EcoRI site at nucleotide 4801 and the nucleotide 5100 was obtained from a plasmid containing the XbaI C fragment (m.u. 83 to 100; not shown) using primers hybriding to BAV3 sequences. Analysis of the sequence was performed with the aid of the PC/GENE sequence analysis package developed by Amos Bairoch, Department of Medical Biochemistry, University of Geneva, Switzerland.

The 5100 nucleotide sequence which extends between 77 and 92 m.u. of the BAV3 genome is shown in FIG. 7. The upper strand contains 14 open reading frames (ORFs) which could encode polypeptides of 60 amino acid residues or more (FIGS. 6 and 7). The lower strand contains no ORF encoding a protein of longer than 50 amino acids after an initiation codon. The predicted amino acid sequence for each ORF on the upper strand was analyzed for homology with predicted amino acid sequences from several sequenced Ads: HAd2 (Hérissé, J., Courtois, G. & Galibert, F. (1980) *Nucleic Acids Research*, 8:2173–2192; Hérissé, J., Courtois, G. & Galibert, F. (1981) *Nucleic Acids Research*, 9:1229–1249), -3(Signas, C., Akusjarvi, G. & Pettersson, U. (1985) *Journal of Virology*, 53:672–678.), -5(Cladaras, C. & Wold, W. S. M. (1985) *Virology*, 140:28–43), -7 (Hong, J. S., Mullis, K. G. & Engler, J. A. (1988) *Virology,* 167:545–553) and -35(Flomenberg, P. R., Chen, M. & Horwitz, M. S. (1988) *Journal of Virology*, 62:4431–4437), and murine Ad1 (MAd1) (Raviprakash, K. S., Grunhaus, A., El Kholy, M. A. & Horwitz, M. S. (1989) *Journal of Virology*, 63:5455–5458) and canine Ad1 (CAd1) (Dragulev, B. P., Sira, S., Abouhaidar, M. G. & Campbell, J. B. (1991) *Virology,* 183:298–305). Three of the BAV3 ORFs exhibited homology with characterized HAd proteins pVIII, fibre and the 14.7 K E3 protein. The amino acid sequence predicted from BAV3 ORF 1 shows overall identity of approximately 55% when compared to the C-terminal 75% of HAd2 pVIII (Cladaras & Wold, 1985, supra) (FIG. 8*a*), indicating that ORF 1 encodes the right end of BAd3 pVIII. Near the C-terminal end of BAd3 pVIII there is a 67 amino acid stretch (residues 59 to 125; FIG. 8*a*) which has 75% identity with HAd2 pVIII. This region has previously been shown to be highly conserved among different Ads (Cladaras & Wold, 1985, supra; Signas, C., Akusjarvi, G. & Pettersson, U. (1986) *Gene*, 50:173–184,; Raviprakash et al., 1989, supra; Dragulev et al., 1991, supra).

The fibre protein is present on the surface of the virion as long projections from each vertex of the icosahedral capsid and is involved in a number of Ad functions including attachment of the virus to the cell surface during infection, assembly of virions and antigenicity (Philipson, L. (1983) *Current Topics in Microbiology and Immunology*, 109:1–52). On the basis of the primary structure of HAd2 fibre protein, it has been proposed that the shaft region (between amino acid residues 40 and 400) is composed of a number of repeating structural motifs containing about 15 hydrophobic residues organized in two short β-sheets and two β-bends (Green, N. M., Wrigley, N. G., Russell, W. C., Martin, S. R. & McLachlan, A. D. (1983) *EMBO Journal*, 1357–1365). The amino acid sequences at the N terminus of the BAV3 ORF 6-encoded protein share about 60% identity with the HAd2 fibre protein tail, but there is little or no similarity in the knob region, and about 45% identity overall (FIG. 8*c*). The BAd3 fibre gene would encode a protein of 976 residues if no splicing occurs, i.e. 394 amino acid residues longer than the HAd2 fibre protein. The number of repeating motifs in the shaft region of the fibre protein from different Ads varies between 28 and 23 (Signas et al., 1985, supra; Chroboczek, J. & Jacrot, B. (1987) *Virology*, 161:549–554; Hong et al., 1988, supra; Raviprakash et al., 1989, supra; Dragulev et al., 1991, supra). The BAV3 fibre protein can be organized into 52 such repeats in this region (not shown), which would account for most of the difference in size compared to those of HAd2, HAd3, HAD5, HAd7, CAd1 and MAd1 (Signas et al., 1985, supra; Hérisséet al., 1980, supra; Hérissé & Galibert, 1981, supra; Hong et al., 1988, supra; Raviprakash et al., 1989, supra; Dragulev et al., 1991, supra).

HAd2 and HAd5 E3 lies between the pVIII and the fibre genes an encodes at least 10 polypeptides (Cladaras & Wold, 1985, supra). The promoter for E3 of these two serotypes lies within the sequences encoding pVIII, about 320 bp 5' of the termination codon. No consensus TATA box is found in the corresponding region of the BAV3 sequences. A non-canonical polyadenylation signal (ATAAA) for E3 transcripts is located at position 1723, between the end of the putative E3 region and the beginning of ORF 6, encoding the fibre protein, and two consensus signals are located within ORF 6 at positions 2575 and 3565. The polyadenylation signal for the fibre protein is located at nucleotide 4877. Six ORFs were identified in the BAV3 genome between the pVIII and the fibre genes, but only four (ORFs 2, 3, 4 and 5) have the potential to encode polypeptides of at least 50 amino acids after an initiation codon (FIG. 7). The amino acid sequence predicted to be encoded by ORF 2 is 307 residues long and contains eight potential N-glycosylation sites (FIG. 7) as well as a hydrophobic sequence which may be a potential transmembrane domain (PLLFAFVLCTGCAVLLTAFGPSILSGT) (SEQ ID NO: 32) between residues 262 and 289. This domain may be a part of the protein homologous to the HAd2 and HAd5 19K E3 glycoprotein (Cladaras & Wold, 1985, supra), and the proposed CAd1 22.2K protein (Dragulev et al., 1991, supra), but ORF 2 does not show appreciable homology with these proteins. The ORF 4 shows approximately 44% identity with the 14.7K E3 protein of HAd5 (FIGS. 6 and 8*b*), which has been shown to prevent lysis of virus-infected mouse cells by tumor necrosis factor (Gooding, L. R., Elmore, L. W., Tollefson, A. E., Brody, H. A. & Wold, W. S. M. (1988) *Cell*, 53:341–346; Wold, W. S. M. & Gooding, L. R. (1989) *Molecular Biology and Medicine*, 6:433–452). Analysis of the 14.7K protein sequence from HAd2, -3, -5 and -7 has revealed a highly conserved domain, which in HAd5 lies between amino acid residues 41 and 56 (Horton, T. M., Tollefson, A. E., Wold, W. S. M. & Gooding, L. R. (1990) *Journal of Virology*, 64:1250–1255). The corresponding region in the BAV3 ORF 4-encoded protein, between amino acids 70 and 85, contains 11 amino acids identical to those of the HAd5 14.7K protein conserved domain (FIG. 8*b*).

The BAV3 E3 region appears to be approximately 1.5 kbp long, about half the size of those of HAd2 and -5 (Cladaras & Wold, 1985, supra), and novel splicing events in BAV3 E3 would be required to generate more homologues to the HAd3 E3 proteins. A similarly short E3 region has been reported for MAd1 (RAviprakash et al., 1989, supra) and CAd1 (Dragulev et al., 1991, supra).

Example 4
Construction of BAV3-Luciferase Recombinants

Adenovirus-based mammalian cell expression vectors have gained tremendous importance in the last few years as a vehicle for recombinant vaccine delivery, and also in gene therapy. BAV3-based expression vectors have a greater potential for developing novel recombinant vaccines for veterinary use. To show that BAV3 E3 gene products are not essential for virus growth in cultured cells and this locus could be used to insert foreign DNA sequences, a 1.7 kb fragment containing the firefly luciferase gene was introduced in the 696 bp deletion of the E3 region of the BAV3 genome in the E3 parallel orientation to generate a BAV3 recombinant.

The rationale of using the luciferase gene is that it acted as a highly sensitive reporter gene when introduced in the E3 region of the HAd5 genome to generate HAd5-Luc recombinants (Mittal et al (1993) *Virus Res.* 28:67–90).

Figure 9:
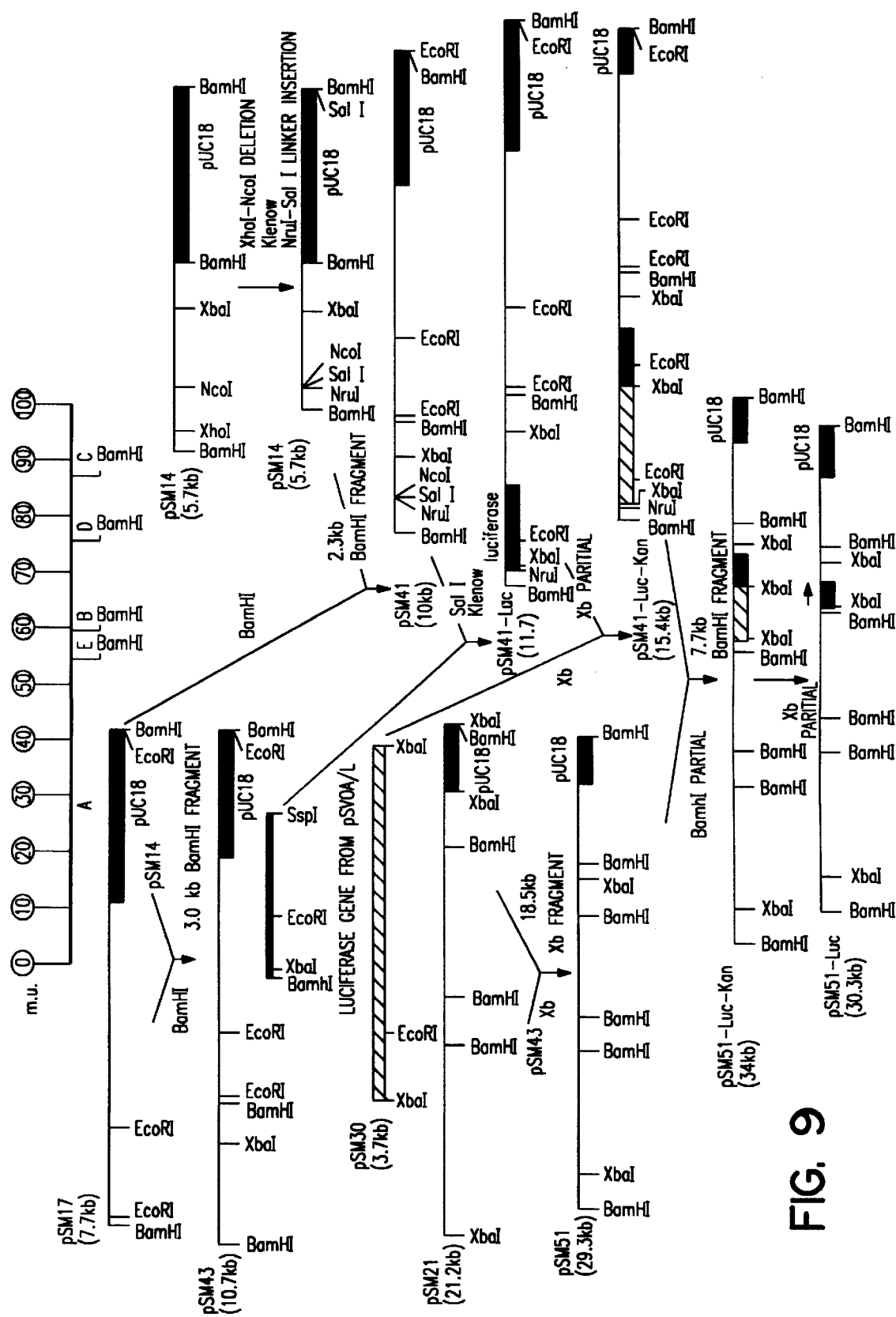
FIG. 9. Construction of BAV3 E3 transfer vector containing the firefly luciferase gene. The 3.0 kb BamHI 'D' fragment of the BAV3 genome which falls between m.u. 77.8 and 86.4, contains almost the entire E3 region (Mittal et al (1992) *J. Gen. Virol.* 73:3295–3000). This 3.0 kb fragment was isolated by digesting BAV3 DNA with BamHI and cloned into pUC18 at the BamHI site to obtain pSM14. Similarly, the 4.8 kb BamHI 'C' fragment of BAV3 DNA which extends between m.u. 86.4 and 100 was isolated and inserted into pUC18 to produce pSM17. To delete a 696 bp XhoI-NcoI fragment, pSM14 was cleaved with XhoI and NcoI, the larger fragment was purified and the ends were made blunt with Klenow fragment of DNA polymerase I and a NruI-SalI linker was inserted to generate pSM14de12. A 2.3 kb BamHI fragment containing BAV3 sequences, an E3 deletion and NruI and SalI cloning sites, was inserted into pSM17 at the BamHI site to obtain pSM41, however, this step was not required for construction of a BAV3 E3 transfer vector. A 1716 bp fragment containing the firefly luciferase gene (de Wet et al (1987) *Mol. Cell. Biol.* 7:725–737) was isolated by digesting pSVOA/L (provided by D. R. Helinski, University of California at San Diego, Calif.) with BsmI and SspI as described (Mittal et al (1993) *Virus Res.* 28:67–90), and the ends were made blunt with Klenow. The luciferase gene was inserted into pSM41 at the SalI site by blunt end ligation. The resultant plasmid was named pSM41-Luc which contained the luciferase gene in the same orientation as the E3 transcription unit. The plasmid pKN30 was digested with XbaI and inserted into pSM41-Luc (partially cleaved with XbaI) at a XbaI site present within the luciferase gene to obtain pSM41-Luc-Kan. The plasmid pSM14 was digested with BamHI and a 3.0 kb fragment was isolated and inserted into pSM17 at the BamHI site to generate pSM43. The 18.5 kb XbaI 'A' fragment of the BAV3 genome which falls between m.u. 31.5 and 84.3 was cloned into pUC18 at the XbaI site to result pSM21. A 18.5 kb XbaI fragment was purified from pSM21 after cleavage with XbaI and inserted into pSM43 at the XbaI site and the resultant plasmid was named pSM51. A 7.7 kb BamHI fragment containing the luciferase gene and kan$^r$ gene was isolated after digesting pSM41-Luc-Kan with BamHI and ligated to pSM51, partially digested with BamHI, to isolate pSM51-Luc-Kan in the presence of ampicillin and kanamycin. Finally the kan$^r$ gene was deleted from pSM51-Luc-Kan by partial cleavage with XbaI and religation to obtain pSM51-Luc.

To facilitate the insertion of the firefly luciferase gene into the E3 region of the BAV3 genome, a BAV3 E3 transfer vector containing the luciferase gene was constructed (FIG. 9). The BAV3 E3 region falls approximately between m.u. 77 and 82. In our first series of vectors we replaced a 696 bp XhoI-NcoI E3 deletion (between m.u. 78.8 and 80.8) with a NruI-SalI cloning sites for insertion of foreign genes to obtain pSM14del2. A 1716 bp BsmI-SspI fragment containing the luciferase gene was isolated and first inserted into an intermediate plasmid, pSM41, in the E3 locus at the SalI site by blunt end ligation to generate pSM41-Luc. The luciferase gene without any exogenous regulatory sequences, was inserted into the E3 locus in the same orientation as the E3 transcription unit. The kan$^r$ gene was inserted into pSM41-Luc at the XbaI site present within the luciferase gene to generate an amp$^r$/kan$^r$ plasmid, pSM41-Luc-Kan. A 7.7 kb fragment containing the BAV3 sequences along with the luciferase gene and the kan$^r$ gene was obtained from pSM41-Luc-Kan by digestion with BamHI and inserted into an amp$^r$ plasmid, pSM51 partially digested with BamHI to replace a 3.0 kb BamHI fragment (lies between m.u. 77.8 and 86.4) to generate a doubly resistant (kan$^r$ & amp$^r$) plasmid, pSM51-Luc-Kan. The kan$^r$ gene was deleted from pSM51-Luc-Kan by partial cleavage with XbaI to generate pSM51-Luc containing the luciferase gene in the E3-parallel orientation.

Figure 10:
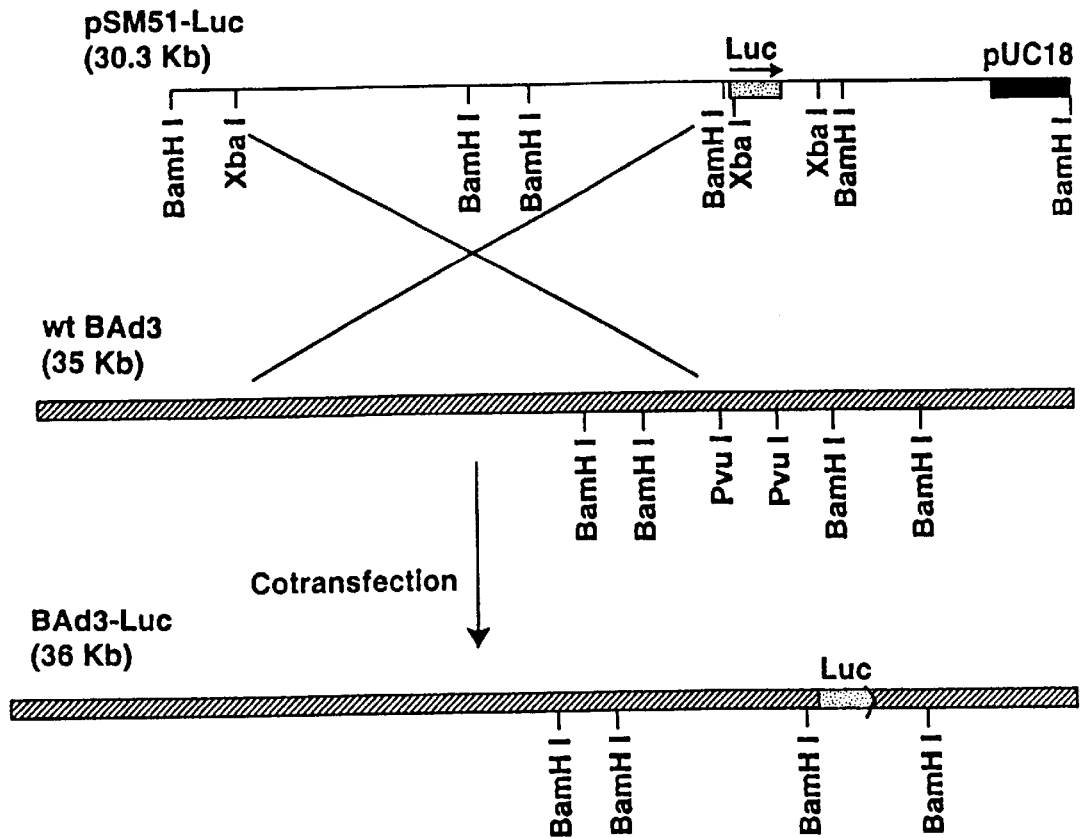
FIG. 10. Generation of BAV3 recombinants containing the firefly luciferase in the E3 region. The plasmid pSM51-Luc contains the BAV3 genome between m.u. 77.8–84.3 and 31.5–100, a 696 bp deletion in E3 and the luciferase gene in E3 in the E3 parallel orientation. The BAV3 genome digested with PvuI and uncut pSM51-Luc were used for cotransfection of MDBK cells transformed with a plasmid containing BAV3 E1 sequences to rescue the luciferase gene in E3 of the BAV3 genome by in vivo recombination. The resulting BAV3-luciferase recombinants (BAV3-Luc) isolated from two independent experiments were named BAV3-Luc (3.1) and BAV3-Luc (3.2). The BamHI restriction map of the BAV3-Luc genome is shown. The position and orientation of the firefly luciferase gene is shown as a hatched arrow.

MDBK cells transformed with a plasmid containing the BAV3 E1 sequences was cotransfected with the wt BAV3 DNA digested with PvuI, which make two cuts within the BAV3 genome at m.u 65.7 and 71.1, and the plasmid, pSM51-Luc to rescue the luciferase gene in E3 of the BAV3 genome by in vivo recombination (FIG. 10). The digestion of the wt BAV3 DNA with PvuI was helpful in minimizing the generation of the wt virus plaques following cotransfection. The left end of the wt BAV3 genome represented by PvuI 'A' fragment falls between m.u. 0 and 65.7, and pSM51-Luc which extends between m.u. 31.5 and 100 (except for E3 deletion replaced with the luciferase gene) have sufficient overlapping BAV3 DNA sequences to generate recombinant viruses.

Two virus plaques were obtained in two independent cotransfection experiments which were grown in MDBK cells. The viral DNA from both plaques was extracted and analyzed by agarose gel electrophoresis after digesting either with BamHI, EcoRI or XbaI to identify the presence and orientation of the luciferase gene in the viral genome (data not shown). In the genomes of both recombinants, the luciferase gene was present in the E3 region in the E3 parallel orientation. The BAV3-luciferase recombinants were plaque purified and named BAV3-Luc (3.1) and BAV3-Luc (3.2) to represent plaques obtained from two independent experiments. Since both recombinant virus isolates were identical they will be referred to as BAV3-Luc. The presence of the luciferase gene in BAV3-Luc isolates are further confirmed by Southern blot analyses and luciferase assays using extracts from recombinant virus-infected cells.

Characterization of BAV3-recombinants

Figures 11A, 11B:
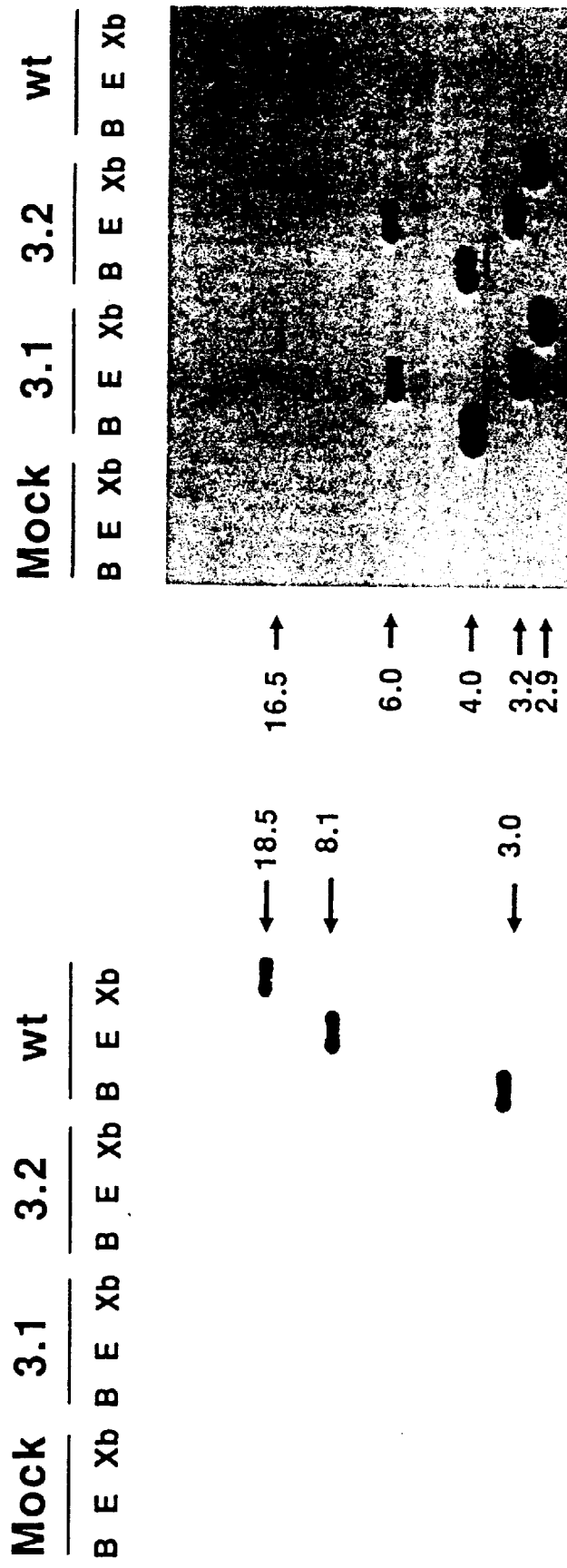
FIGS. 11A–11B. Southern blot analyses of restriction enzymes digested DNA fragments of the wt BAV3 or recombinant genomes by using a 696 bp XhoI-NcoI fragment from pSM14 (FIG. 9) and a DNA fragment containing the luciferase gene as probes. 100 ng DNA isolated from the mock (lanes 1, 2, 3), BAV3-Luc (3.1) (lanes 4, 5, 6), BAV3-Luc (3.2) (lanes 7, 8, 9) or wt BAV3 (lanes 10, 11 12)-infected MDBK cells were digested with BamHI (lanes 1, 4, 7, 10), EcoRI (lanes 2, 5, 8, 11) or XbaI (lanes 3, 6, 9, 12) and analyzed by agarose gel electrophoresis. The DNA fragments from the gel were transferred onto a GeneScreen-Plus™ membrane and hybridized with a 696 bp XhoI-NcoI fragment from pSM14 (FIG. 9) labeled with $^{32}$P using Pharmacia Oligolabeling Kit (panel A). Panel B blot represents duplicate samples as in panel A but was probed with a 1716 bp BsmI-SspI fragment containing the luciferase gene (FIG. 9). The sizes of bands visualized following hybridization are shown in kb on the right in panel A and on the left in panel B.

Southern blot analyses of the wt BAV3 and recombinants genomic DNA digested either with BamHI, EcoRI or XbaI, were carried out to confirm the presence and orientation of the luciferase gene in the E3 locus and the deletion of the 696 bp XhoI-NcoI fragment from E3 of the BAV3-Luc genome (FIG. 11). When the blot was probed with a 696 XhoI-NcoI fragment of E3 of the BAV3 genome (panel A, lanes 4 to 9) no hybridization signal was detected with the DNA fragments from the recombinant viruses, however, the expected bands (3.0 kb BamHI, 8.1 kb EcoRI, and 18.5 kb XbaI) of the wt BAV3 DNA fragments (panel A, lanes 10 to 12) showed hybridization, confirming that the 696 bp XhoI-NcoI fragment of the E3 region was indeed deleted in the BAV3-Luc genomic DNA. In panel B, when an identical blot was probed with the luciferase gene, there were strong hybridization signals with the DNA fragments from the recombinant viruses (4.0 kb BamHI (lane 4 & 7), 6.0 kb & 3.2 kb EcoRI (lanes 5 & 8), 16.7 kb & 2.9 kb XbaI (lanes 6 & 9)). These results confirmed that the BAV3-Luc contains the luciferase gene in the E3 parallel orientation with a 696 bp XhoI-NcoI E3 deletion.

The growth characteristics of the recombinant viruses was compared with the wt BAV3 in a single step growth curve (FIG. 12). Virus titers in MDBK cells-infected with the wt BAV3 started increasing at 12 h post-infection reaching a maximum at 36–48 h post-infection and then declined thereafter. Virus titers of the recombinant viruses also started increasing at 12 h postinfection reaching a maximum at 48 h post-infection and then declined, however, the titers of recombinant viruses remained approximately one log lower than the wt virus. The plaque size of the recombinant viruses were also comparatively smaller than the wt virus (data not shown).

Kinetics of Luciferase Expression by BAV3-Luc

Luciferase activity in BAV3-Luc-infected MDBK cells was monitored at different times post-infection by luciferase assays (FIG. 13). A low level of luciferase activity was first observed at 12 h post-infection reaching a peak at 30 h post-infection and then dropped subsequently. At 30 h post-infection, approximately 425 pg luciferase was detected in $4 \times 10^5$ BAV3-Luc (3.1)—infected MDBK cells. In MDBK cells-infected with the wt BAV3, luciferase expression was not detected (data not shown). The kinetics of luciferase expression by BAV3-Luc (3.1) and BAV3-Luc (3.2) appears very much similar. The kinetics of luciferase expression also showed that the majority of enzyme expression in virus-infected cells seemed to occur late in infection. To determine luciferase expression in the absence of viral DNA replication, BAV3-Luc-infected MDBK cells were incubated in the presence of an inhibitor of DNA synthesis, 1-β-D-arabinofuranosyl cytosine (AraC) and luciferase activity was measured in virus-infected cell extracts at various times post-infection and compared to luciferase expression obtained in the absence of AraC (FIG. 14). When the recombinant virus-infected cells were incubated in the presence of AraC, luciferase expression at 18, 24 and 30 h post-infection was approximately 20–30% of the value obtained in the absence of AraC. These results indicated that the majority of luciferase expression in MDBK cells infected with BAV3-Luc took place after the onset of viral DNA synthesis. To confirm this MDBK cells-infected with the BAV3-Luc were grown in the absence or presence of AraC, harvested at 18 h, 24 h, and 30 h post-infection, viral DNA extracted and analyzed by dot bot analysis using pSM51-Luc (see FIG. 9) as a probe (data not shown). In the presence of AraC, viral DNA synthesis was severely reduced compared to viral DNA synthesis in the absence of AraC.

Western blot analysis of BAV3-Luc-infected cells Luciferase was expressed as an active enzyme as determined by luciferase assays using extracts from MDBK cells-infected with BAV3-Luc (see FIG. 13). The luciferase gene without any exogenous regulatory sequences was inserted into E3 of the BAV3 genome, therefore, there was a possibility of luciferase expression as a fusion protein with part of an E3 protein if the luciferase gene was in the same frame, Such as, F1 and F3 which represent open reading frames (ORFs) for E3 proteins (FIG. 15) or the fusion protein may arise due to recognition of an upstream initiation codon in the luciferase ORF. To explore this possibility we sequenced the DNA at the junction of the luciferase gene and the BAV3 sequences with the help of a plasmid, pSM51-Luc and a synthetic primer design to bind luciferase coding sequences near the initiation codon (data not shown). The luciferase coding region fell in frame F2. The luciferase initiation codon was the first start codon in this frame, however, the ORF started at 84 nucleotides upstream of the luciferase start codon. To further confirm that luciferase protein is of the same molecular weight as purified firefly luciferase, unlabeled mock-infected, wt BAV3-infected or BAV3-Luc-infected MDBK cell extracts were reacted with an anti-luciferase antibody in a Western blot (FIG. 16). A 62 kDa polypeptide band was visible in the BAV3-Luc (lane 3 and 4)-infected cell extracts which were of the same molecular weight as pure firefly luciferase (lane 5). We are not sure whether a band of approximately 30 kDa which also reacted with the anti-luciferase antibody in lanes 3 and 4 represented a degraded luciferase protein.

The majority of luciferase expression is probably driven from the major late promoter (MLP) to provide expression paralleling viral late gene expression, moreover, the enzyme expression seen in the presence of AraC may be taking place from the E3 promoter. In HAd5 vectors, foreign genes without any exogenous regulatory sequences when inserted in E3 also displayed late kinetics and were inhibited by AraC. The BAV3 recombinant virus replicated relatively well in cultured cells but not as good as the wt BAV3. This is not surprising as infectious virus titers of a number of HAdS recombinants were slightly lower than the wt HAd5 (Bett et al (1993) *J. Virol.* 67:5911–5921). This may be because of reduced expression of fiber protein in recombinant adenoviruses having inserts in the E3 region compared to the wt virus (Bett et al, supra and Mittal et al (1993) *Virus Res.* 28:67–90).

The E3 of BAV3 is approximately half the size of the E3 region of HAd2 or HAd5 and thus has the coding potential for only half the number of proteins compared to E3 of HAd2 or HAd5 (Cladaras et al (1985) *Virology* 140:28–43: Herisse et al (1980) *Nuc. Acids Res.* 8:2173–2192; Herisse et al (1981) *Nuc. Acids Res.* 9:1229–1249 and Mittal et al (1993 *J. Gen. Virol.* 73:3295–3000). BAV3 E3 gene products have been shown to be not required for virus growth in tissue culture. However, presently it is known that BAV3 E3 gene products also evade immune surveillance in vivo like HAds E3 proteins. One of the BAV3 E3 open reading frames (ORFs) has been shown to have amino acid homology with the 14.7 kDa E3 protein of HAds (Mittal et al (1993) supra). The 14.7 kDa E3 protein of HAds prevents lysis of virus-infected mouse cells by tumor necrosis factor (Gooding et al (1988) *Cell* 53:341–346 and Horton et al (1990) *J. Virol.* 64:1250–1255). The study of pathogenesis and immune responses of a series of BAV3 E3 deletion mutants in cattle provides very useful information regarding the role of E3 gene products in modulating immune responses in their natural host.

The BAV3-based vector has a 0.7 kb E3 deletion which can hold an insert up to 2.5 kb in size. The BAV3 E3 deletion can extend probably up to 1.4 kb which in turn would also increase the insertion capacity of this system. The role of the MLP and the E3 promoter is examined to determine their ability to drive expression of a foreign gene inserted into E3 when a proper polyadenylation signal is provided. Exogenous promoters, such as, the simian virus 40 (SV40) promoter (Subramant et al (1983) *Anal. Biochem.* 135:1–15), the human cytomegalovirus immediate early promoter (Boshart et al (1985) *Cell* 43:215–222), and the human beta-actin promoter (Gunning et al (1987) *PNAS, USA* 84:4831–4835) are tested to evaluate their ability to facilitate expression of foreign genes when introduced into E3 of the BAV3 genome.

Recently HAd-based expression vectors are under close scrutiny for their potential use in human gene therapy (Ragot et al (1993) *Nature* 361:647–650; Rosenfeld et al (1991) *Science* 252:431–434; Rosenfeld et al (1992) *Cell* 68:141–155 and Stratford-Perricaudet et al (1990) *Hum. Gene. Ther.* 1:241–256). A preferable adenovirus vector for gene therapy would be one which maintains expression of the required gene for indefinite or for a long period in the target organ or tissue. It may be obtained if the recombinant virus vector genome is incorporate into the host genome or maintained its independent existence extrachromosomally without active virus replication. HAds replicate very well in human, being their natural host. HAds can be made defective in replication by deleting the E1 region, however, how such vectors would maintain the expression of the target gene in a required fashion is not very clear. Moreover, the presence of anti-HAds antibodies in almost every human being may create some problems with the HAd-based delivery system. The adenovirus genomes have a tendency to form circles in non-permissive cells. BAV-based vectors could provide a possible alternative to HAd-based vectors for human gene therapy. As BAV3 does not replicate in human, the recombinant BAV3 genomes may be maintained as independent circles in human cells providing expression of the essential protein for a long period of time.

The foreign gene insertion in animal adenoviruses is much more difficult than HAds because it is hard to develop a cell line which is also good for adenovirus DNA-mediated transfection. This may be one of the major reasons that the development of an animal adenovirus-based expression system has not been reported so far. It took us more than a year to isolate a cell line suitable for BAV3 DNA-mediated transfection. However, the rapid implementation of BAV-based expression vectors for the production of live virus recombinant vaccines for farm animals, is very promising. BAVs grow in the respiratory and gastrointestinal tracts of cattle, therefore, recombinant BAV-based vaccines have use to provide a protective mucosal immune response, in addition to humoral and cellular immune responses, against pathogens where mucosal immunity plays a major role in protection.

Example 5
Generation of Cell Lines Transformed with the BAV3 E1 Sequences

MDBK cells in monolayer cultures were transfected with pSM71-neo, pSM61-kan1 or pSM61-kan2 by a lipofection-mediated transfection technique (GIBCO/BRL, Life Technologies, Inc., Grand Island, N.Y.). At 48 h after transfection, cells were maintained in the MEM supplemented with 5% fetal bovine serum and 700 µg/ml G418. The medium was changed every 3rd day. In the presence of G418, only those cells would grow which have stably incorporated the plasmid DNA used in transfection experiments into their genomes and are expressing the neo$^r$ gene. The cells which have incorporated the neo$^r$ gene might also have taken up the BAV3 E1 sequences and thus expressing BAV3 E1 protein/s. A number of neo$^r$ (i.e., G418-resistant) colonies were isolated, expended and tested for the presence of BAV3 E1 message/s by Northern blot analyses using a DNA probe containing only the BAV3 E1 sequences. Expression of BAV3 E1 protein/s were confirmed by a complimentation assay using a HAd5 deletion mutant defective in E1 function due to an E1 deletion.

Fetal bovine kidney cells in monolayers were also transfected with pSM71-neo, pSM61 kan-1 or pSM61-kan2 by the lipofection-mediated transfection technique, electroporation (Chu et al (1987) Nucl. Acids Res. 15:1311–1326), or calcium phosphate precipitation technique (Graham et al (1973) Virology 52:456–467). Similarly, a number of G418-resistant colonies were isolated, expended and tested for the presence of BAV3 E1 gene products as mentioned above.

Example 6
Generation of a BAV3 Recombinant Containing the Beta-galactosidase Gene as an E1 Insert As E1 gene products are essential for virus replication, adenovirus recombinants containing E1 inserts will grow only in a cell line which is transformed with the adenovirus E1 sequences and expresses E1. A number of cell line which are transformed with the BAV3 E1 sequences were isolated as described earlier. The technique of foreign gene insertions into the E1 regions is similar to the gene insertion into the E3 region of the BAV3 genome, however, for insertion into E1 there is a need of an E1 transfer plasmid which contains DNA sequences from the left end of the BAV3 genome, an appropriate deletion and a cloning site for the insertion of foreign DNA sequences. G418-resistant MDBK cell monolayers were cotransfected with the wild-type (wt) BAV3 DNA and pSM71-Z following the lipofection-mediated transfection procedure (GIBCO/BRL, Life Technologies, Inc., Grand Island, N.Y.). The monolayers were incubated at 37° C. under an agarose overlay. After a week post-incubation an another layer of overlay containing 300 ug/ml Blu-gal™ (GIBCO/BRL Canada, Burlington, Ontario, Canada) was put onto each monolayer. The blue plaques were isolated, plaque purified and the presence of the beta-galactosidase gene in the BAV3 genome was identified by agarose gel electrophoresis of recombinant virus DNA digested with suitable restriction enzymes and confirmed by beta-galactosidase assays using extracts from recombinant virus infected cells.

DEPOSIT OF BIOLOGICAL MATERIALS

The following materials were deposited and are maintained with the Veterinary Infectious Disease organization (VIDO), Saskatoon, Saskatchewan, Canada.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

| Material Recombinant plasmids | Internal Accession No. | Deposit Date |
| --- | --- | --- |
| pSM51 | pSM51 | Dec 6, 1993 |
| pSM71 | pSM71 | Dec 6, 1993 |

While the present invention has been illustrated above by certain specific embodiments, the specific examples are not intended to limit the scope of the invention as described in the appended claims.

We claim:

1. A live recombinant bovine adenovirus (BAV) expression vector comprising a bovine adenovirus genome with a deletion of all or part of the E1 region;

said expression vector further comprising an insertion, at the site of the deletion, of a non-BAV nucleotide sequence under the control of an effective promoter.

2. A live recombinant bovine adenovirus (BAV) expression vector comprising a bovine adenovirus genome with a deletion of all or part of the E3 region;

said expression vector further comprising an insertion, at the site of the deletion, of a non-BAV nucleotide sequence under the control of an effective promoter.

3. A live recombinant bovine adenovirus (BAV) expression vector comprising a bovine adenovirus genome with deletions of all or part of the E1 region and all or part of the E3 region;

said expression vector further comprising one or more insertions, at the site of at least one of the deletions, of one or more non-BAV nucleotide sequences, said non-BAV nucleotide sequences being under the control of one or more effective promoters.

4. The live recombinant BAV expression vector of claim 1 wherein the non-BAV nucleotide sequence is selected from the group consisting of the cystic fibrosis transmembrane conductance regulator gene, the human minidystrophin gene and the α-1 antitrypsin gene.

5. The live recombinant BAV expression vector of claim 2 wherein the non-BAV nucleotide sequence is selected from the group consisting of the cystic fibrosis transmembrane conductance regulator gene, the human minidystrophin gene and the α-1 antitrypsin gene.

6. The live recombinant BAV expression vector of claim 3 wherein the non-BAV nucleotide sequence is selected from the group consisting of the cystic fibrosis transmembrane conductance regulator gene, the human minidystrophin gene and the α-1 antitrypsin gene.

7. A method for introducing and expressing a non-BAV nucleotide sequence in a mammalian cell, wherein the method comprises contacting said mammalian cell with a live recombinant BAV expression vector according to claim 1.

8. A method for introducing and expressing a non-BAV nucleotide sequence in a mammalian cell, wherein the method comprises contacting said mammalian cell with a live recombinant BAV expression vector according to claim 2.

9. A method for introducing and expressing a non-BAV nucleotide sequence in a mammalian cell, wherein the method comprises contacting said mammalian cell with a live recombinant BAV expression vector according to claim 3.

10. The method according to claim 7, wherein the non-BAV nucleotide sequence is selected from the group consisting of the cystic fibrosis transmembrane conductance regulator gene, the human minidystrophin gene and the α-1 antitrypsin gene.

11. The method according to claims 8, wherein the non-BAV nucleotide sequence is selected from the group consisting of the cystic fibrosis transmembrane conductance regulator gene, the human minidystrophin gene and the α-1 antitrypsin gene.

12. The method according to claim 9, wherein the non-BAV nucleotide sequence is selected from the group consisting of the cystic fibrosis transmembrane conductance regulator gene, the human minidystrophin gene and the α-1 antitrypsin gene.

* * * * *